(12) United States Patent
Ambruzs et al.

(10) Patent No.: US 10,076,606 B2
(45) Date of Patent: Sep. 18, 2018

(54) INSERTION DEVICES, INSERTION NEEDLES, AND RELATED METHODS

(75) Inventors: William Ambruzs, Austin, TX (US);
Lauren Burns, Phoenix, AZ (US);
Joseph Christian, Austin, TX (US);
Brian Highley, Austin, TX (US); Jason Adams, Frisco, TX (US); Charles Houssiere, Austin, TX (US); Randy Jackson, Frisco, TX (US)

(73) Assignee: Medtronic Minimed, Inc., Northridge, CA (US)

( * ) Notice: Subject to any disclaimer, the term of this patent is extended or adjusted under 35 U.S.C. 154(b) by 804 days.

(21) Appl. No.: 12/808,145

(22) PCT Filed: Dec. 10, 2008

(86) PCT No.: PCT/US2008/086281
§ 371 (c)(1),
(2), (4) Date: Nov. 19, 2010

(87) PCT Pub. No.: WO2009/076470
PCT Pub. Date: Jun. 18, 2009

(65) Prior Publication Data
US 2011/0060287 A1    Mar. 10, 2011

Related U.S. Application Data

(60) Provisional application No. 61/012,477, filed on Dec. 10, 2007, provisional application No. 61/057,752, (Continued)

(51) Int. Cl.
*A61M 5/178* (2006.01)
*A61M 5/158* (2006.01)

(52) U.S. Cl.
CPC ..... *A61M 5/158* (2013.01); *A61M 2005/1581* (2013.01); *A61M 2005/1585* (2013.01)

(58) Field of Classification Search
CPC .......... A61M 2005/1585; A61M 5/158; A61B 5/6849; A61B 5/14532
(Continued)

(56) References Cited

U.S. PATENT DOCUMENTS 4,445,510 A    5/1984 Rigby
4,747,831 A    5/1988 Kulli
(Continued)

FOREIGN PATENT DOCUMENTS

WO    WO 2005/120623    12/2005
WO    WO 2006/061027    6/2006
WO    WO 2008155377    * 12/2008

OTHER PUBLICATIONS

International Search Report and Written Opinion issued in PCT/US2008/086281, dated Oct. 7, 2009.
(Continued)

*Primary Examiner* — Matthew F DeSanto
(74) *Attorney, Agent, or Firm* — Norton Rose Fulbright US LLP

(57) ABSTRACT

Insertion devices for installing insertion sets to a user, insertion needles, methods for loading insertion devices with insertion sets, methods for installing insertion sets, methods for instructing others how to load and/or install insertion sets, and certain aspects of insertion sets, including insertion needle hubs.

14 Claims, 61 Drawing Sheets

Related U.S. Application Data filed on May 30, 2008, provisional application No. 61/077,151, filed on Jun. 30, 2008.

(58) Field of Classification Search
USPC ............... 604/110, 115, 116, 134–136, 162, 604/164.01–164.12, 533, 534, 539, 157
See application file for complete search history.

(56) References Cited

U.S. PATENT DOCUMENTS

| | | |
|---|---|---|
| 5,176,662 A | 1/1993 | Bartholomew |
| 5,478,316 A | 12/1995 | Bitdinger et al. |
| 5,522,831 A | 6/1996 | Sleister et al. |
| 5,575,777 A | 11/1996 | Cover et al. |
| 5,709,662 A | 1/1998 | Olive et al. |
| 5,827,315 A | 10/1998 | Yoon |
| 5,851,197 A | 12/1998 | Marano et al. |
| 5,931,815 A | 8/1999 | Liu |
| 5,968,011 A | 10/1999 | Larsen et al. |
| 6,015,396 A | 1/2000 | Buttgren et al. |
| 6,090,068 A | 7/2000 | Chanut |
| 6,093,172 A | 7/2000 | Funderburk et al. |
| 6,254,573 B1 | 7/2001 | Haim et al. |
| 6,293,295 B1 | 9/2001 | Bongrand et al. |
| 6,428,528 B2 | 8/2002 | Sadowski |
| 6,517,517 B1 | 2/2003 | Farrugia et al. |
| 6,607,509 B2 | 8/2003 | Bobroff et al. |
| 6,641,561 B1 | 11/2003 | Hill et al. |
| 6,685,674 B2 | 2/2004 | Douglas et al. |
| 6,830,562 B2 | 12/2004 | Mogensen et al. |
| 6,837,876 B2 | 1/2005 | Bally et al. |
| 6,991,619 B2 | 1/2006 | Marano-Ford et al. |
| 6,991,620 B2 | 1/2006 | Marano-Ford et al. |
| 6,997,907 B2 | 2/2006 | Safabash et al. |
| 7,022,108 B2 | 4/2006 | Marano-Ford et al. |
| 7,056,302 B2 | 6/2006 | Douglas |
| 7,252,651 B2 | 8/2007 | Haider et al. |
| 2001/0021869 A1 | 9/2001 | Bishay et al. ............... 607/116 |
| 2003/0109829 A1 | 6/2003 | Mogensen et al. |
| 2003/0130619 A1 | 7/2003 | Safabash et al. |
| 2003/0158520 A1* | 8/2003 | Safabash ............... A61M 5/158 604/116 |
| 2003/0199823 A1 | 10/2003 | Bobroff et al. |
| 2003/0225373 A1 | 12/2003 | Bobroff et al. |
| 2004/0002682 A1 | 1/2004 | Kovelman et al. |
| 2004/0024367 A1 | 2/2004 | Gilbert |
| 2004/0133164 A1* | 7/2004 | Funderburk ....... A61B 5/14532 604/134 |
| 2004/0204687 A1 | 10/2004 | Mogensen et al. |
| 2005/0033235 A1 | 2/2005 | Flint |
| 2005/0043687 A1 | 2/2005 | Mogensen et al. |
| 2005/0101912 A1 | 5/2005 | Faust et al. |
| 2005/0124936 A1* | 6/2005 | Mogensen et al. ........... 604/136 |
| 2005/0131346 A1 | 6/2005 | Douglas |
| 2005/0131347 A1 | 6/2005 | Marano-Ford et al. |
| 2006/0069351 A9 | 3/2006 | Safabash et al. |
| 2006/0095014 A1 | 5/2006 | Ethelfeld |
| 2006/0129123 A1 | 6/2006 | Wojcik |
| 2006/0135908 A1 | 6/2006 | Liniger et al. |
| 2006/0161108 A1* | 7/2006 | Mogensen ............. A61M 5/158 604/164.01 |
| 2006/0217663 A1 | 9/2006 | Douglas |
| 2006/0229559 A1 | 10/2006 | Marano-Ford et al. |
| 2006/0229560 A1 | 10/2006 | Marano-Ford et al. |
| 2007/0016129 A1 | 1/2007 | Liniger et al. |
| 2007/0276320 A1 | 11/2007 | Wall et al. |
| 2008/0319414 A1* | 12/2008 | Yodfat ................. A61B 5/6849 604/506 |

OTHER PUBLICATIONS

Section 5 of EPO Communication Pursuant to Article 94(3) EPC issued in EP App. No. 08 859 889.1, dated Apr. 7, 2016.
Oct. 10, 2016 Response to Apr. 7, 2016 EPO Communication in EP App. No. 08 859 889.1.
Jun. 7, 2017 EPO Communication issued in EP App. No. 08 859 889.1.

* cited by examiner

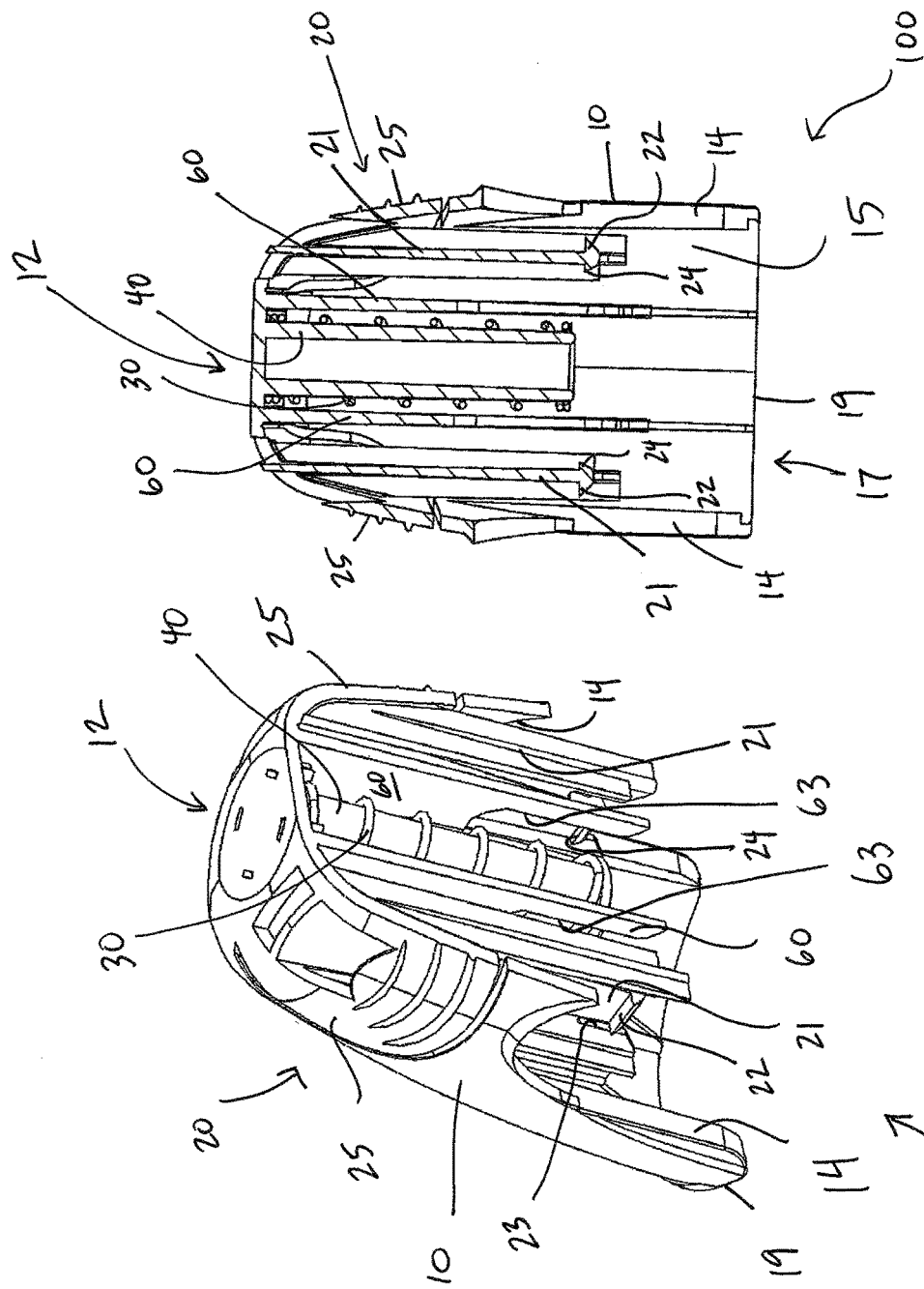

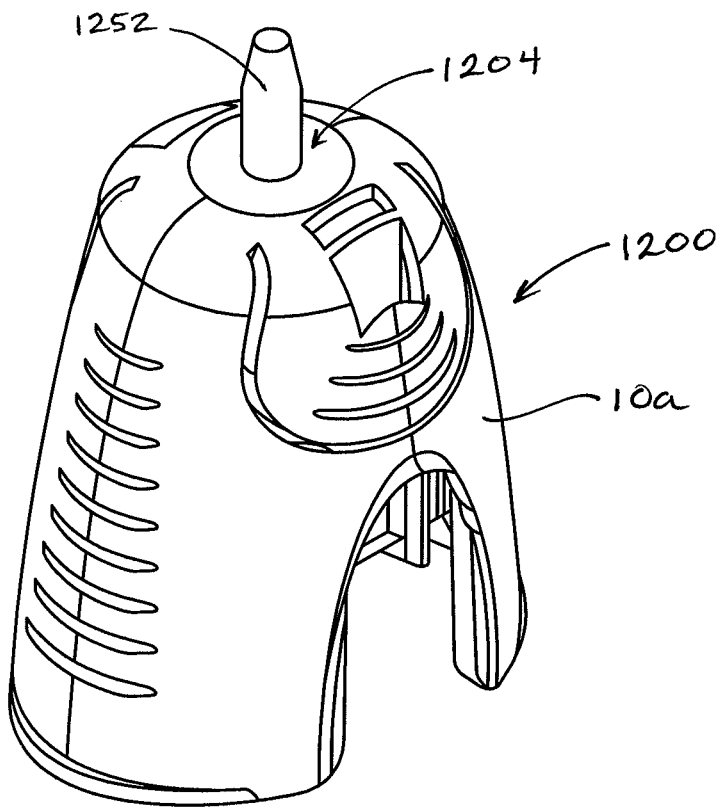
FIG. 57
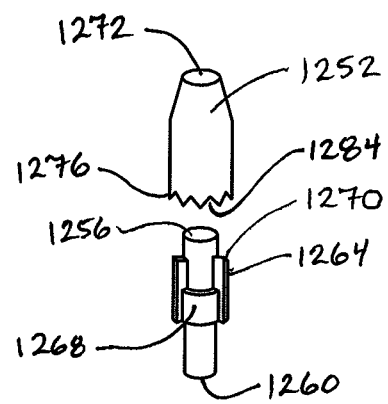
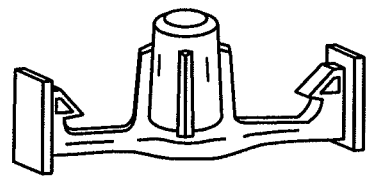
FIG. 59

INSERTION DEVICES, INSERTION NEEDLES, AND RELATED METHODS

CROSS-REFERENCES TO RELATED APPLICATIONS

This application is a national phase application under 35 U.S.C. § 371 of International Application No. PCT/US2008/086281 filed Dec. 10, 2008, which claims priority to: (1) U.S. Provisional Patent Application Ser. No. 61/012,477 filed Dec. 10, 2007; (2) U.S. Provisional Patent Application Ser. No. 61/057,752 filed May 30, 2008; and (3) U.S. Provisional Patent Application Ser. No. 61/077,151 filed Jun. 30, 2008, all of which are specifically incorporated by reference without disclaimer.

BACKGROUND OF THE INVENTION

1. Field of the Invention

The invention relates generally to devices that can be used to install fluid delivery devices such as insertion sets, including those compatible with a pump and those that are not compatible with a pump, to a user. The invention also relates to methods of loading insertion devices with an insertion set, to methods of installing insertion sets and to methods of instructing another (or others) on how to install an insertion set. The invention also relates to insertion needles, and the hubs of those needles. The invention also relates to insertion sets that include an embodiment of the present insertion needles. The invention also relates to assemblies or systems that include an insertion device and an insertion set.

2. Description of Related Art

Examples of insertion devices include those disclosed in U.S. Pat. Nos. 6,607,509; 6,830,562; 6,991,619; and 7,056,302, and in U.S. Patent Application Pub. No. US 2006/0135908.

SUMMARY OF THE INVENTION

The present insertion devices can be used to install a fluid delivery device, such an insertion set, to a user. Some embodiments of the present insertion devices are re-usable. Some embodiments of the present insertion devices comprise, consist essentially of, or consist of a housing having a proximal end; and a driver coupled to the housing; where the insertion device is configured so that if it retains an insertion set in a pre-installed position, the driver will apply a force to the insertion set in the direction of the proximal end of the housing. In some embodiments, the configuration of the insertion device that allows it to retain an insertion set in a pre-installed position includes an insertion set retention mechanism coupled to the housing and configured to retain an insertion set in a pre-installed position. In some embodiments, all the elements of the insertion device other than the driver may be made from a single piece of material.

The present insertion devices may be used to hold an insertion set in a pre-installed position with a piercing member of the insertion set pointed along an insertion axis and toward an open end of the device. In some embodiments, the driver that will apply a force to a loaded insertion set, and that force will be opposed by a force acting on the insertion set from another portion of the insertion device, so that the insertion set will not move relative to the insertion device before being released.

Some embodiments of the present insertion devices are driver-less, meaning they do not include a driver (such as a spring). Some such embodiments comprise, consist essentially of, or consist of a housing having a proximal end; and an insertion set retention mechanism coupled to the housing, the insertion set retention mechanism being configured to retain an insertion set in a pre-installed position and comprising two insertion set retention elements actuatable by a user; where the insertion device does not include a driver.

Some embodiments of the present insertion set installation instruction methods include instructing a person on how to use an insertion device, the instructing including demonstrating the following steps to the person: coupling an insertion set to the insertion device such that the insertion set is positioned in a pre-installed position and such that a driver of the insertion device is exerting a force on the insertion set that is opposed by a force exerted on the insertion set by another portion of the insertion device. The instructing may also include placing the loaded insertion device next to a person's skin, and installing the insertion set to the person by releasing the insertion set from the insertion device.

Some of the present devices comprise systems (which may be characterized as assemblies or combinations) that include both an insertion device and an insertion set.

Some of the present devices comprise insertion needles and, more specifically, insertion needle hubs.

Some embodiments of the present insertion devices comprise, consist essentially of, or consist of a housing having a proximal end; and a charging mechanism coupled to the housing; where the insertion device is configured such that the charging mechanism will be operable between an uncharged configuration and a charged configuration if the insertion device retains in a pre-installed position an insertion set having a driver.

Some embodiments of the present insertion devices comprise, consist essentially of, or consist of a housing having a proximal end; a charging mechanism coupled to the housing; and a driver coupled to the charging mechanism; where the insertion device is configured such that the charging mechanism will be operable between an uncharged configuration and a charged configuration if the insertion device retains in a pre-installed position an insertion set having a piercing member, the pre-installed position being one in which the piercing member will not contact a flat surface if the proximal end of the housing is placed against the flat surface.

Some embodiments of the present kits comprise, consist essentially of, or consist of an insertion set having a driver and a piercing member; and an insertion device. In some embodiments, the insertion device comprises: a housing having a proximal end; an insertion set retention mechanism coupled to the housing; and a charging mechanism coupled to the housing, the charging mechanism operable between (1) an uncharged configuration and (2) a charged configuration in which the driver applies a force to the insertion set in the direction of the proximal end of the housing; where the insertion set retention mechanism retains the insertion set in a pre-installed position, and the insertion set retention mechanism is actuatable to release the insertion set from the pre-installed position. In some embodiments of the present kits, the charging mechanism is in the uncharged configuration. Some embodiments of the present kits further comprise a package supporting the insertion device. In some embodiments, the package surrounds at least a portion of the insertion device. In some embodiments, the package comprises a blister pack. In some embodiments, the blister pack is hermetically sealed. In some embodiments, the blister pack comprises a back portion and a front portion attached to the back portion by a seam. In some embodiments, the seam is hermetically sealed.

Some embodiments of the present methods comprise, consist essentially of, or consist of positioning an insertion device over an installation site on the user's skin, the insertion device retaining an insertion set in a pre-installed position and the insertion set having a driver. In some of these embodiments, the insertion device comprises a housing having a proximal end; an insertion set retention mechanism coupled to the housing; and a charging mechanism coupled to the housing; where the insertion device is configured such that the charging mechanism will be operable between an uncharged configuration and a charged configuration if the insertion device retains in a pre-installed position an insertion set having a driver; and where the insertion set retention mechanism retains the insertion set in a pre-installed position, and the insertion set retention mechanism is actuatable to release the insertion set from the pre-installed position Some embodiments of the present methods further comprise releasing the insertion set by actuating the insertion set retention mechanism, thus allowing the driver to advance a piercing member and a cannula of the insertion set into the user's skin. Some embodiments of the present methods comprise operating the charging mechanism into the charged configuration prior to actuating the insertion set retention mechanism. Some embodiments of the present methods comprise repeating the positioning and the releasing using the same insertion device and another insertion set.

Any embodiment of any of the present devices, systems, kits, and methods may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Details associated with these embodiments and others are provided below.

BRIEF DESCRIPTION OF THE DRAWINGS

The following drawings illustrate by way of example and not limitation. Identical reference numbers do not necessarily indicate an identical structure. Rather, the same reference number may be used to indicate a similar feature or a feature with similar functionality, as may non-identical reference numbers. Every feature of each embodiment is not always labeled in every figure in which that embodiment appears, in order to keep the figures clear. FIGS. 1-19, 55, and 56 are drawn to scale (except for the constrained position of the spring shown in FIGS. 18 and 19, the springs shown in FIGS. 55 and 56, and the version of the alignment post 40 shown in FIG. 56), meaning the sizes of the depicted elements are accurate relative to each other for at least one set of embodiments of the present insertion devices.

FIGS. 1 and 2 are perspective views of one embodiment of the present insertion devices.

FIG. 3 is a front view of the embodiment shown in FIGS. 1 and 2.

FIG. 4 is a side view of the embodiment shown in FIGS. 1 and 2.

FIG. 5 is a top view of the embodiment shown in FIGS. 1 and 2.

FIG. 6 is a bottom perspective view of the embodiment shown in FIGS. 1 and 2; the driver is not shown in this view.

FIG. 7 is another bottom perspective view of the embodiment shown in FIGS. 1 and 2; the driver is shown in this view.

FIG. 8 is a cross-sectional view, shown in perspective, of the embodiment shown in FIGS. 1 and 2.

FIG. 9 is another cross-sectional view, shown in perspective, of the embodiment shown in FIGS. 1 and 2.

FIG. 10 is another cross-sectional view, taken along a plane perpendicular to the plane along which the FIG. 8 cross section is taken, and shown in perspective, of the embodiment shown in FIGS. 1 and 2.

FIG. 11 is a cross-section view of the embodiment shown in FIGS. 1 and 2 taken along the same plane as the FIG. 8 cross-sectional view.

FIG. 12 is another cross-sectional view, shown in perspective, of the embodiment shown in FIGS. 1 and 2.

FIG. 13 is a cross-section view of the embodiment shown in FIGS. 1 and 2 taken along the same plane as the FIG. 9 cross-sectional view.

FIGS. 14-16 are perspective views of an embodiment of an insertion needle hub that can be retained by the depicted embodiment of the present insertion devices (FIG. 16 shows a piercing member that is attached to the hub).

FIG. 17 is a perspective view of the embodiment shown in FIGS. 1 and 2, loaded with an insertion set (that includes the FIGS. 14-16 insertion needle hub) that is oriented in a pre-installed position.

FIG. 18 is a cross-sectional view of the loaded embodiment from FIG. 17, shown in perspective, taken along a plane perpendicular to the plane along which the FIG. 10 cross section is taken.

FIG. 19 is another cross-sectional view of the loaded embodiment from FIG. 17, shown in perspective, taken along a plane perpendicular to the plane along which the FIG. 18 cross section is taken.

FIG. 55 is a cross-sectional view of an embodiment of one of the present insertion sets that includes an insertion needle that includes a driver attached to the insertion needle hub. The cross section shown is taken along a plane that is parallel to an axis that is substantially centered in the actual needle of the depicted insertion needle; furthermore, that axis is positioned in the plane.

FIG. 56 is a cross-sectional view of a loaded version of an embodiment of the present insertion devices that does not have a driver; the insertion device is loaded with an embodiment of the present insertion sets that has an insertion needle that includes a driver. The cross section shown is taken along the same plane as the cross section shown in FIG. 55.

FIG. 57 is a perspective view of an embodiment of one of the present insertion devices having a charging mechanism.

FIG. 59 is an exploded perspective view of portions of the charging mechanism of the embodiment shown in FIG. 57.

DESCRIPTION OF ILLUSTRATIVE EMBODIMENTS

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device, a system, a kit, or a method that "comprises," "has," "contains," or "includes" one or more recited elements or steps possesses those recited elements or steps, but is not limited to possessing only those elements or steps; it may possess elements or steps that are not recited. Likewise, an element of a device, system, kit, or method that "comprises," "has," "contains," or "includes" one or more recited features possesses those features, but is not limited to possessing only those features; it may possess features that are not recited. Furthermore, a structure, such as one of the present insertion devices, that is configured in a certain way must be configured in at least that way, but also may be configured in a way or ways that are not specified.

The claims, as originally filed, cover insertion devices and do not require an insertion set (or any portion of an insertion set) in order to be met.

The terms "a" and "an" are defined as one or more than one unless this disclosure explicitly requires otherwise. The terms "substantially" is defined as at least close to (and includes) a given value or state (preferably within 10% of, more preferably within 1% of, and most preferably within 0.1% of). The term "coupled" is defined as connected, although not necessarily directly, and not necessarily mechanically; two items that are "coupled" may be integral with each other.

The present insertion devices may be used to install a fluid delivery device, such as an insertion set designed to work with a pump or an insertion set designed to work without a pump (such as an injection port), to a user. A user (or someone helping a user, such as a relative, physician, or physician's assistant) can couple an insertion set to one of the present insertion devices such that the insertion set is in a pre-installed position, prepare the insertion set for installation by removing any adhesive patch backing or the like, place the loaded insertion device against the user's skin, and actuate the insertion set retention mechanism (such as by depressing the release elements shown in the figures) to allow the insertion device's driver to advance the insertion set from its pre-installed position to an advanced position that will install the insertion set to the user. If the insertion device has been configured to be re-usable, that process may be repeated when it is time for the user to install a new insertion set.

Insertion Devices Having a Driver

Figure 17:
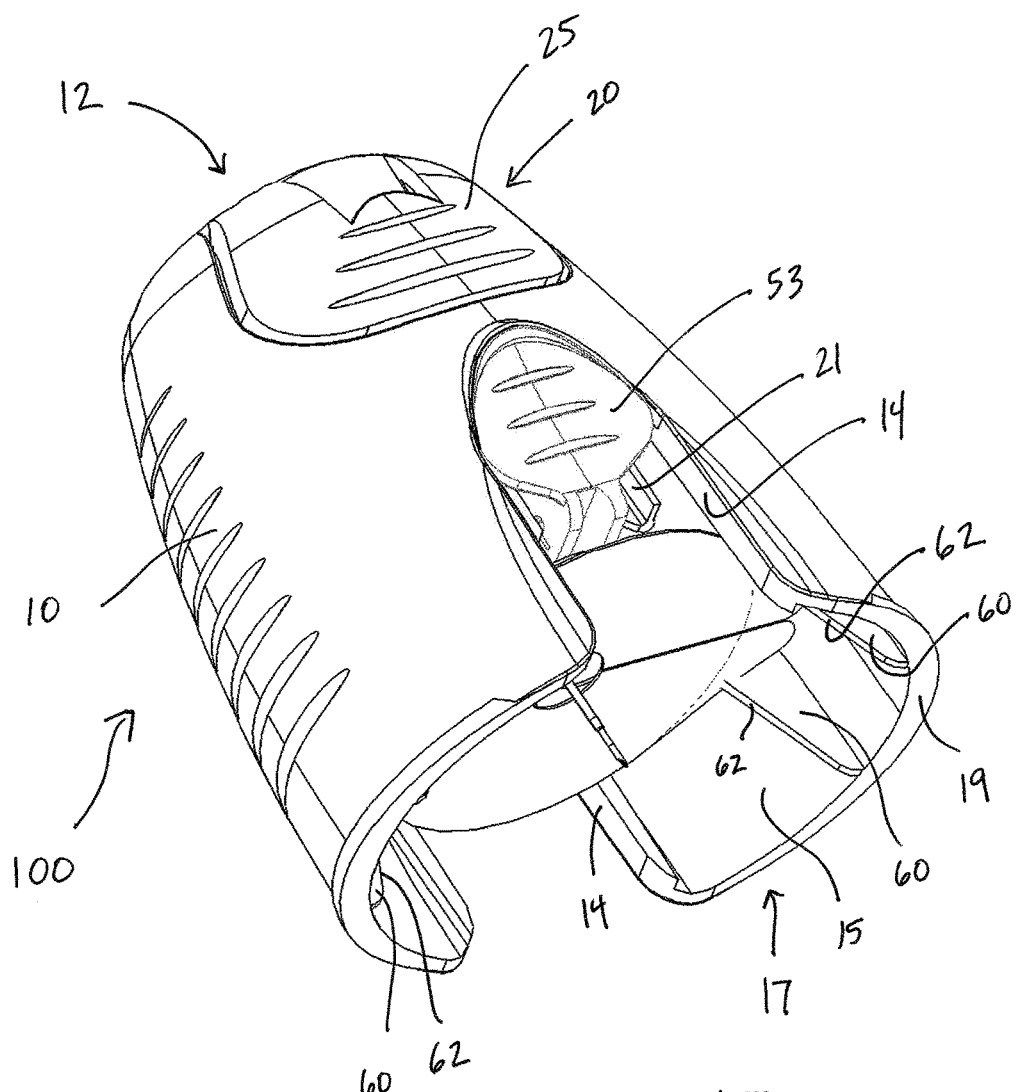
Figure 18:
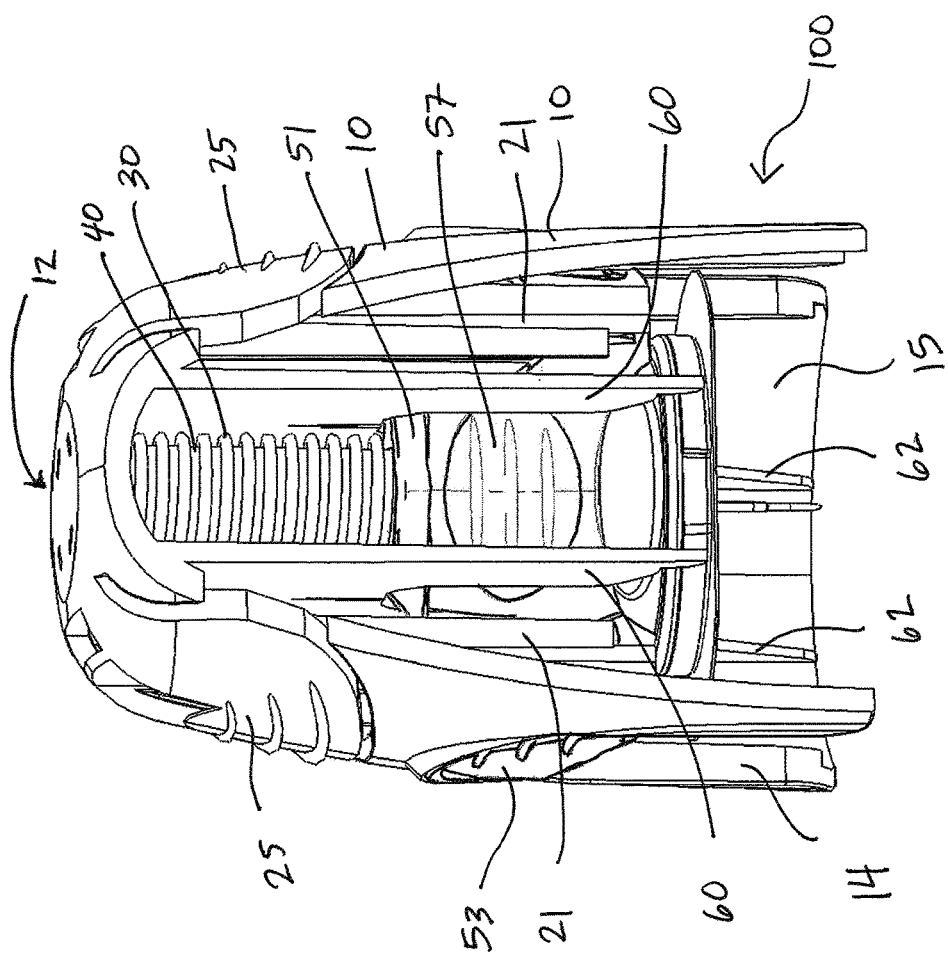

The figures illustrate one embodiment of the present insertion devices. Insertion device 100 comprises a housing 10 and a driver 30. Insertion device 100 is configured so that if it retains an insertion set in a pre-installed position (see the position of the insertion set shown in FIGS. 17-19), driver 30 will apply a force to the insertion set in the direction of proximal end 17 of housing 10. In the depicted embodiment of the present insertion devices, the configuration of insertion device 100 that allows it to retain an insertion set in this manner is achieved with insertion set retention mechanism 20, which is coupled to housing 10 and which is configured to retain (e.g., hold) a given insertion set in a pre-installed position. In the depicted embodiment, insertion set retention mechanism 20 comprises a pair of insertion set retention elements 21, which are actuatable by a user.

The insertion set retention mechanism of one of the present insertion devices may be configured in different ways to be actuated by a user to release a retained insertion set. In the depicted embodiment, each insertion set retention element 21 of the mechanism is coupled to (and, more specifically, directly connected to) a release element 25 (which is part of the retention mechanism) that a user can manipulate with his or her fingers, such as by pressing the release element inwardly (e.g., toward the center of the insertion device). Because of the direct connection between them, movement of the release element causes the retention element to move. In other embodiments, however, the release and retention elements may be not directly connected. Instead, and for example, a space may exist between a given release element and the insertion set retention element it is configured to move so that contact between the two occurs only when the release element is actuated (e.g., moved by the user to a release position). In the depicted embodiment, the retention and release elements are integral with each other (though they need not be) and with housing 10 (though they need not be). More specifically, in the depicted embodiment, each retention element 21 is integrally connected to housing 10 at the top end 12 of housing 10 through release element 25 in a hinge-like manner; as a result, the release and retention elements move non-linearly when actuated (e.g., they move along a curved path).

Each insertion set retention element 21 includes an insertion set-engaging portion 22. As the figures show, the two insertion set-engaging portions 22 extend away from each in opposite directions that are parallel to each other but not aligned. In other embodiments, the insertion set retention elements are configured so that their insertion set-engaging portions extend away from each in opposite directions along the same line. Insertion set retention elements 21 are configured (through, at least in part, insertion set-engaging portions 22) to keep an insertion set coupled to the insertion device and retained in a pre-installed position until a user actuates release elements 25.

Insertion needle hub 50 shown in the present figures is an example of an insertion needle hub that can be used with the depicted embodiment of the present insertion devices. Insertion needle hub 50 has two outwardly-facing gripping elements 52, each having an exterior grip surface 53, and an inwardly-projecting retention element 54 (which may be characterized as a retention clip or a retention tab). Each insertion set-engaging portion 22 is configured to contact an inwardly-projecting retention element 54 so that the insertion needle hub (and therefore the remainder of the insertion set that is coupled to the insertion needle hub) can be retained by the insertion device in a pre-installed position. More specifically, the two inwardly-projecting retention elements 54 of insertion needle hub 50 will interfere with (or "catch" on) the two insertion set-engaging portions 22 of the insertion set retention elements when the insertion set is in a pre-installed position and thus prevent driver 30, which will be in a constrained position and exerting a force on the insertion set in the direction of proximal end 17 of the housing, from advancing the insertion set toward proximal end 17 (e.g., toward an advanced position).

As the figures show, the inwardly-projecting retention elements 54 are not centered with respect to each other (e.g., they are offset from a plane (not shown) that bisects the insertion needle hub, as are insertion set-engaging portions 22 of insertion set retention elements 21), and each is joined to central portion 57 of the insertion needle hub through a stiffening rib 56, the stiffening ribs also being offset from a plane that bisects the insertion needle hub. The offset configuration of the inwardly-projecting retention elements 54 enhances the structural rigidity of insertion needle hub 50, though such a configuration may be absent from other embodiments of an insertion needle hub configured for use with embodiments of the present insertion devices. Insertion set retention elements 21 each includes a notch 23 for fitting over stiffening rib 56 when the depicted insertion set is retained by insertion device 100 and in a pre-installed position. In other embodiments of the present insertion devices, as noted above, insertion set-engaging portions 22 are centered with respect to each other and insertion set retention elements 21 do not possess notches 23. Such other embodiments could be used with an insertion needle hub that had centered inwardly-projecting elements 54 and no stiffening ribs 56.

Each insertion set retention element 21 also includes an insertion set-stopping portion 24 (which extends away from the insertion set-engaging portion 22 of that retention element 21), and together the insertion set-stopping portions are configured to keep an insertion set that has been released from traveling too far in certain circumstances. For example, the configuration of insertion set-stopping portions 24 shown in the figures will interfere with top rim 51 of insertion needle hub 50 when release elements 25 are in an actuated position (e.g., pushed inwardly). As a result, if a user of a loaded version of insertion device 100 accidentally depresses and holds release elements 25, top rim 51 will contact depressed insertion set-stopping portions 24 and the released insertion set will not fly out of the insertion device. Insertion set-stopping portions 24 may be sized sufficiently (e.g., made sufficiently "deep") that they interfere with top rim 51 even when they are not depressed, such that an accidentally released insertion set will be retained by the insertion device even if the release elements are not held in a depressed (or actuated) position; such insertion set-stopping portions 24 also may interfere with top rim 51 after installation and as the insertion device is removed from the use, thus allowing the user to pull insertion needle hub 50 out of the installed insertion set when he or she removes the insertion device.

As in the depicted embodiment, one of the present insertion devices may be configured so that the distance the bottom (or proximal) end of the driver travels between (a) the position it will be in when an insertion set is retained by the device in a pre-installed position and (b) the position it will have when a particular insertion set is installed is less than the distance between (c) the portion of the insertion needle hub of that insertion set that will interfere with insertion set-stopping portion 24 (which is the bottom surface of top rim 51) and (d) the top surface of insertion set-stopping portion 24. Such a configuration on an insertion device that has been configured for insertion set-stopping portions prevents an insertion set that is being installed (as moved by the driver) from prematurely stopping before installation is complete.

Top end 12 of housing 10 is substantially closed in the depicted embodiment. Open proximal end 17 of housing 10 is where a given insertion set is loaded by a user. Open proximal end 17 is defined in part by proximal end edge 19, a portion of which will rest against a user's skin during the installation of an insertion set. Proximal end edge 19 includes opposing slots 14 that are configured to allow a user to access outwardly-facing gripping elements 52 by their respective exterior grip surfaces 53. As the figures show, housing 10 of the depicted embodiment has a reinforced (e.g., enlarged, or thickened) upper edge portion defining the top of each slot 14 that is configured to contact or at least be near a portion of the upper edge of each outwardly-facing gripping element 52 when the insertion set of which the grip elements are a part is coupled to insertion device 100 and in a pre-installed position. In the depicted embodiment of insertion device 100, proximal end 17 has an oval-like profile.

Release elements 25 of insertion set retention mechanism 20 of insertion device 100 have exterior, user-actuatable surfaces that include surface relief (in the form of multiple ridges) that is configured to enhance the gripability (or decrease the likelihood of slippage) of those surfaces by a user (versus a surface without such surface relief). A portion (e.g., a substantial portion) of each of those user-actuatable surfaces is positioned between one of the slots 14 and top end 12 of housing 10. The sides of housing 10 that do not include slots 14 also include surface relief (in the form of multiple indentions) that is configured to increase to enhance the gripability (or decrease the likelihood of slippage) of the housing by a user (versus a housing without such surface relief).

Driver 30 of insertion device 100 may be coupled to housing 10 in any suitable fashion. Housing 10 has an interior surface that defines an inner cavity 15 that extends from the top of the interior surface to the open proximal end 17 of the housing. In the depicted embodiment, driver 30 comprises a helical spring that is coupled to housing 10 with driver retention clips 18 (in the depicted embodiment, there are four of them) that are positioned near the top portion of inner cavity 15. The spring is capable of movement between constrained and unconstrained positions. Housing 10 has an insertion axis 13, which is oriented parallel to the direction that an insertion set can be installed to a user (which, in the depicted embodiment, is perpendicular to the plane in which the open proximal end 17 of the housing sits). Driver 30 is oriented parallel to insertion axis 13, which (in the depicted embodiment) is substantially centered within driver 30.

The depicted embodiment of insertion device 100 also includes alignment post 40, which is coupled to housing 10 near the top portion of inner cavity 15 and which is positioned inside of driver 30. Alignment post 40 is integral with housing 10 in the depicted embodiment, though it need not be. Other embodiments (not depicted) may not include an alignment post where another structure or structures adequately align the insertion set to be installed during the installation process. Alignment post 40 is configured to fit within cavity 55 in insertion needle hub 50 of an insertion set that can be installed using insertion device 100. In the depicted embodiment, alignment post 40 is hollow and insertion needle hub stem 58 of insertion needle hub 50 is configured to fit within alignment post 40 when the insertion set is coupled to insertion device 100 and in a pre-installed position. The fit between stem 58 and the interior surface of post 40 can be configured to be a tight friction fit, but one that can be overcome by driver 30 during installation. Alignment post 40 is configured to help properly orient for installation an insertion set that is coupled to insertion device 100 and in a pre-installed position. The depicted embodiment of alignment post 40 has a cylindrical shape, but may have a different shape in other embodiments, and also may be not hollow in other embodiments.

The depicted embodiment of insertion device 100 also includes an interior rib structure that, in the depicted embodiments, includes two ribs 60 that are positioned on either side of alignment post 40 and driver 30, and that extend downwardly from the top portion of inner cavity 15 of housing 10 toward open proximal end 17. The ribs provide structural support for the housing, and tend to keep it from flexing when it is used. Ribs 60 include a proximal edge 62 that can be configured with any suitable profile, such as one having at least a portion that will contact at least a portion of an insertion set that is coupled insertion device 100 and in a pre-installed position. In addition, proximal edge 62 of each rib 60 includes a slot 63 that can be configured (as is the depicted version) to mate with (e.g., contact) at least a portion of an insertion needle hub, such as needle hub 50. Each slot 63 (which may be characterized as a rib slot) is positioned beside driver 30. Ribs 60 are coupled to housing 10. More specifically, they are integral with housing 10 in the depicted embodiment, though they need not be.

One manner in which a user can couple an insertion set to insertion device 100 follows. With one hand, a user can grip the insertion needle hub (e.g., insertion needle hub 50) with the thumb and forefinger of one hand. The other hand can hold housing 10. The user can then align the gripping elements of the insertion needle hub in slots 14 of housing 10 so that the needle guard of the insertion set is facing away from the inner cavity of the housing. The user can then slide the insertion set (via the gripping elements of the insertion needle hub) up slots 14 toward top end 12 of housing 10 until the retention tabs of the insertion needle hub catch on insertion set-engaging portions 22. When this occurs, driver 30 will be in contact with the top surface of insertion needle hub 50, and in a compressed or constrained state. The user can then remove any needle guard that exists from the insertion set and any adhesive backing that exists. With the insertion set ready to install, the user can then place proximal end 17 (which can also be referred to as the "bottom" of the insertion device) over the installation site and actuate both release elements 25 simultaneously to uncouple the insertion set from the device and allow driver 30 to advance the insertion set to an advanced position that installs the insertion set to the user. The insertion needle and cannula of the insertion set will be positioned below the surface of the user's skin as a result. The release elements can be released, the insertion device removed, and then the user can remove the insertion needle from the remainder of the insertion set.

Figure 1:
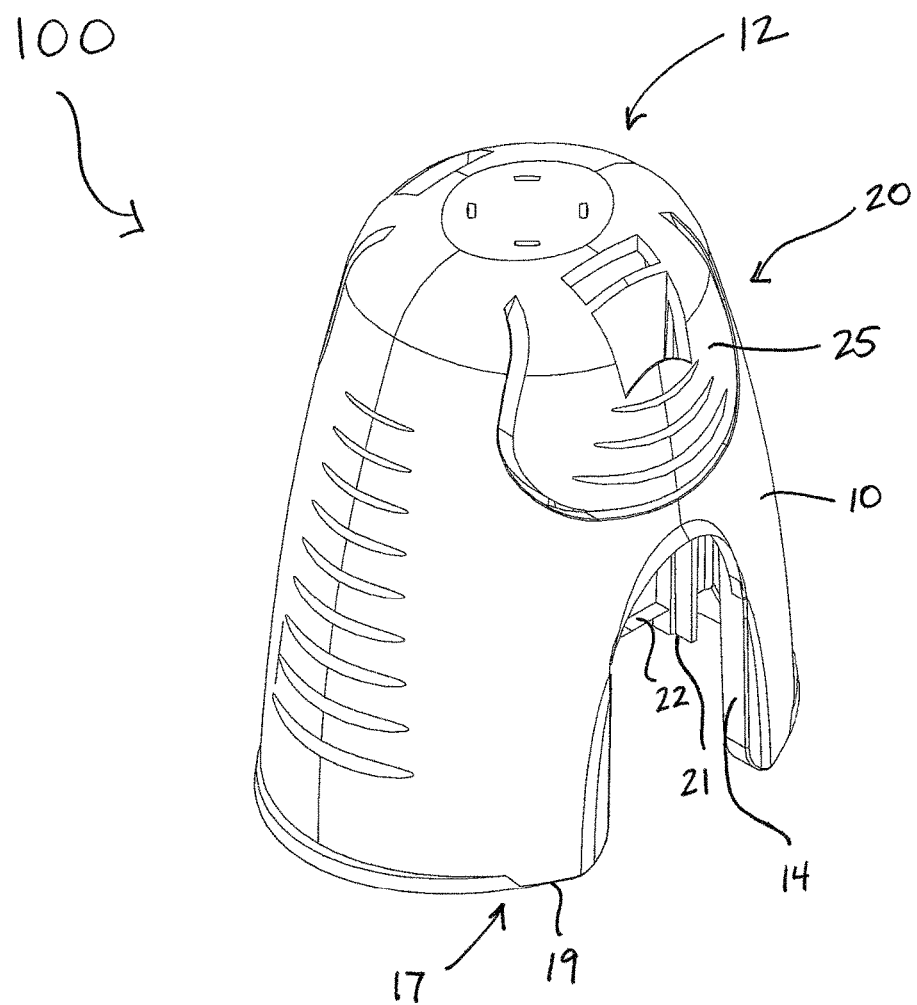
Figure 2:
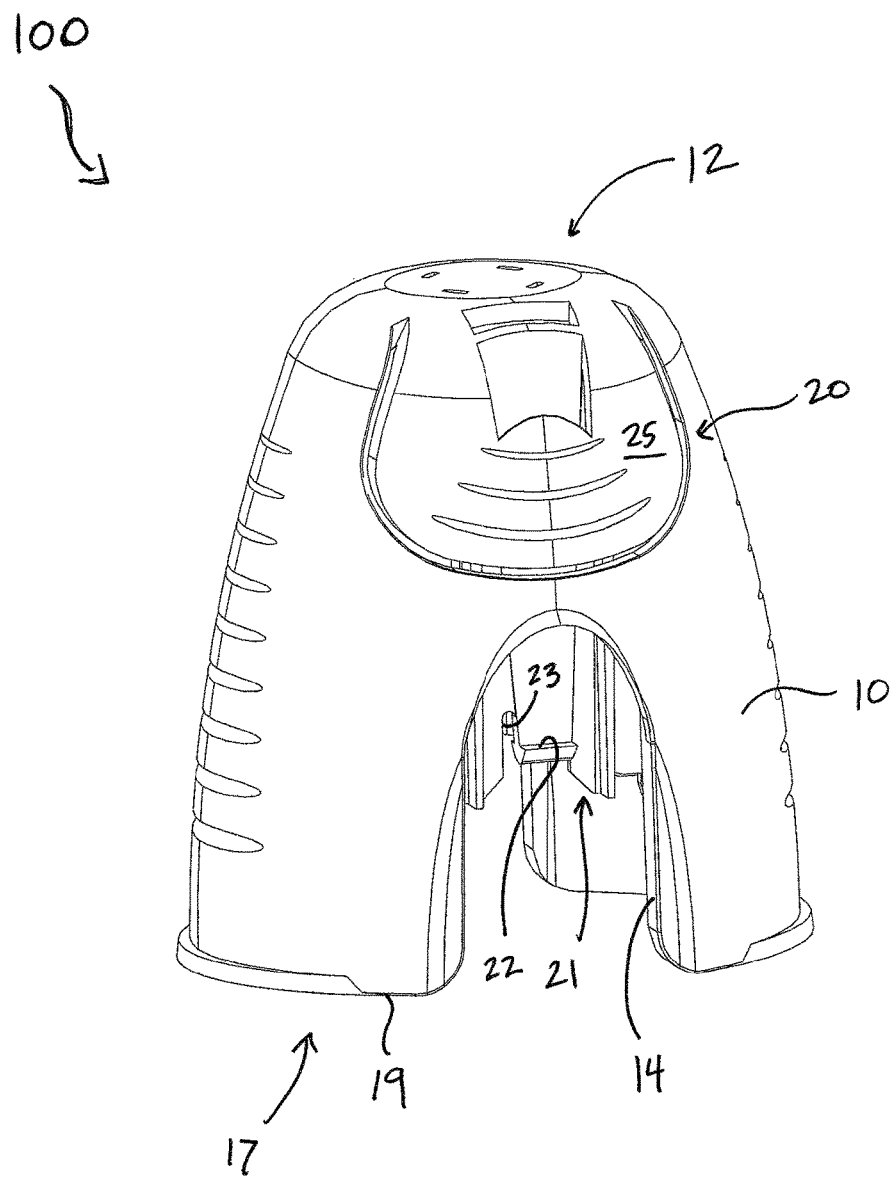
Figure 3:
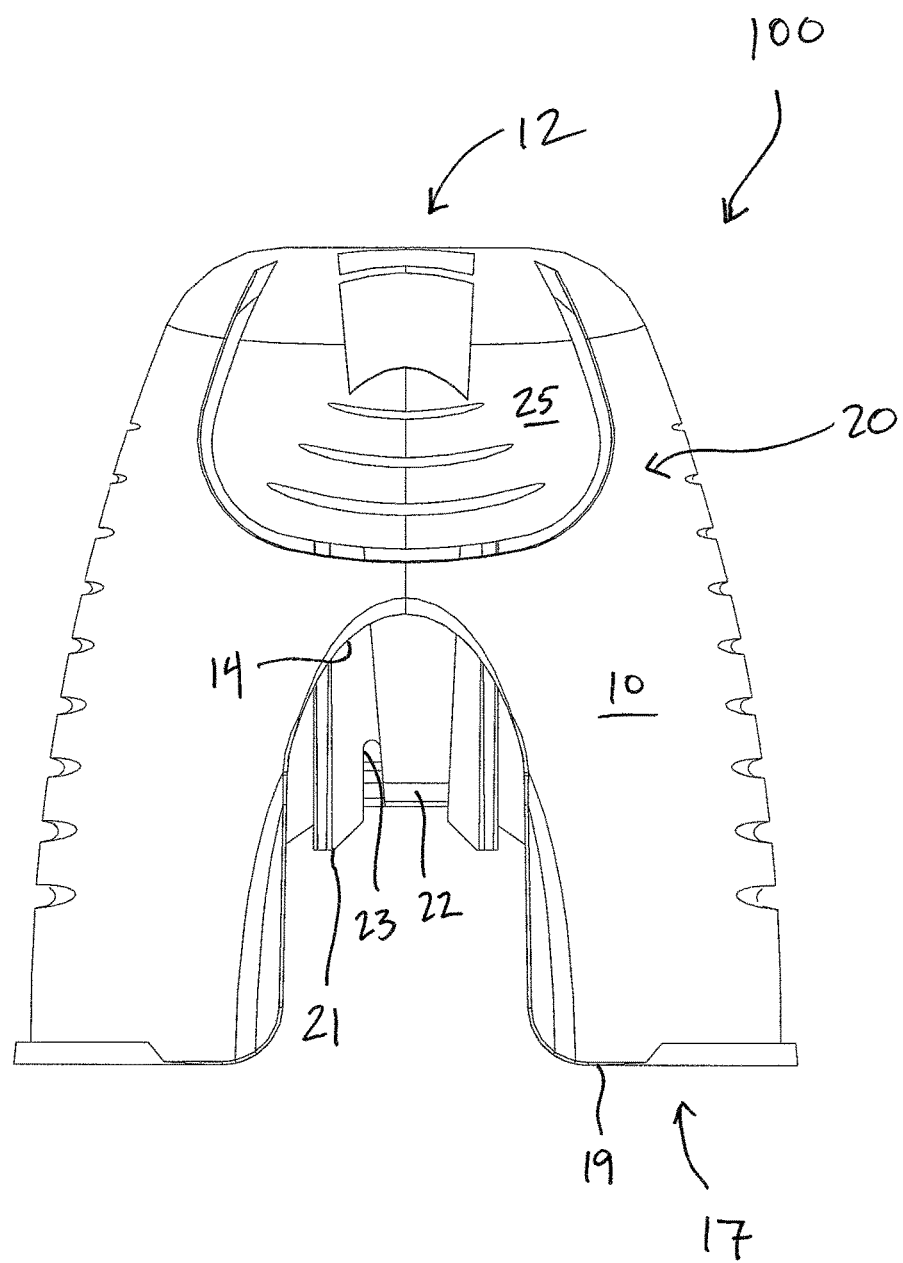
Figure 4:
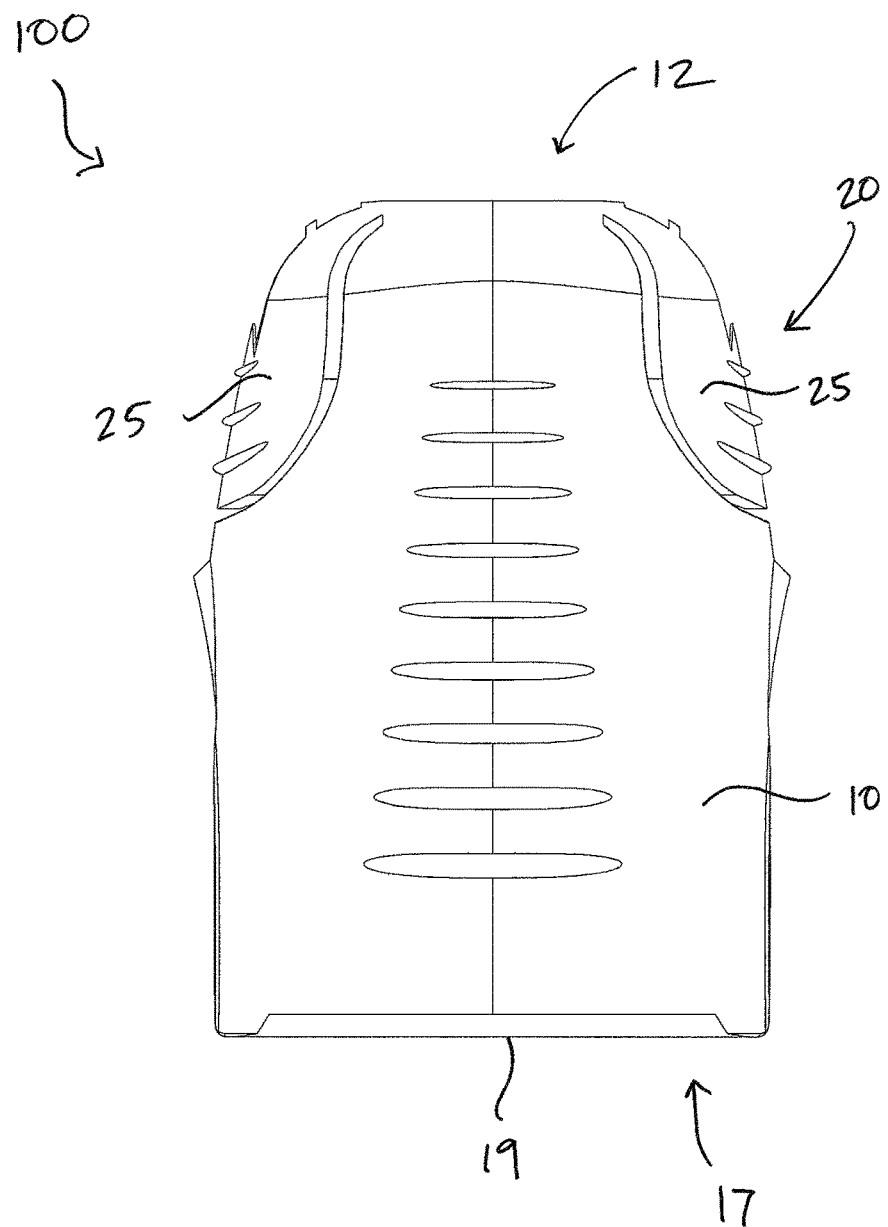
Figure 5:
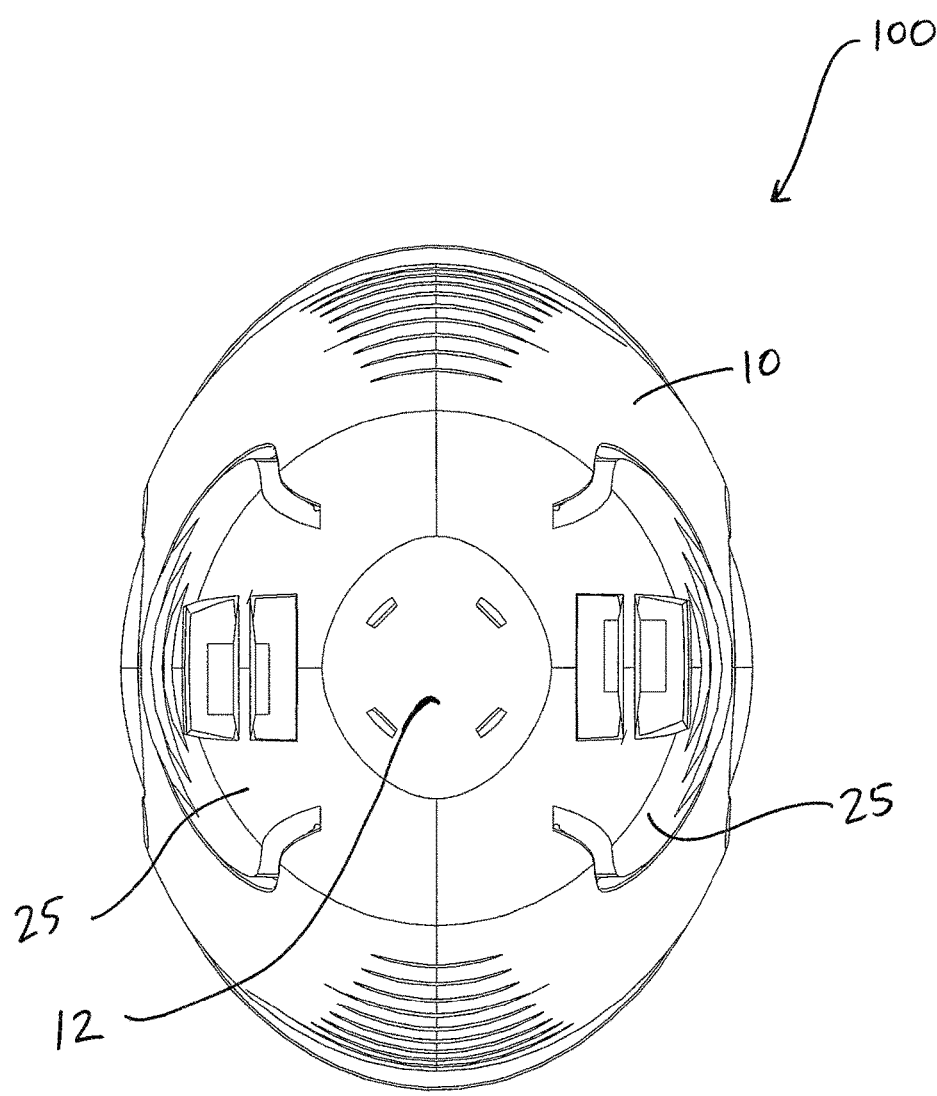
Figure 6:
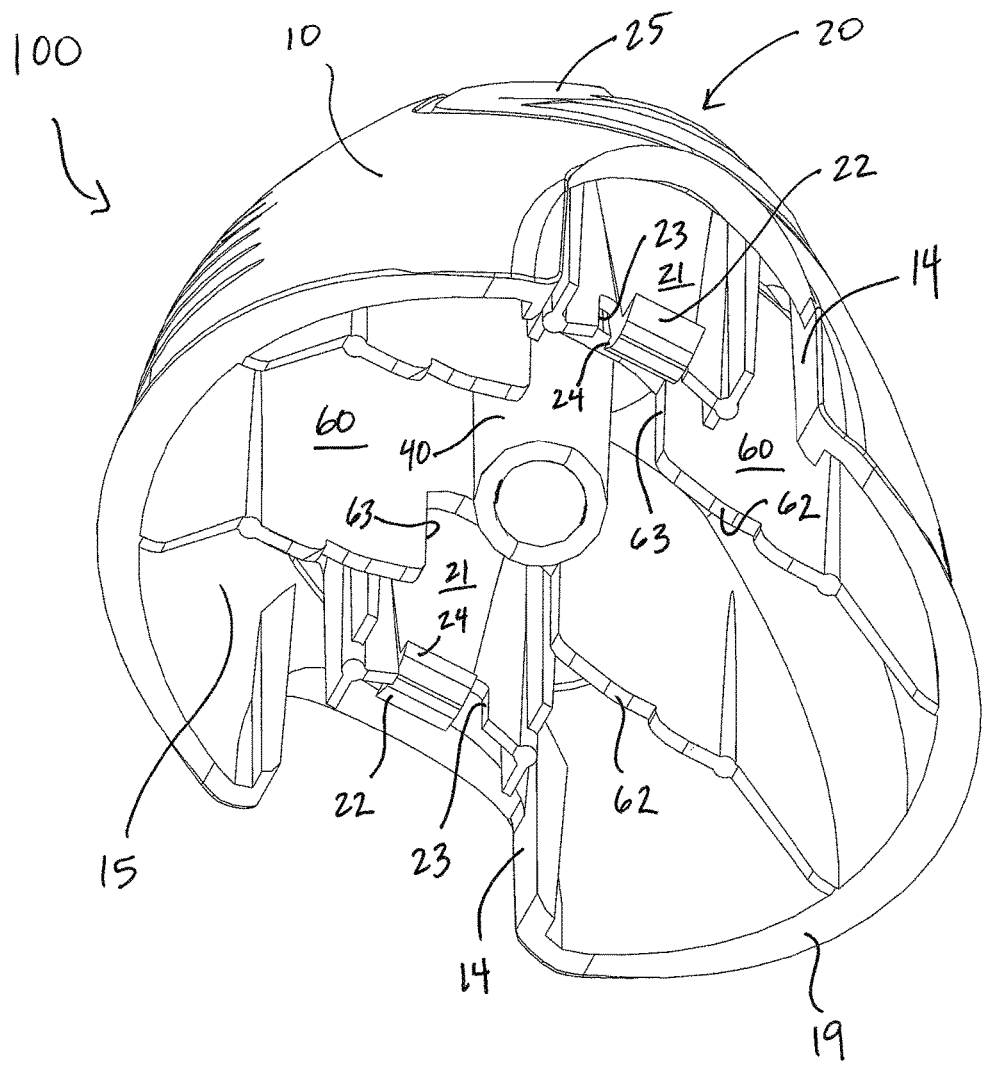

Driver 30 is configured not to break the plane of the top end of insertion needle hub 50. Instead, it rests against the top surface of insertion needle hub 50 when the insertion set of which insertion needle hub 50 is a part is coupled to insertion device 100 (and, more specifically, to housing 10 of the device) and in a pre-installed position. Further, insertion device 100 is configured (by virtue, for example, of the configurations of housing 10, the retention mechanism, and driver 30) such that if an insertion set is coupled to insertion device 100 and that insertion set is in a pre-installed position, driver 30 will apply a force to the insertion set in the direction of proximal end 17 (or, in the direction of the user, if the insertion device is positioned against the user's skin). In contrast, when the driver of inserter 10 shown in FIG. 1A of U.S. Pat. No. 7,056,302 is in a constrained position and insertion set 14 is in its pre-installed position, there is no force applied to insertion set 14 by the driver. Also in contrast, when infusion set 30 shown in FIG. 1 of US 2006/0135908 is in the pre-installed position shown in that figure, the driver of displacement mechanism 4 does not apply a force to infusion set 30. The force driver 30 will apply to the insertion set in its pre-installed position will be opposed by a force applied to the insertion set by another portion of insertion device 100, specifically (in the depicted embodiment) the portion (e.g., the retention mechanism, and more specifically retention elements 21) of the insertion device to which the insertion set is directly coupled.

Figure 20:
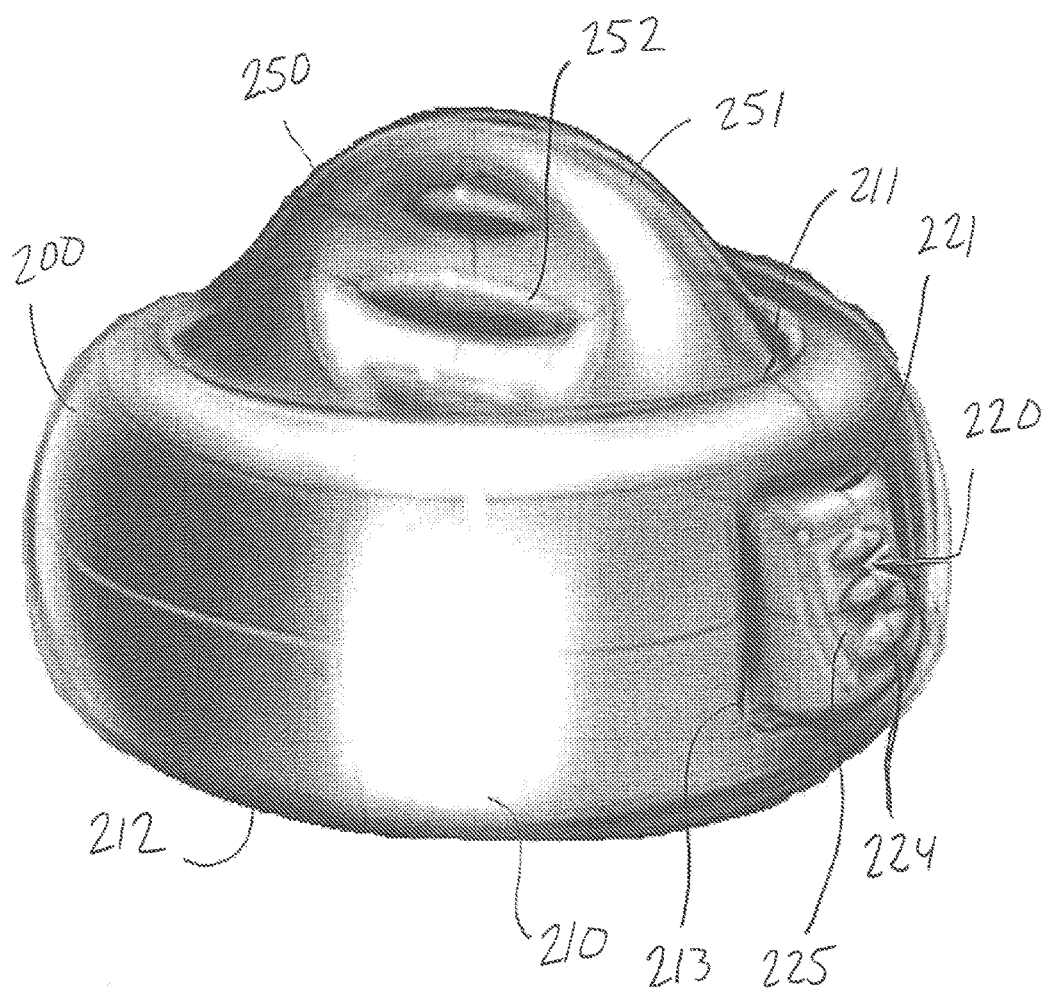
FIG. 20 is a perspective view of one embodiment of the present insertion devices loaded with an insertion set.
Figure 21:
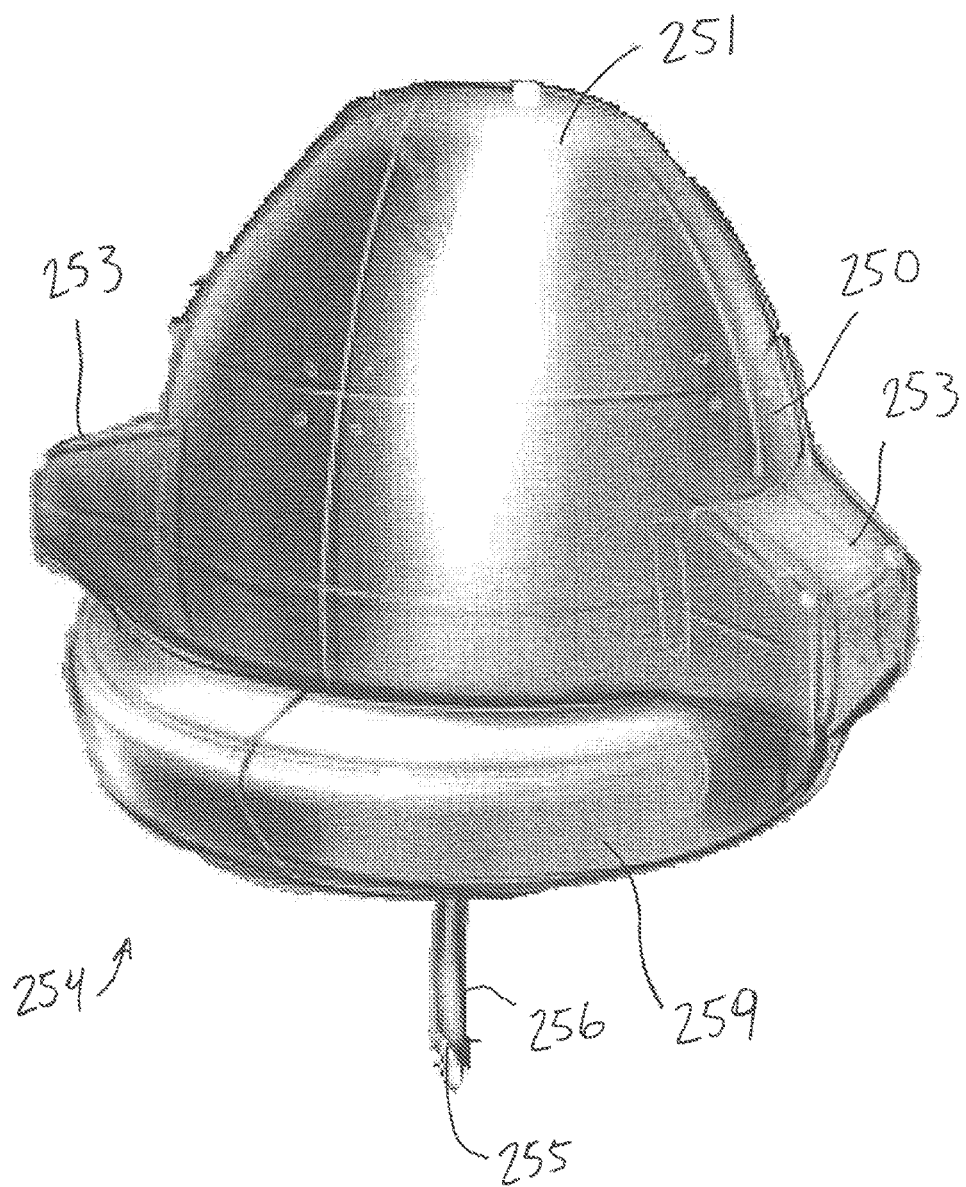
FIG. 21 is a perspective view of one embodiment of an insertion set that can be loaded into the insertion device shown in FIG. 20.
Figure 22:
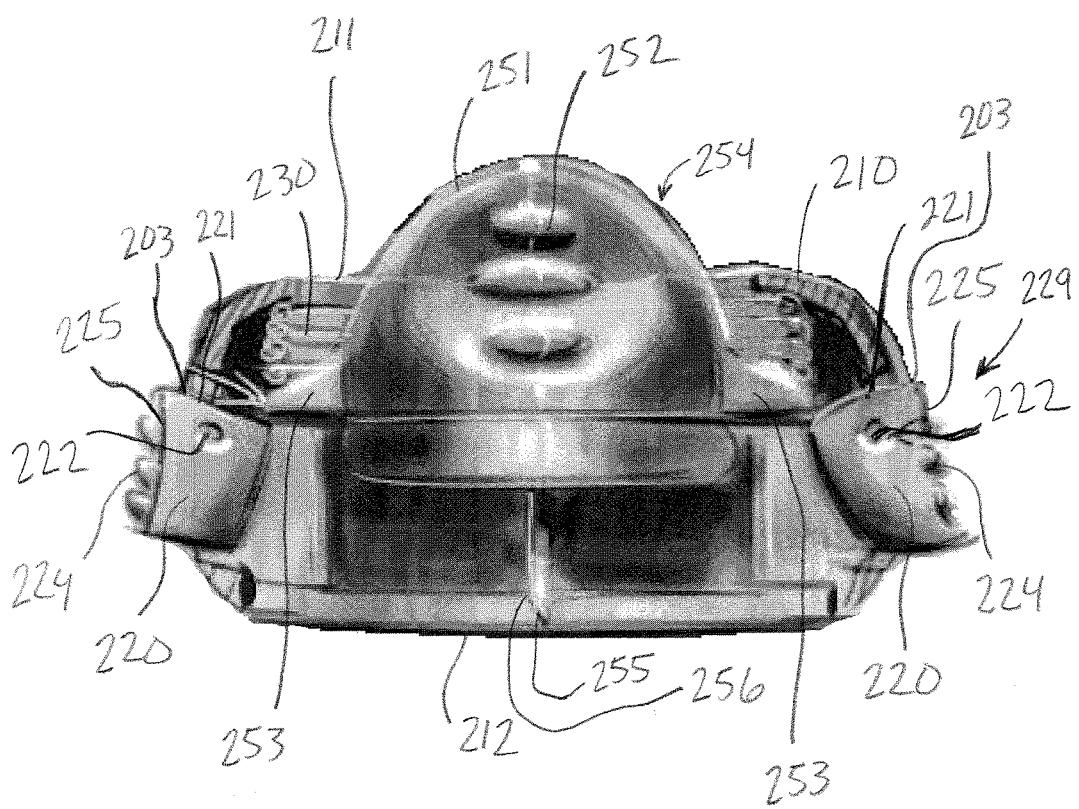
FIG. 22 is a partial cross-sectional view of the loaded insertion device shown in FIG. 20.

Referring now to FIGS. 20-22, another embodiment of the present insertion devices is shown. Insertion device 200 includes a housing 210 with a distal or upper aperture 211, a proximal or lower aperture 212, and a pair of lateral apertures 213. Insertion device 200 also includes a driver 230 that is coupled to the housing, and an insertion set retention mechanism 229 that is coupled to the housing and that comprises a pair of insertion set retention elements 220 that extend through lateral apertures 213. Each insertion set retention element 220 includes a release surface 225 (on the outer portion of insertion set retention element 220) and a retention surface 221 (on the upper portion of insertion set retention element 220). Release surface 225 may include gripping elements 224. In the depicted embodiment, insertion set retention elements 220 are coupled to housing 210 via a pair of pivot pins 222. In the embodiment shown, insertion set retention elements 220 rotate about a pair of pivot pins 222 through which they are coupled to housing 210. In other embodiments, insertion set retention elements 220 may be coupled in other ways, including, for example, through the use of hinges.

FIG. 22 shows insertion device 200 loaded with an insertion set 254 in a pre-installed position. As shown in FIGS. 21 and 22, insertion set 254 includes an insertion needle 255 connected to an insertion needle hub 250 having an upper portion 251 and a pair of lateral extensions 253. Insertion set 254 also includes a base 259, which is coupled to the insertion needle and from which cannula 256 extends as shown in FIGS. 21 and 22. Needle hub 250 may comprise optional gripping elements 252 that enhance the installability of insertion set 254 without the aid of one of the present insertion devices, such as insertion device 200. In certain embodiments, gripping elements 252 are laterally-oriented ridges (meaning the ridges are oriented normal to the axis of the needle) and are centrally aligned with needle 255 to reduce the likelihood that insertion device 254 becomes inadvertently rotated or twisted in the installer's grip during installation without an insertion device.

Insertion device 200 can be loaded by placing insertion set 254 in housing 210 and directing upper portion 251 through lower aperture 212 and upper aperture 211. A user may grip upper portion 251 and pull it so that lateral extensions 253 move past insertion set retention elements 220 and compress driver 230, which in this embodiment takes the form of a spring. As needle hub 250 moves towards upper aperture 211, lateral extensions 253 contact insertion set retention elements 220 and cause insertion set retention elements 220 to pivot or rotate outwardly about pivot pins 222 (e.g., the insertion set retention element on the left side of FIG. 22 pivots counterclockwise and the right insertion set retention element pivots clockwise). This allows lateral extensions 253 to move past insertion set retention elements 220. When lateral extensions 253 are located above insertion set retention elements 220 (e.g., in the area between insertion set retention elements 220 and upper aperture 211), a user may release upper portion 251. Driver 230 will then exert a force on lateral extensions 253 and cause lateral extensions 253 to engage the interior portions of retention surfaces 221 (which are the portions of the retention surfaces 221 that are on the inside of the pivot pins 222 toward the center of the housing). The force exerted on the interior portions of retention surfaces 221 will cause insertion set retention elements 220 to pivot about pivot pins 222 so that the exterior portions of retention surfaces 221 (which are the portions of the retention surfaces 221 that are on the outside of the pivot pins 222 away from the center of the housing) engage housing 210 at locations 203.

As shown in FIG. 22, when insertion device 200 is in this pre-installed position, insertion set 254 will be retained by the insertion device such that the insertion needle does not break the plane defined by the proximal end (and in some cases by the proximal aperture) and needle hub 250 extends through distal aperture 211.

A user can install insertion set 254 by placing lower aperture 212 over the desired placement area and manipulating release surfaces 225 of insertion set retention elements 220. In the embodiment shown, a user can push in on the lower portion of release surfaces 225 (e.g., the portions that are below pivot pins 222) so that insertion set retention elements 220 rotate about pivot pins 222. The outward rotation of insertion set retention elements 220 will initially cause lateral extensions 253 to move upward toward aperture 211. This movement will further compress driver 230 and cause it to initially increase the force exerted on lateral extensions 253 when insertion set retention elements 220 are manipulated in the described manner.

Further rotation of insertion set retention elements 220 will also cause release surfaces 221 to pivot outwardly (e.g., with the interior portions pivoting away from the placement area and the exterior portions pivoting toward the placement area) so that they are no longer engaged with lateral extensions 253. Driver 230 can then expand, directing needle hub 250 (and therefore insertion set 254) toward lower aperture 212. Insertion needle 255 and cannula 256 of insertion set 254 will then penetrate the surface of the user's skin (not shown), leaving the insertion set 254 in an installed position.

Referring now to FIGS. 23-27, another embodiment of the present insertion devices is shown that operates in generally the same manner as the embodiment shown in FIGS. 20-22. Unless otherwise noted, elements of the embodiment in FIGS. 23-27 that are similar to elements of the embodiment in FIGS. 20-22 are given similar reference numbers in the Figures (e.g. "3xx" in FIGS. 23-27 and "2xx" in FIGS. 20-22). For the sake of brevity, a description of similar operating principles and elements will not be repeated.

In the embodiments shown in FIGS. 23-27, insertion device 300 includes a housing 310 with a distal or upper aperture 311, a proximal or lower aperture 312, and a pair of lateral apertures 313. Insertion device 300 also includes a driver 330 that is coupled to housing 310, and an insertion set retention mechanism 329 that is coupled to housing 310 and comprises a pair of insertion set retention elements 320 that extend through lateral apertures 313. In the embodiment shown, insertion set retention elements 320 rotate about a pair of pivot pins (not visible in the figures) through which they are coupled to housing 310. Each insertion set retention element 320 includes a release surface 325 (on the outer portion of insertion set retention element 320) and a retention surface 321 (on the upper portion of insertion set retention element 320). Release surface 325 may include gripping elements 324.

Figure 23:
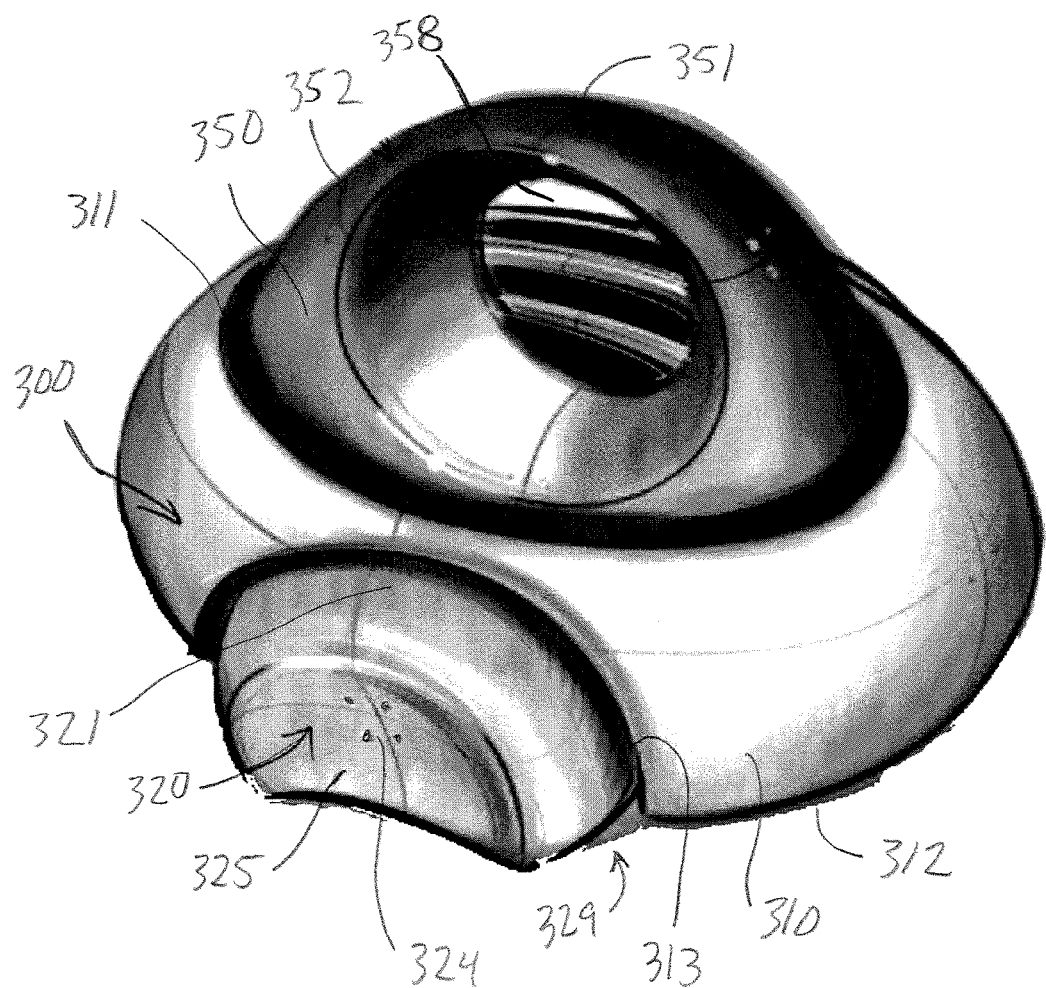
FIG. 23 is a perspective view of one embodiment of the present insertion devices loaded with an insertion set.
Figure 24:
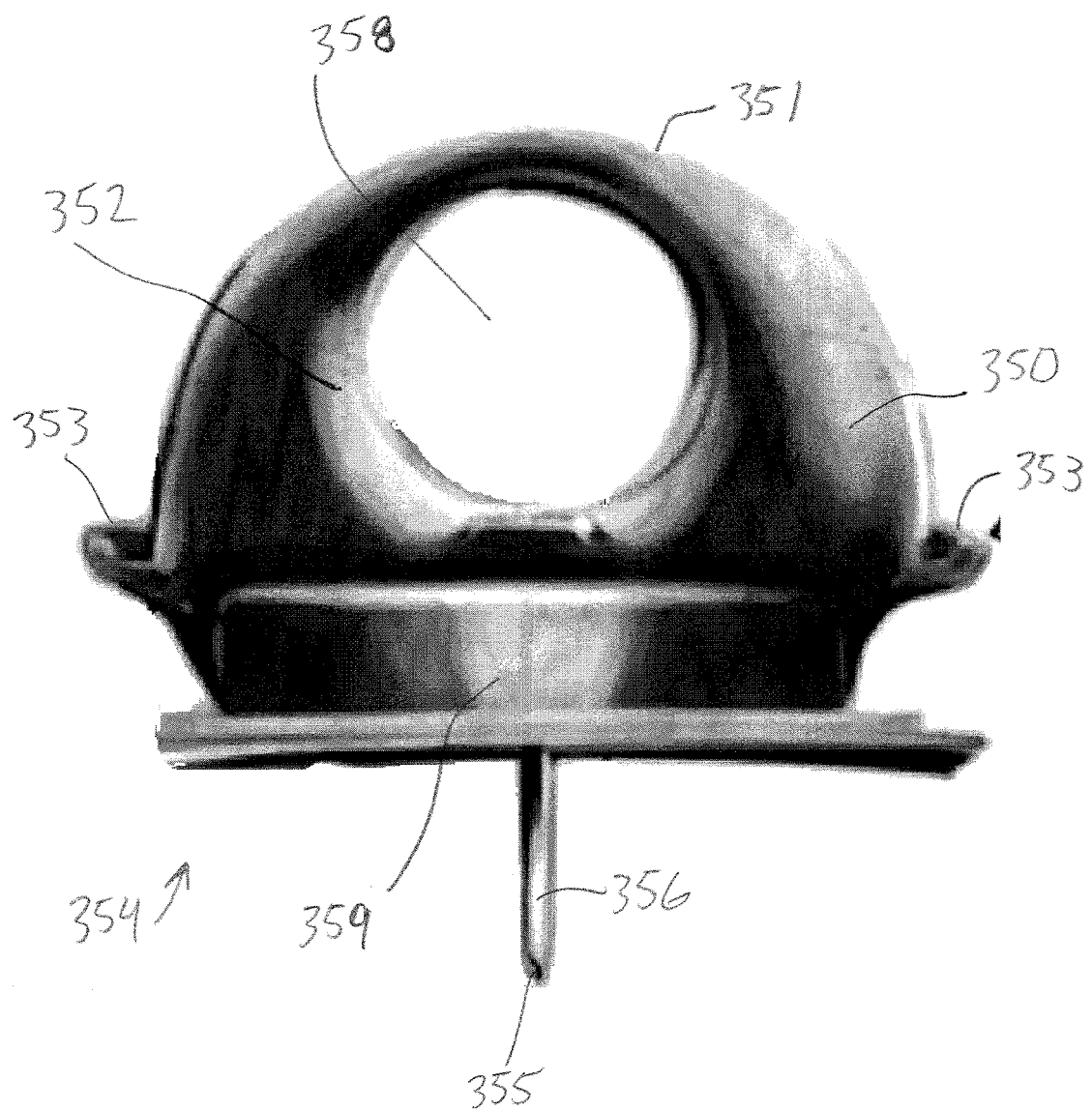
FIG. 24 is a front view of one embodiment of an insertion set that can be loaded into the insertion device shown in FIG. 23.
Figure 25:
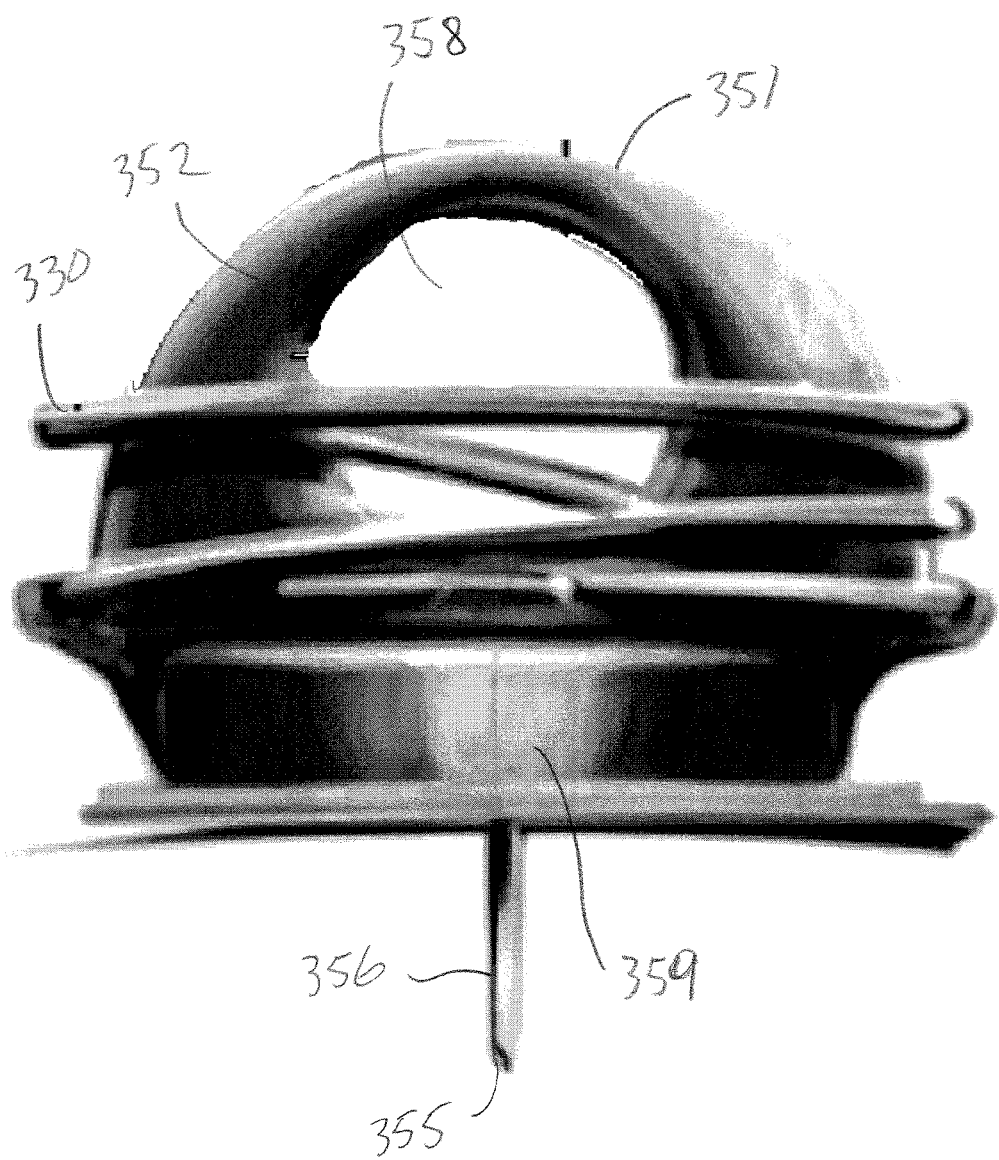
FIG. 25 shows how the driver of the insertion device shown in FIG. 23 contacts the insertion set shown in FIG. 24.
Figure 26:
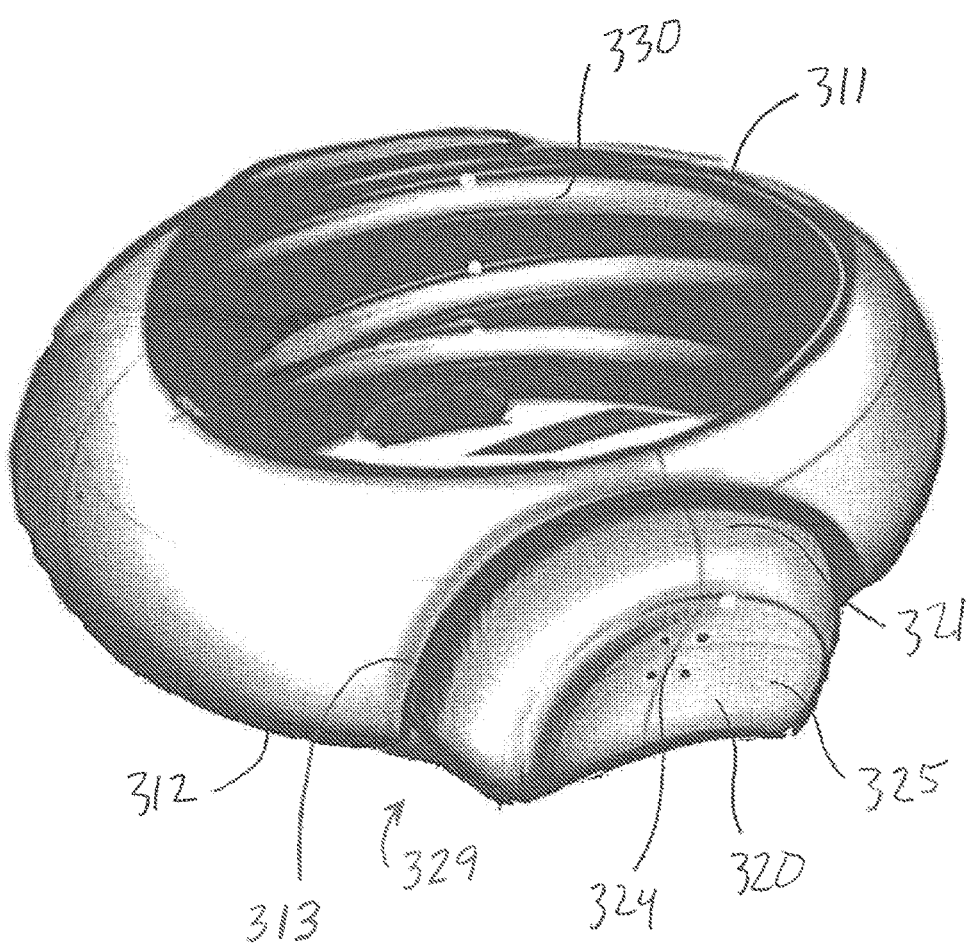
FIG. 26 is a perspective view of the insertion device shown in FIG. 23.
Figure 27:
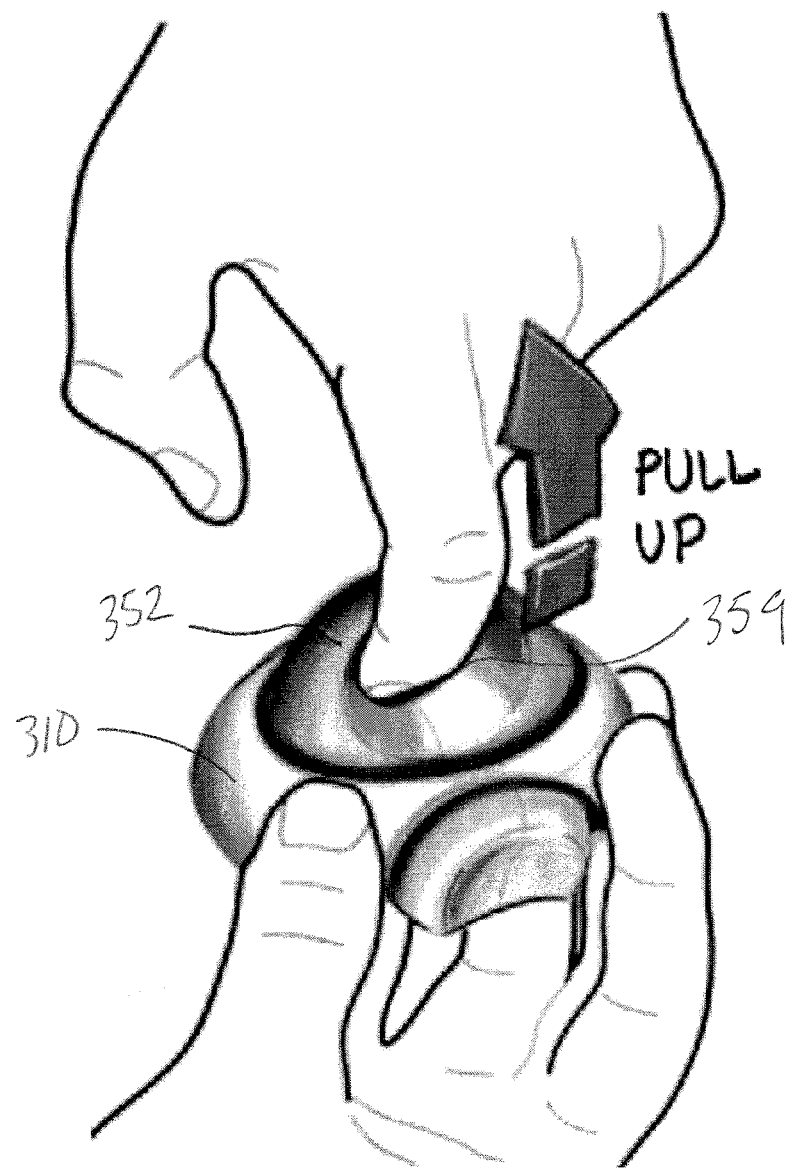
FIG. 27 is a perspective view showing how to load the insertion device shown in FIG. 23 with the insertion set shown in FIG. 24.
Figure 28:
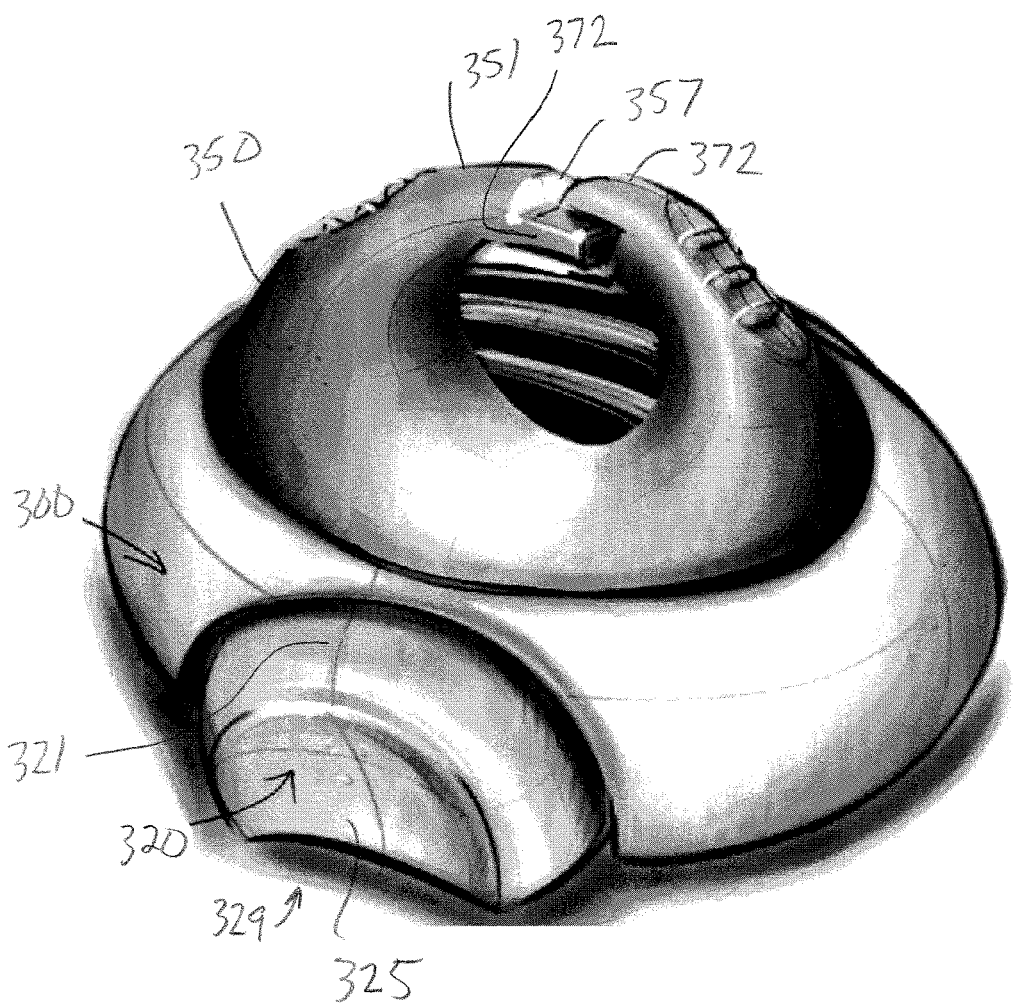
FIG. 28 is a perspective view of the insertion device shown in FIG. 23 loaded with another insertion set.
Figure 29:
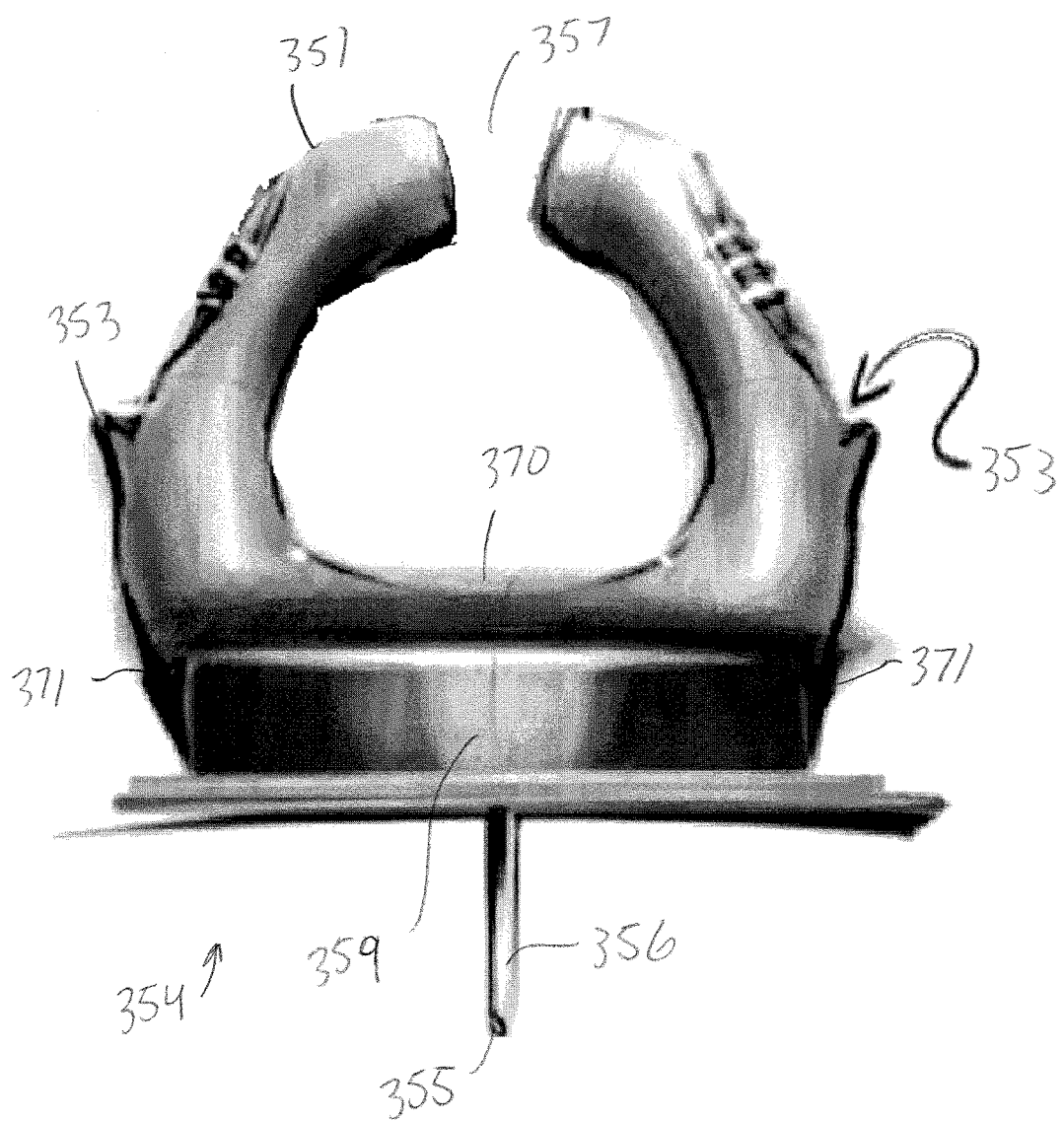
FIG. 29 is a front view of one embodiment of an insertion set with a split needle hub that can be loaded into the insertion device shown in FIG. 23.
Figure 30:
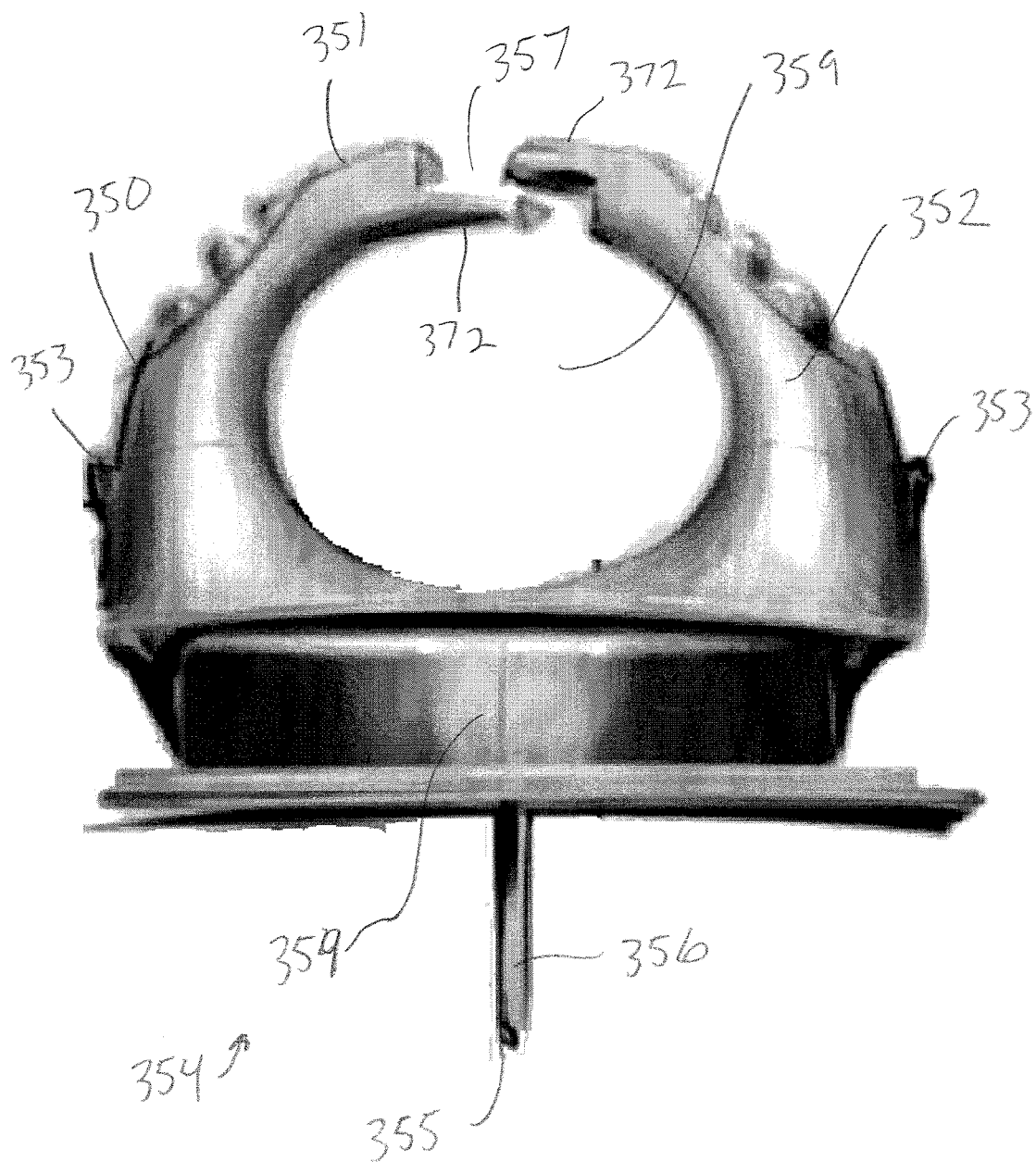
FIG. 30 is a front view of the insertion set shown in FIG. 28.

FIG. 23 shows insertion device 300 loaded with an insertion set 354 in a pre-installed position. As shown in FIGS. 24 and 25, needle hub 350 of insertion set 354 comprises an upper portion 351 and a pair of lateral extensions 353. The lateral extensions can be configured in any suitable fashion that allows them to "catch" on the inner portions of retention surfaces 321, in a manner similar to how lateral extensions 253 and retention surfaces 221 contact each other when insertion device 200 has insertion set 254 retained in a loaded, pre-installed position. Upper portion 351 is configured with an aperture 358 sized to accept a user's finger when the insertion device is loaded with the insertion set, as shown in FIG. 27. This configuration is one version of an upper portion that comprises a pull ring portion 352. Needle hub 350 is coupled to base 359 of insertion set 354 through needle 355, with insertion set 354 being shown in a pre-installed configuration in FIGS. 24 and 25. Insertion device 300 can be loaded with insertion set 354 in a manner similar to the embodiment described in FIGS. 20-22. In the embodiment shown in FIGS. 23-27, however, a user may place a finger in aperture 359 and pull needle hub 350 through aperture 311 (as shown in FIG. 27). After insertion device 300 is loaded, a user may operate it in a manner similar to that described in the discussion of the embodiment in FIGS. 20-22. Specifically, a user may press on release surfaces 325 to release needle hub 350 and, more generally, insertion set 354 from being secured by the insertion set retention mechanism, and allow insertion set 354 to be installed to a user.

Figure 31:
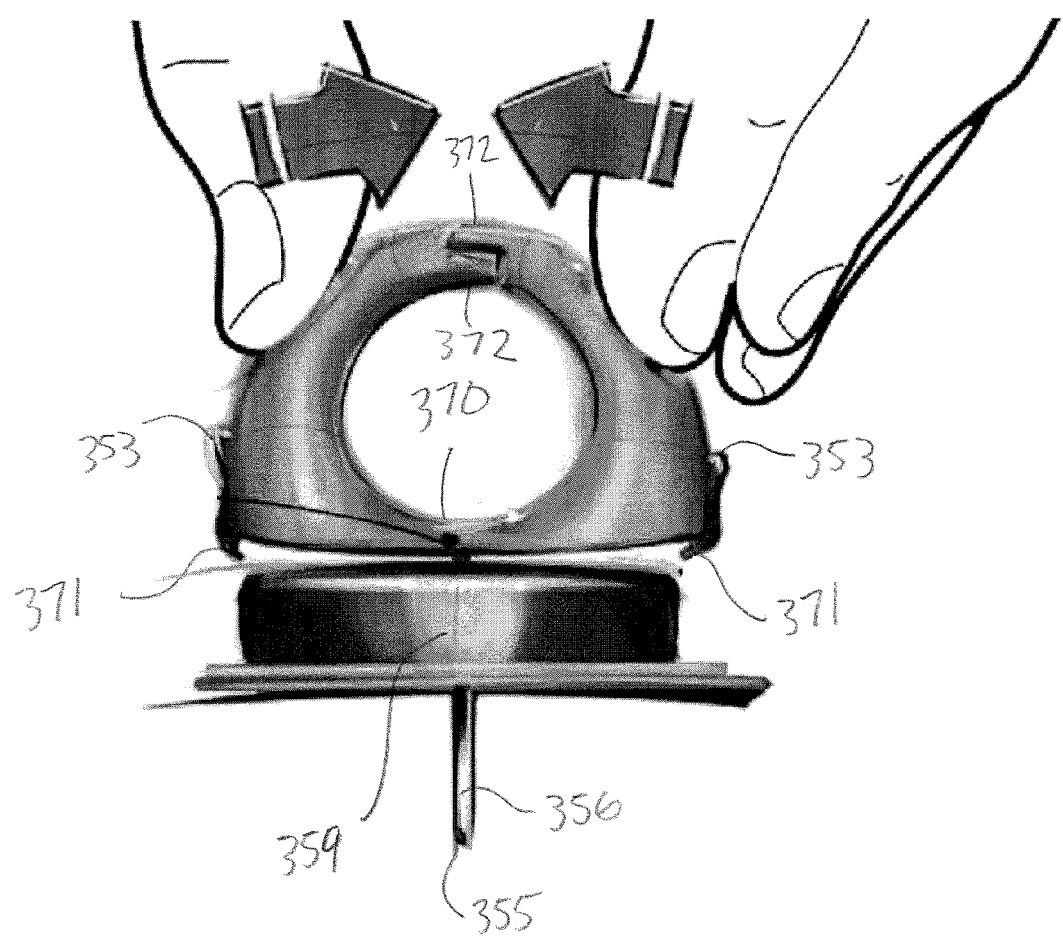
FIG. 31 shows a user manipulating the needle hub of the FIG. 28 insertion set to facilitate the separation of the hub from the base of the insertion set.

FIGS. 28-31 illustrate alternative embodiments of needle hub 350 that incorporate a split 357 in the upper portion 351 of needle hub 350. In one embodiment (shown in FIGS. 28, 30 and 31) needle hub 350 comprises a pair of extensions 372 on either side of split 357 (as shown in FIG. 31). Those extensions are not part of the FIG. 29 embodiment. As shown in FIG. 31, needle hub 350 may comprise a flexible portion 370 that allows needle hub 350 to be flexed such that the two opposing prongs shown in these embodiments can be moved toward each other to close the gap of split 357. Needle hub 350 may also comprise two base retention members 371. Base retention members 371 may be configured in some embodiments to extend inwardly, as shown in FIG. 31, and engage a groove in base 359 (not shown) to increase the separation force required to separate base 359 from the insertion needle after installation (though the friction between the septum insertion set and the needle will normally provide a sufficient holding force to keep the two together). In other embodiments, base retention members 371 may be configured to interfere with opposing portions of the outer wall of base 359 of insertion set 354 so as to increase the friction between the base and the needle hub. Squeezing or otherwise moving together the opposing prongs of needle hub 350 that are separated by the gap of split 357 (as shown in FIG. 31) may help separate base retention members 371 from base 359 after installation and during the removal of the insertion needle from the base. In other respects, the embodiments of the insertion sets shown in FIGS. 28-31 are configured (and, more specifically, the needle hubs of these insertion sets are configured) such that insertion device 300 can load them and retain them in a pre-installed position in a similar manner to the insertion set shown in FIGS. 23-27.

Figure 32:
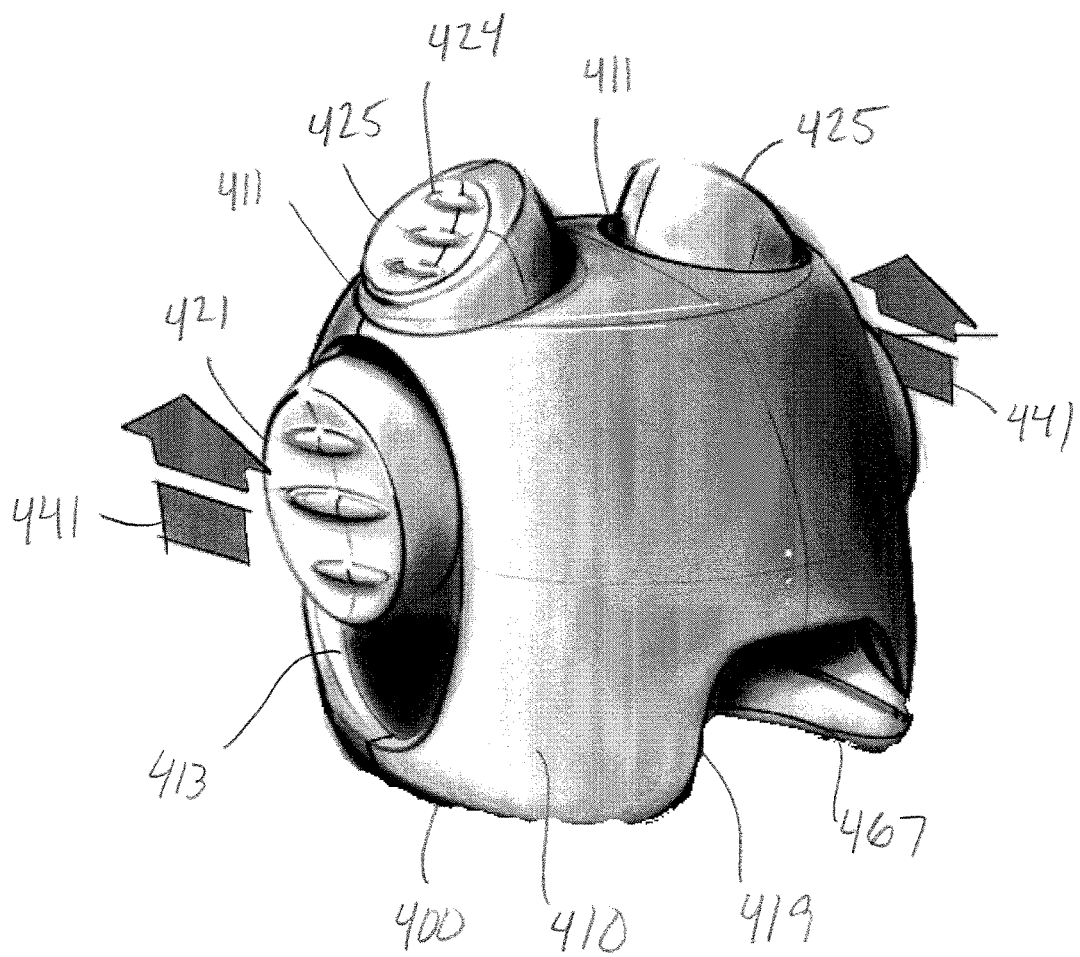
FIG. 32 is a perspective view of one embodiment of the present insertion devices loaded with an insertion set.
Figure 33:
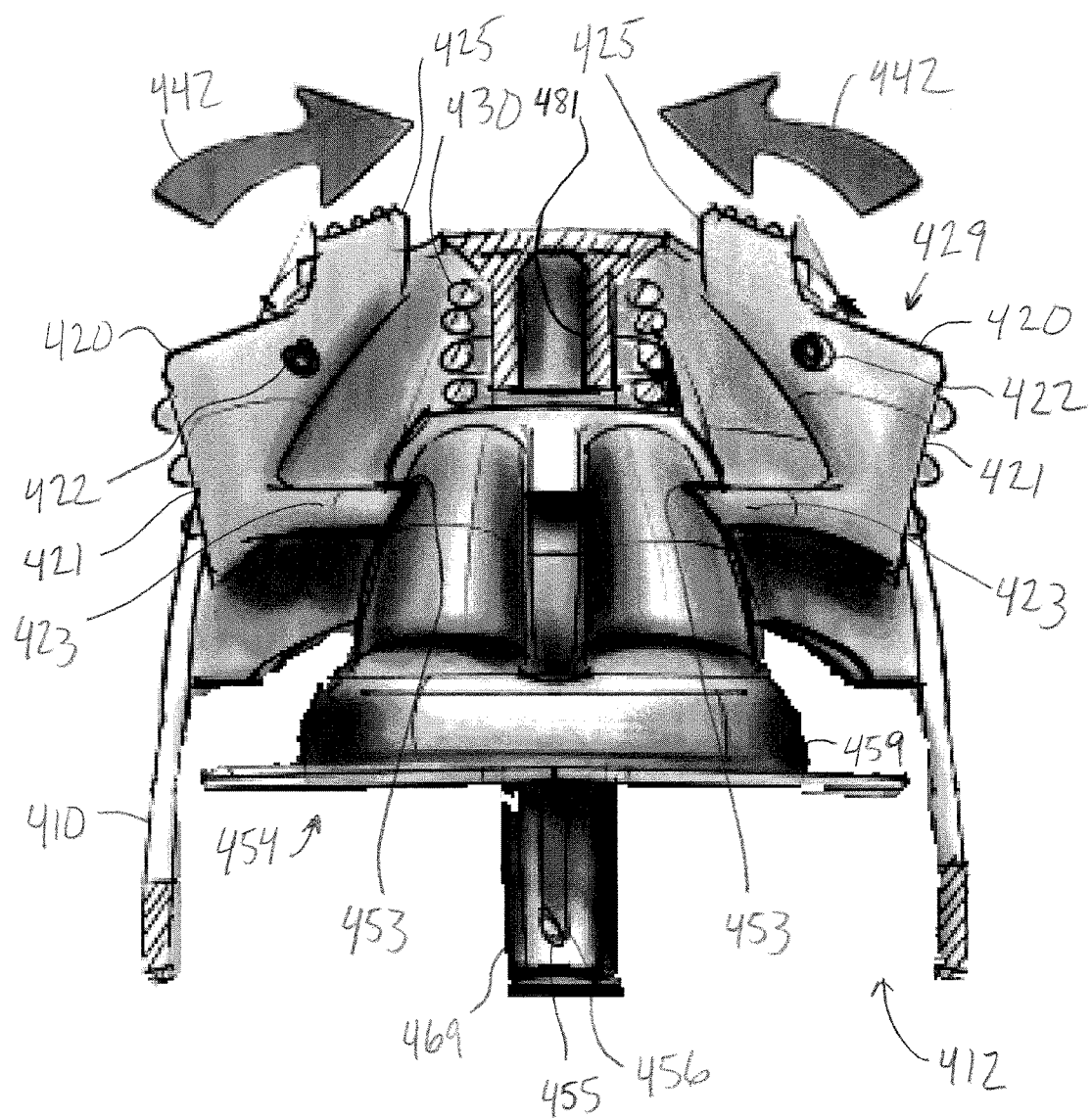
FIG. 33 is a partial cross-sectional view of the loaded insertion device shown in FIG. 32.
Figure 34:
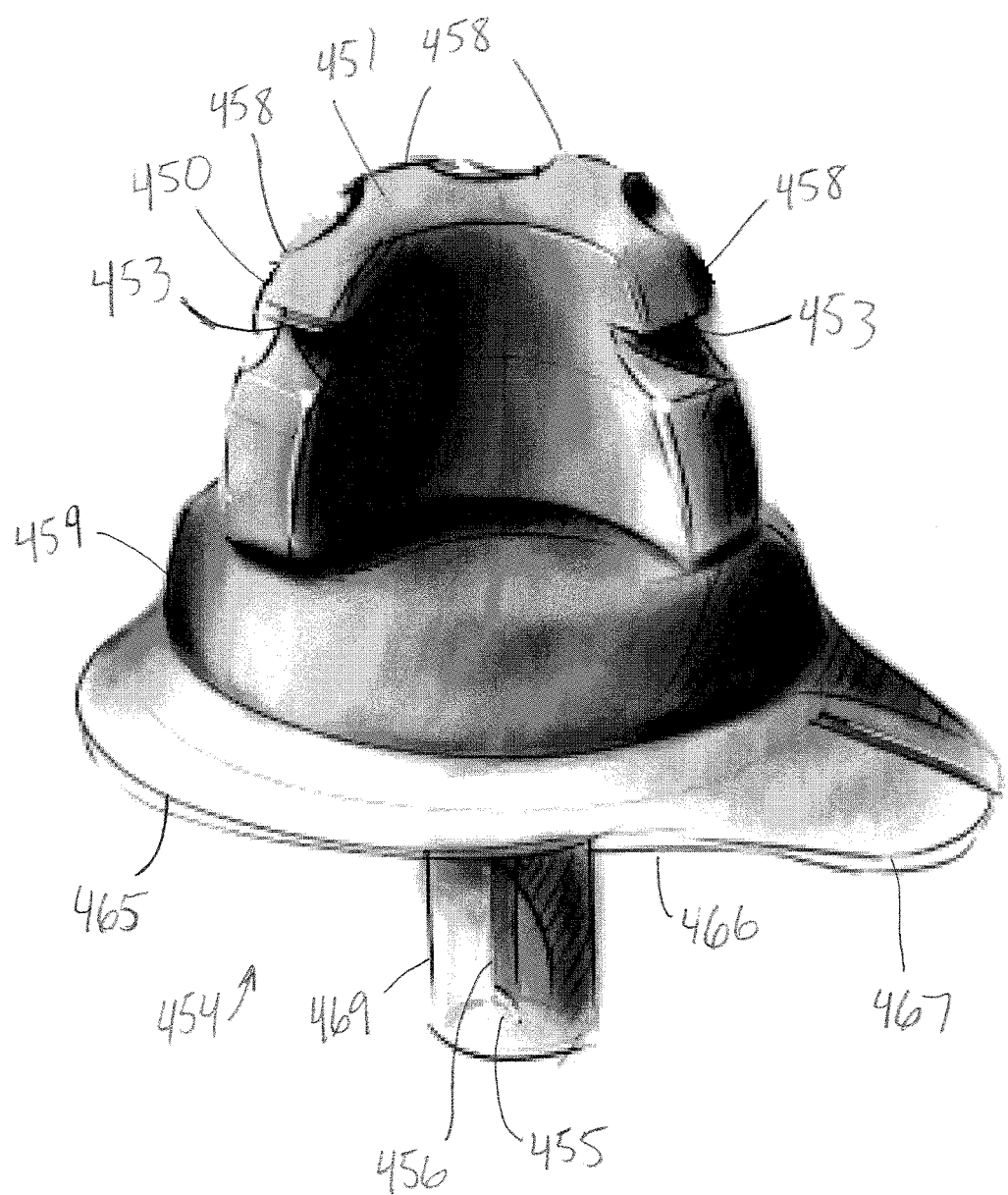
FIG. 34 is a perspective view of the insertion set shown in FIG. 33.

Referring now to FIGS. 32-34, another embodiment of the present insertion devices is shown that operates in generally the same manner as the embodiment shown in FIGS. 23-27. Insertion device 400 comprises a housing 410 with a pair of distal or upper apertures 411, a proximal or lower aperture 412, and a pair of lateral apertures 413. Insertion device 400 also includes a driver 430 that is coupled to housing 410, and an insertion set retention mechanism 429 that is coupled to housing 410 and that comprises a pair of insertion set retention elements 420 that extend through lateral apertures 413. Each insertion set retention element 420 includes a release element 425 (on the upper portion of insertion set retention element 420) and a gripping element 421 (on the outer portion of insertion set retention element 420). Release element 425 may include gripping members (e.g., ridges) 424. In the depicted embodiment, insertion set retention elements 420 are slidably coupled to housing 410 via a pair of pivot pins 422. In the embodiment shown, insertion set retention elements 420 rotate about a pair of pivot pins 422 through which they are coupled to housing 410. Housing 410 may be configured with side wall portions that include slots into which the pivot pin ends extend (in some embodiments, the slots may extend through the housing; in other embodiments, the slots may not). The pivot pins may be configured (for example, with an internal spring) so that their overall length can be compressed during the assembly process to allow insertion of the pins into the housing slots. In other embodiments, insertion set retention elements 420 may be coupled to housing 410 in other ways, including, for example, through the use of hinges.

As shown in FIGS. 32 and 33, lateral apertures 413 are larger than gripping elements 421 and allow gripping elements 421 to be moved along a portion of the length of housing 410 (e.g., in the direction from lower aperture 412 towards upper apertures 411). FIG. 33 shows insertion device 400 loaded with an insertion set 454 in a pre-installed position. As shown in FIG. 34, insertion set 454 includes an insertion needle that includes an insertion needle hub 450 having an upper portion 451 that comprises four grip members 458, each of which includes a retention notch 453, though as few as two retention notches may be used. In this embodiment, a user may insert insertion set 454 into lower aperture 412. Insertion device 400 is configured such that driver 430 will move from an unloaded position to a loaded position when insertion set retention mechanism 429 is actuated in a first manner. For example, with insertion set retention elements 420 placed towards the bottom of apertures 413, a user can squeeze (or otherwise manipulate) gripping elements 421 (so that a pair of engaging portions 423 contact (e.g., engage) two of the retention notches 453. With insertion set retention elements 420 engaged with needle hub 450, a user can direct insertion set retention elements 420 (via direct manipulation of gripping elements 421) toward apertures 411 (in the directions indicated by arrows 441) until release elements 425 extend through apertures 411. This movement compresses driver 430 and loads the insertion set 454 into insertion device 400 and into a pre-installed position. Insertion devices 500 and 900, discussed below, are configured such that drivers 530 and 930 will move from unloaded positions to loaded positions when insertion set retention mechanisms 529 and 929 are actuated in a similar manner to that just described.

In the embodiment shown, insertion device 400 engages insertion set 454 through an interference fit (e.g., a snap fit) between engaging portions 423 and retention notches 453 that is sufficient to resist the force exerted on insertion set 454 by driver 430. The interference fit between engaging portions 423 and retention notches 453 can therefore maintain driver 430 in a loaded, pre-installed position until a user manipulates release elements 425 as described below.

In certain embodiments, insertion set 454 may comprise (as may all of the present insertion sets in some embodiments) an adhesive patch 465 that includes an adhesive surface that can be exposed prior to installation by removing a protective layer (e.g., a sheet) 466. A protective guard 469 (which may take the form of a rigid plastic tube) may be positioned around needle 455 and cannula 456 (as with all of the present insertion sets in some embodiments) that may be removed prior to installation.

In the embodiment shown in FIG. 32, a tab 467 of adhesive patch 465, which is designed to facilitate the removal of sheet 467 and the removal of insertion set from a user, extends through an open section 419 of housing 410. Tab 467 can be accessed to remove protective layer 466 from adhesive patch 465. After protective layer 466 has been removed, a user can place insertion device 400 at a desired installation location and move release elements 425 in the directions shown by arrows 442. This movement can allow insertion set retention elements 420 to pivot about pivot pins 422 and cause engaging portions 423 to become disengaged from retention elements 453. Driver 430, which is in contact with needle hub 450, can therefore expand and move needle hub 450 (and, more generally, insertion set 454) toward the proximal end of the housing and install the insertion set to the user. Insertion device 400 is configured such that the movement of insertion set retention mechanism 429 in the above-described manner is one example of a manner of actuating insertion set retention mechanism 429 so that driver 430 moves from a loaded position to an unloaded position. Insertion devices 500 and 900, described below, are configured in a similar manner such that movement of insertion set retention mechanisms 529 and 929 in a similar manner will move drivers 530 and 930 from a loaded position to an unloaded position. More specifically, the two movements of insertion set retention mechanism 429 described above—which move the driver from an unloaded to a loaded position, and vice-versa—are examples of movements that involve direct user contact with the insertion set retention mechanism, as is true of other similar versions of the present insertion set retention mechanisms (such as insertion set retention mechanisms 529 and 929).

Figure 35:
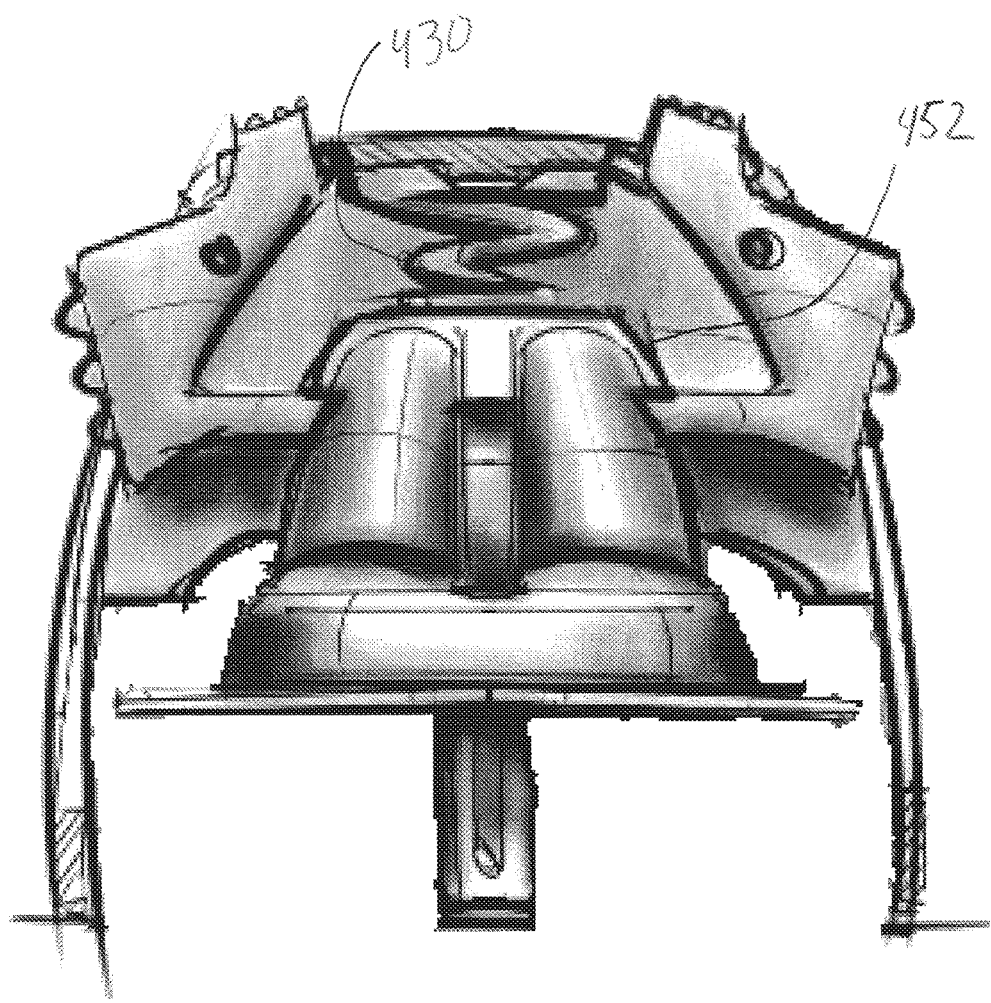
FIG. 35 is a partial cross-section view of another embodiment of the present insertion devices, similar to the one shown in FIG. 32, that is loaded with the insertion set shown in FIGS. 33 and 34.
Figure 36:
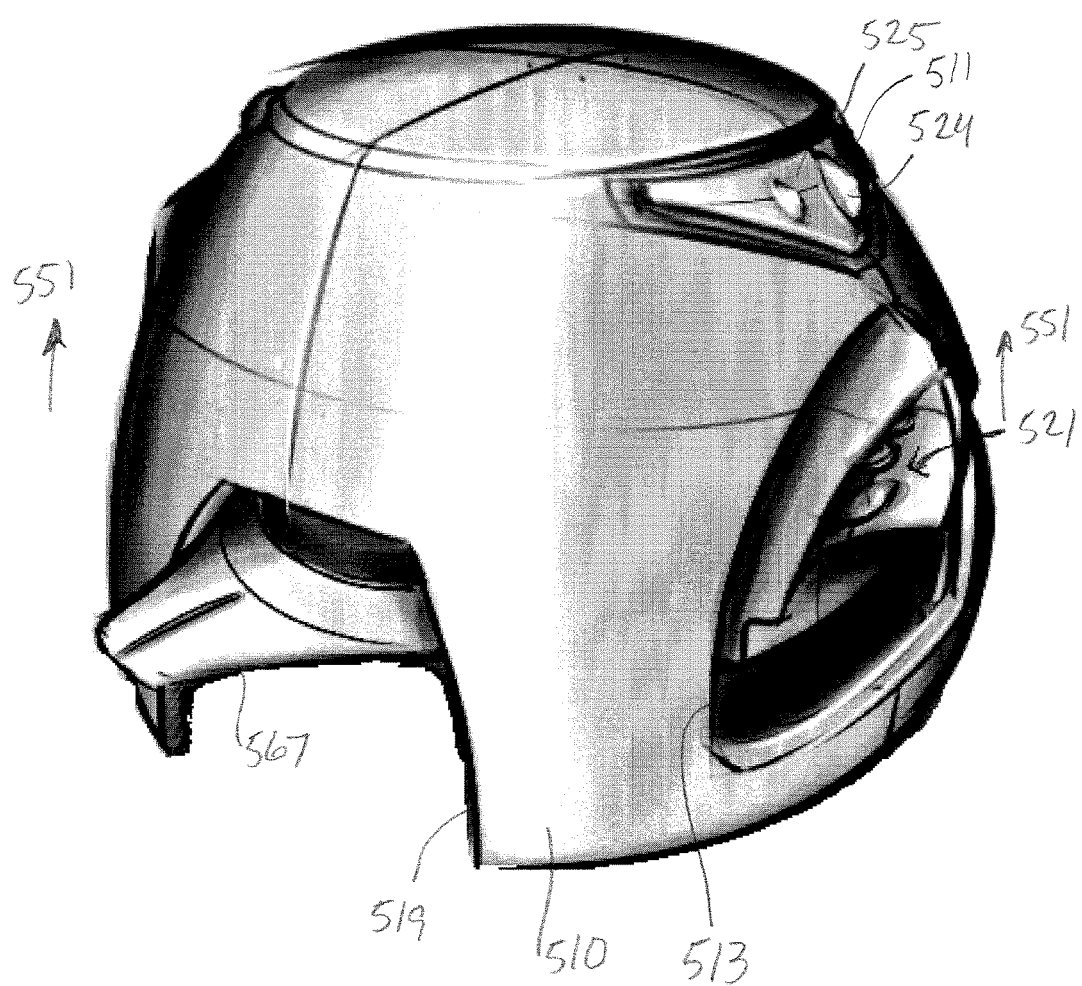
FIG. 36 is a perspective view of one embodiment of the present insertion devices loaded with an insertion set.
Figure 37:
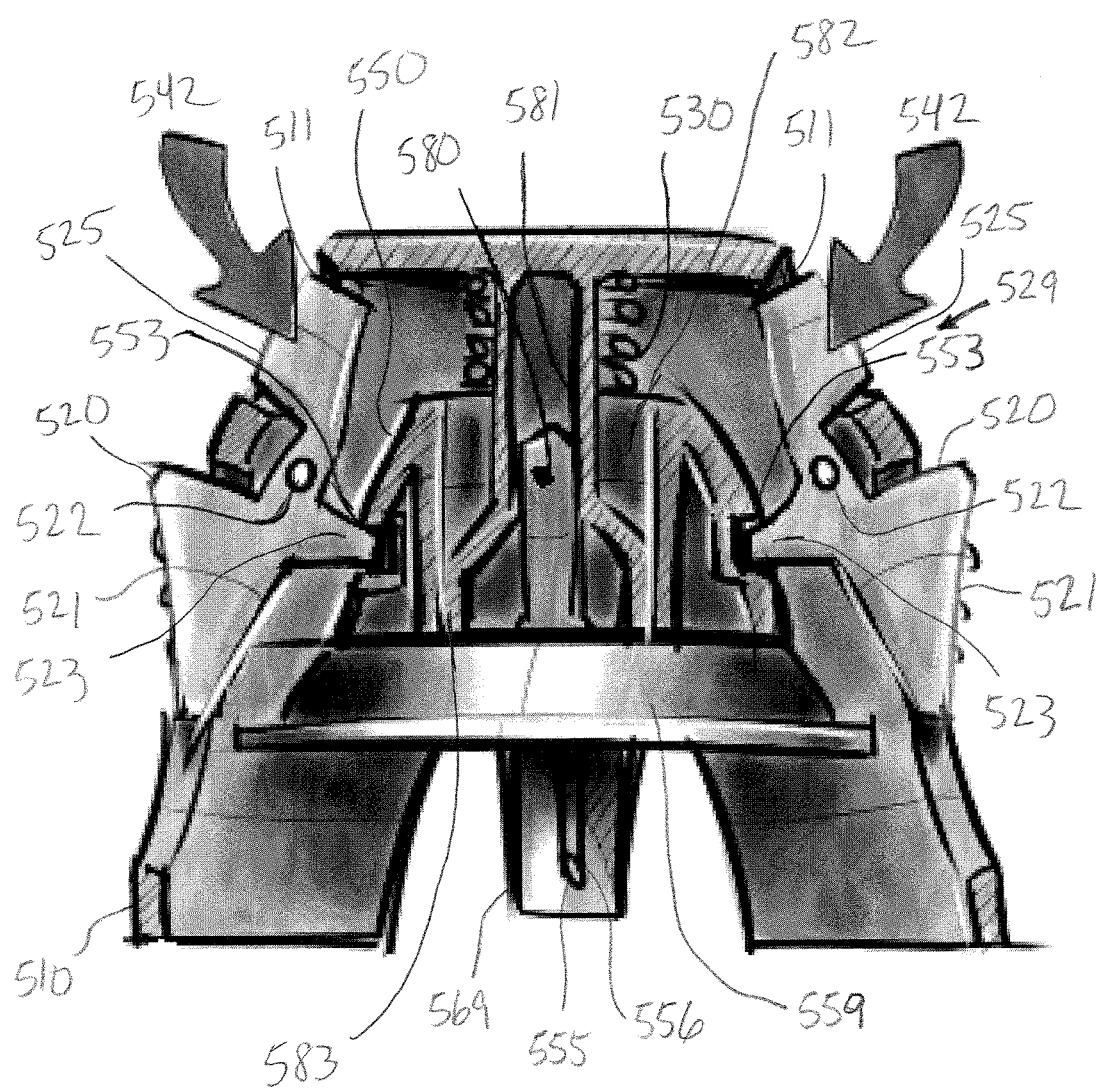
FIG. 37 is a partial cross-sectional view of the loaded insertion device shown in FIG. 36.
Figure 38:
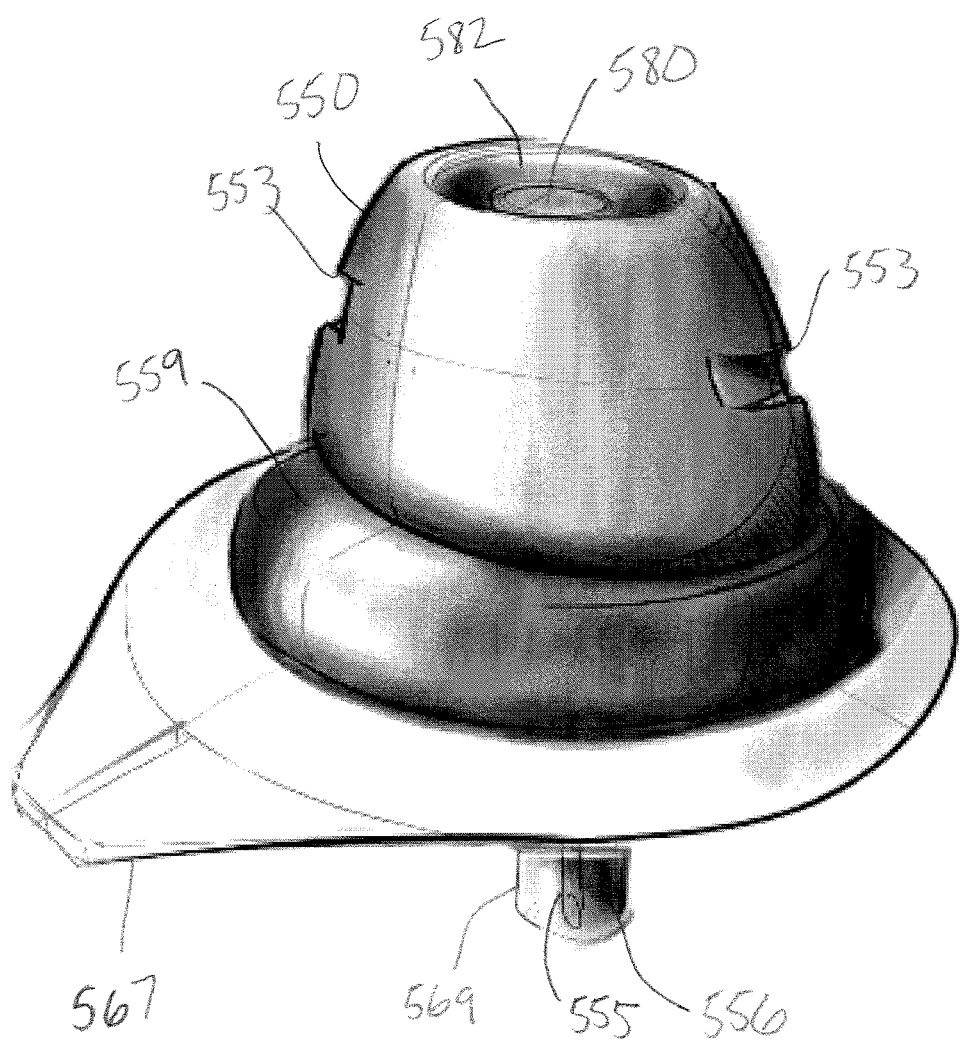
FIG. 38 is a perspective view of the insertion set shown in FIG. 36.
Figure 39:
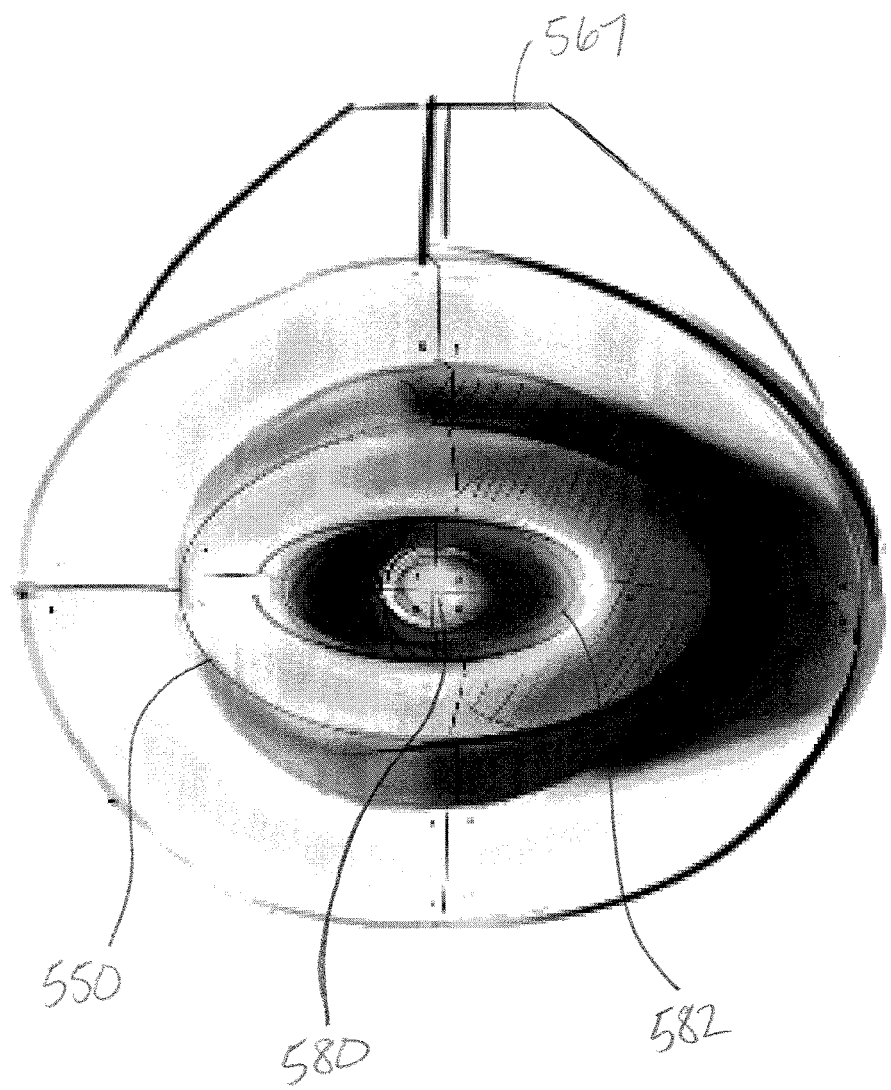
FIG. 39 is a top view of the insertion set shown in FIG. 36.
Figure 40:
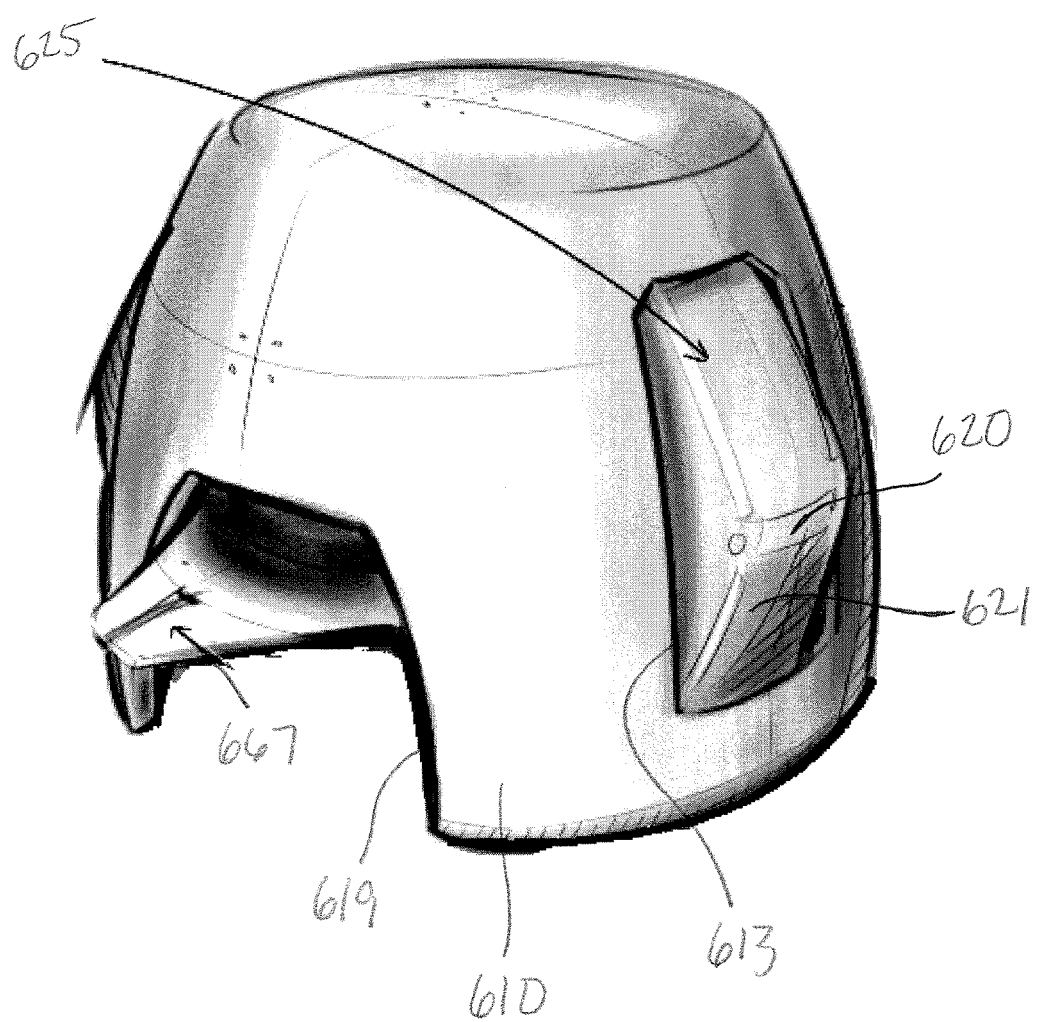
FIG. 40 is a perspective view of one embodiment of the present insertion devices loaded with an insertion set.
Figure 41:
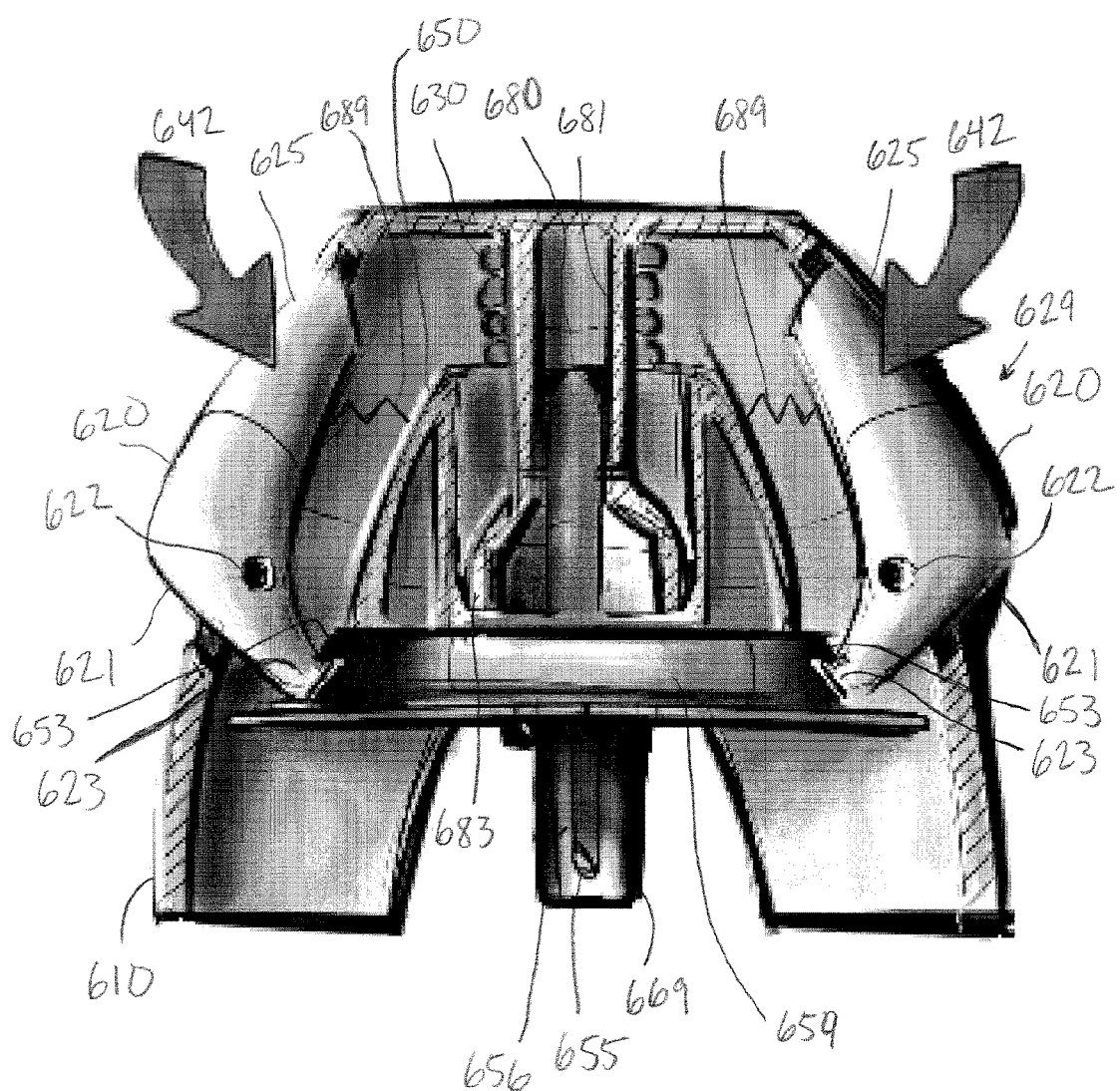
FIG. 41 is a partial cross-sectional view of the loaded insertion device shown in FIG. 40.
Figure 42:
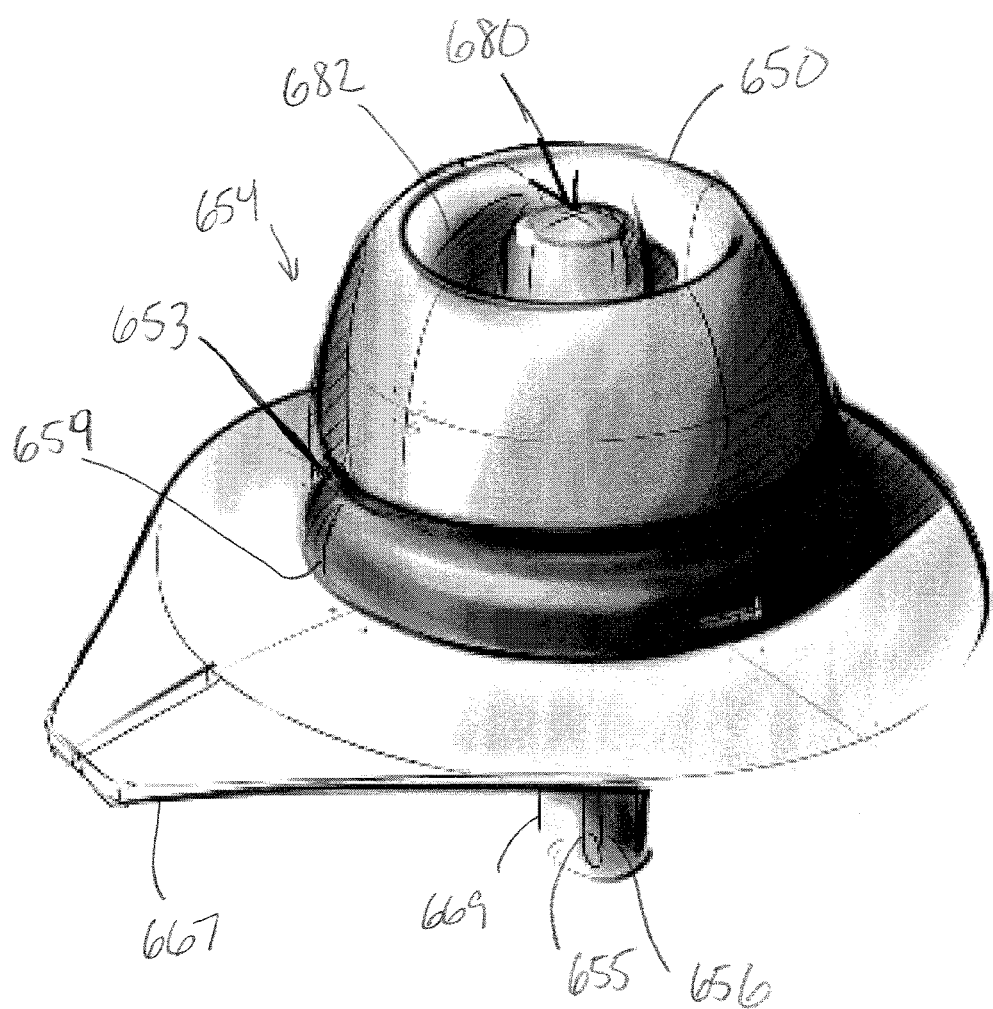
FIG. 42 is a perspective view of the insertion set shown in FIG. 41.
Figure 43:
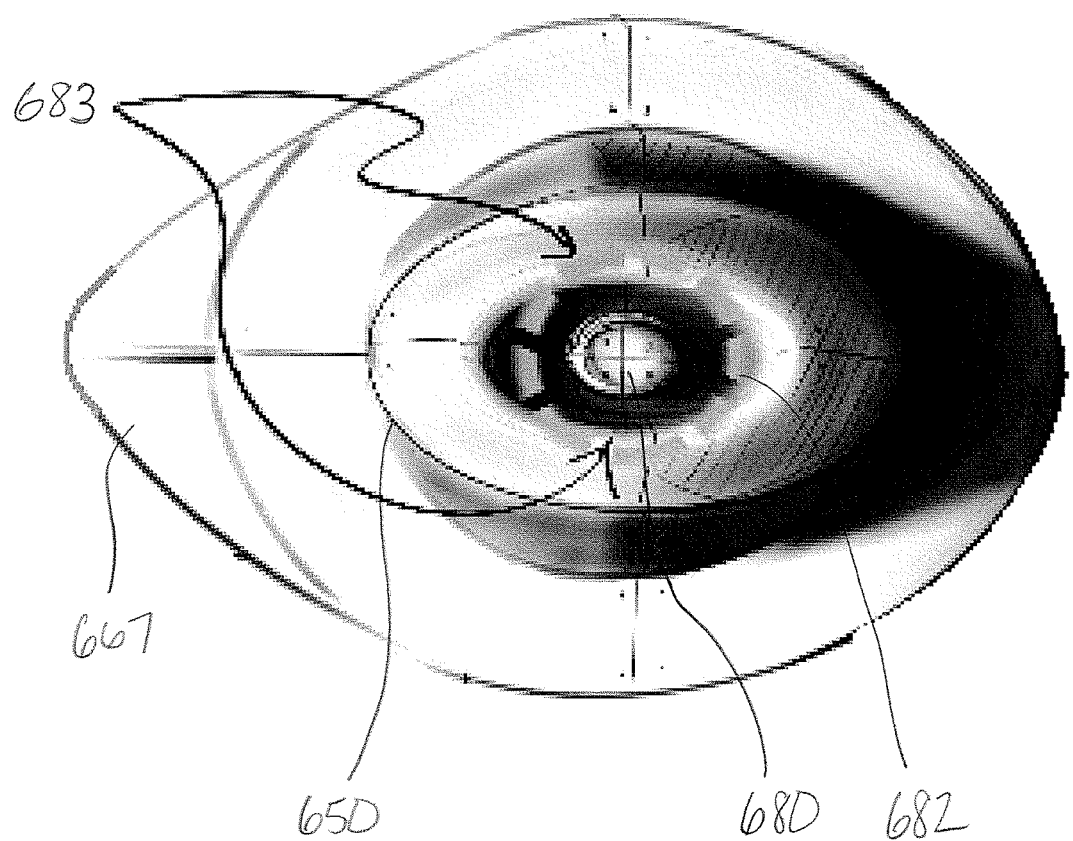
FIG. 43 is a top view of the insertion set shown in FIG. 41.

The embodiment shown in FIG. 35 is similar to the embodiment shown in FIGS. 32-34. However, the drivers and housings are configured differently. Housing 410 of the embodiment in FIGS. 32-34 includes a driver guide post 481 extending proximally from the inside surface of the distal end of the housing. Driver 430 in the embodiment shown in FIG. 35 is configured to act on a central portion of needle hub 450. In the embodiment shown in FIG. 33, driver 430 acts on a more outer circumferential portion of needle hub 450.

Referring now to FIGS. 36-39, another embodiment of the present insertion devices is illustrated that operates in generally the same manner as the embodiment shown in FIGS. 32-35. Unless otherwise noted, elements of the embodiment in FIGS. 36-39 that are similar to elements of the embodiment in FIGS. 32-35 are given similar reference numbers in the Figures (e.g. "5xx" in FIGS. 36-39 and "4xx" in FIGS. 32-35). In the embodiment shown, insertion set retention elements 520 of insertion set retention mechanism 529 rotate about a pair of pivot pins 522 through which they are coupled to housing 510. For the sake of brevity, a description of similar operating principles and elements will not be repeated. In the embodiment of FIGS. 36-39, however, release elements 525 extend through apertures 511 located on the upper portion of the side (rather than the top) of housing 510. In addition, needle hub 550 comprises an alignment post 580 that is configured to extend into (and may contact and be guided by) driver guide post 581 of housing 510 to assist in orienting needle hub 530 (and, more generally, insertion set 554) correctly within housing 510 during the loading process. Needle hub 550 also comprises a recess 582 into which driver guide post 581 extends (and with which driver guide post 581 may contact) to assist in insertion device orientation during loading; the proximal portion 583 of driver guide post 581 may be flared so as to contact the portion of needle hub 530 that defines recess 582. The manner in which insertion device 500 may be loaded with insertion set 554 is similar to the manner in which insertion device 400 may be loaded with insertion set 454.

Referring now to FIGS. 40-43, another embodiment of the present insertion devices is illustrated that operates in generally the same manner as the embodiment shown in FIGS. 36-39. Unless otherwise noted, elements of the embodiment in FIGS. 40-43 that are similar to elements of the embodiment in FIGS. 36-39 are given similar reference numbers in the Figures (e.g. "6xx" in FIGS. 36-39 and "5xx" in FIGS. 32-35). In the embodiment shown, insertion set retention elements 620 of insertion set retention mechanism 629 rotate about a pair of pivot pins 622 through which they are coupled to housing 610. For the sake of brevity, a description of similar operating principles and elements will not be repeated. In the embodiment of FIGS. 40-43, however, insertion set retention elements 620 do not slide within apertures 613. In addition, insertion device 600 includes a biasing member 689 extending from each insertion set retention element 620 that biases that insertion set retention element when it contacts the insertion set (specifically, the needle hub) so that it pivots about the relevant pivot pin 622. The biasing action causes engaging portions 623 to be directed toward the central portion of insertion device 600. These biasing members are part of insertion set retention mechanism 629, and may be springs or any other suitably resilient material coupled to the insertion set retention elements in any suitable manner and configured to contact a suitably configured insertion set. As needle hub 650 is directed into housing 610, engaging portions 623 will contact (e.g., engage) retention notches 653, which can be located in base 659 of insertion set 654 rather than in needle hub 650. Needle guard 669 can be made sufficiently rigid that a user can load driver 630 by pushing on needle guard 669 until engaging portions 623 engage insertion set 654. Further, all of the present insertion devices can be configured so that a friction fit keeps their respective needle guard coupled to their respective base such that a user can handle the insertion set by the needle guard, such as during the insertion set loading process.

A user can press on release elements 625 (in the direction shown by arrows 642) so that the force applied by biasing elements 689 is overcome and engaging portions 623 are released (e.g., disengaged) from retention notches 653. This action can allow driver 630 to move needle hub 650 and insertion set 654 from the pre-installed position shown in FIG. 41 to an installed position. Insertion device 600 may be configured such that the proximal end of driver 630 contacts needle hub 650 in the general area identified by arrows 683 shown in FIG. 43.

Referring next to FIGS. 44-47, another embodiment of the present insertion devices is shown. Unless otherwise noted, elements of the embodiment in FIGS. 44-47 that are similar to elements of the embodiment in FIGS. 40-43 are given similar reference numbers in the Figures (e.g. "7xx" in FIGS. 44-47 and "6xx" in FIGS. 40-43). For the sake of brevity, a description of similar operating principles and elements will not be repeated.

Insertion device 700 comprises a housing 710 with a proximal or lower aperture 712, and a pair of insertion set retention elements 720 that include a release element 725 (on the upper portion of insertion set retention element 720) and an engaging portion 723 (on the lower portion of insertion set retention element 720). Housing 710 of the embodiment of FIGS. 44-47 may also comprise a rotatable top 790 that includes gripping members 794, which, in the depicted embodiment, take the form of ridges that are substantially aligned with the axis of the insertion needle. Though not shown, rotatable top 790 may include an inwardly projecting lip that rides in a groove in the side wall of the housing to keep the side wall and the top coupled together. In this exemplary embodiment, insertion set retention mechanism 729, which comprises insertion set retention elements 720, is coupled to housing 710 by virtue of being integral with housing 710. In other embodiments, insertion set mechanism 729 (and therefore insertion set retention elements 720) may not be integral with housing 710.

Figure 45:
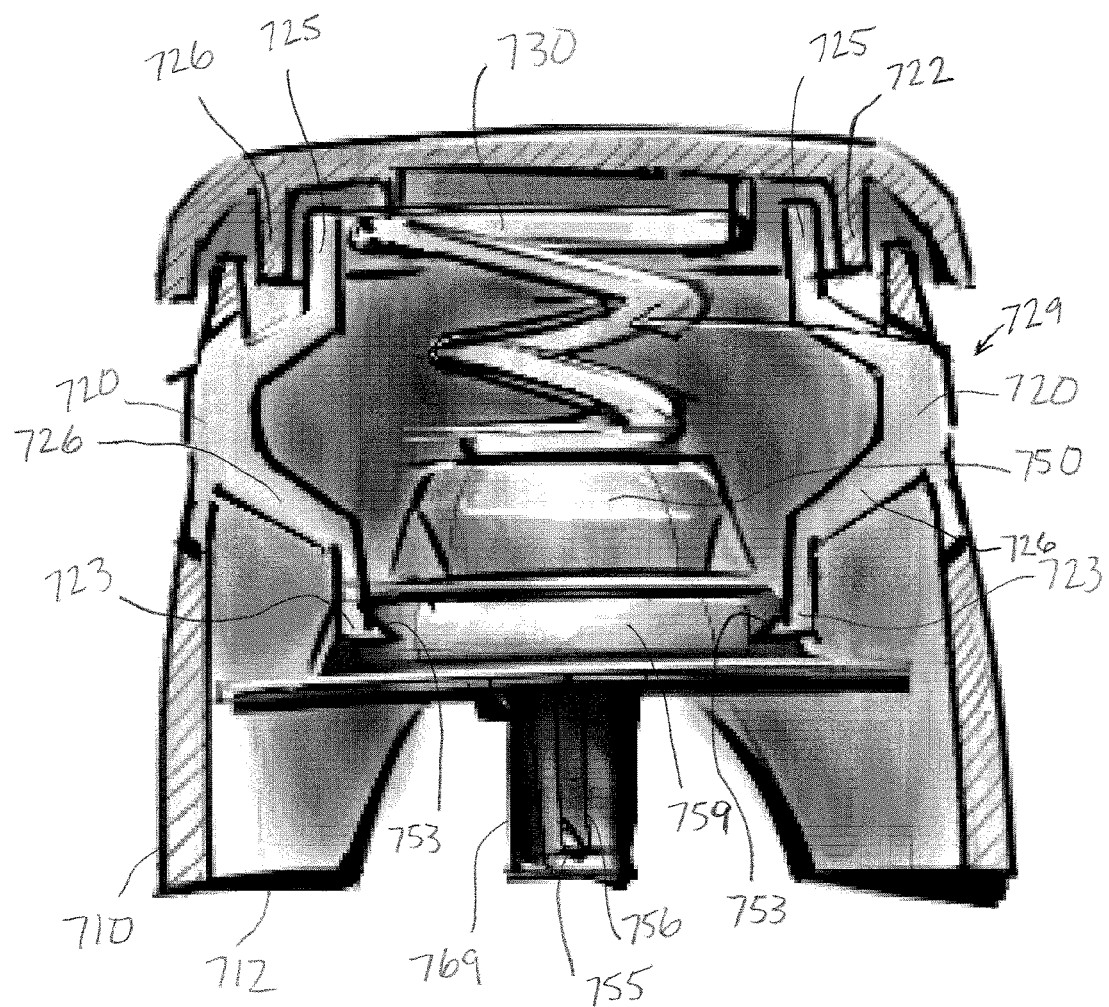
FIG. 45 is a partial cross-sectional view of the loaded insertion device shown in FIG. 44.
Figure 46:
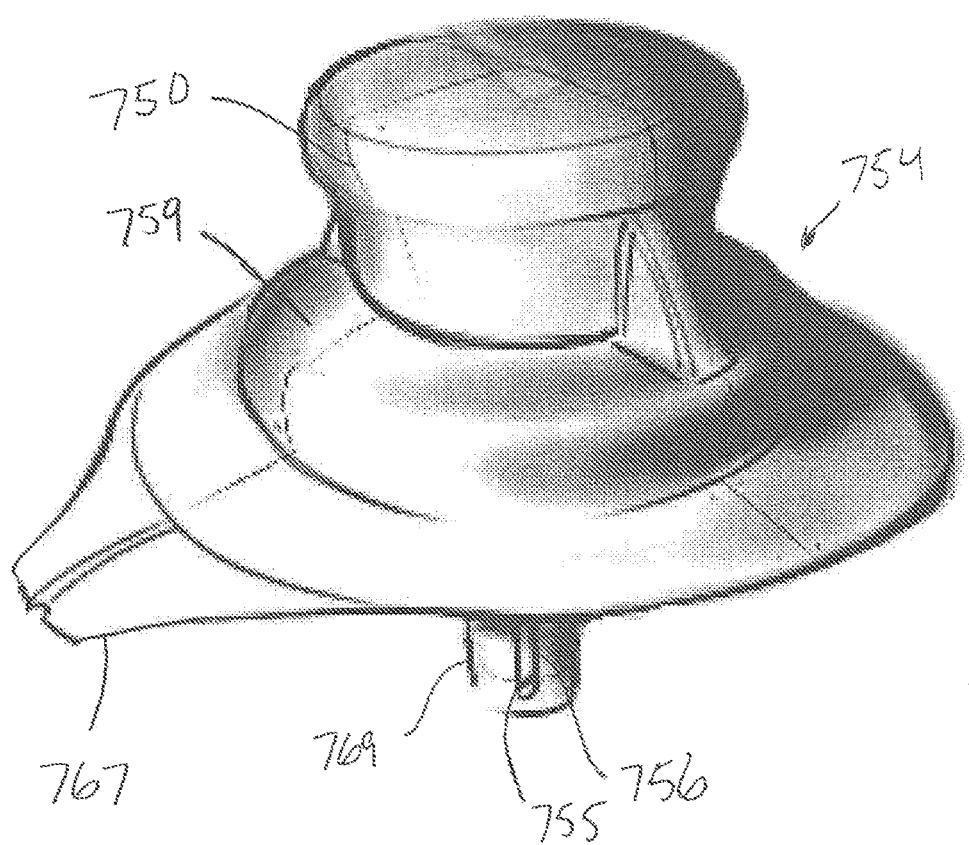
FIG. 46 is a perspective view of the insertion set shown in FIG. 45.
Figure 47:
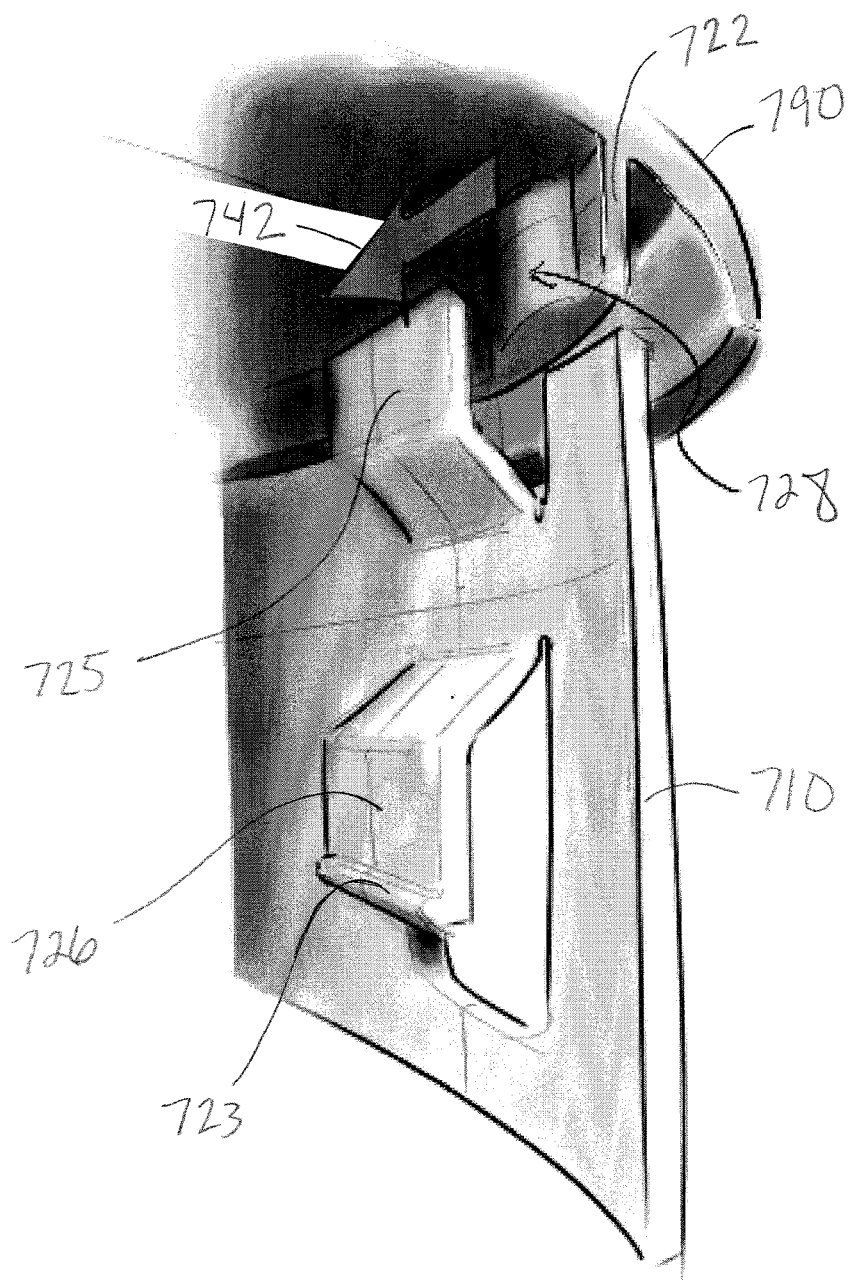
FIG. 47 is a partial cross-section view of the insertion device shown in FIG. 44.

Insertion device 700 is loaded in a manner generally similar to previously described embodiments (e.g., needle hub 750 and, more generally, insertion set 754 are inserted into aperture 712 and directed toward the top or distal end of insertion device 700 by pushing on needle guard 769). In this embodiment, engaging portions 723 are configured to contact (e.g., engage) retention notches 753 of base 759 (which, in an alternative embodiment, may be configured as a retention groove that extends continuously around the base, as is true of the base embodiment shown in FIG. 41) as insertion set 754 is moved upward into housing 710. Engaging portions 723 can be configured (for example, with a tapered surface proximal to aperture 712) so that proximal portions 726 of insertion set retention elements 720 flex slightly outward as engaging portion 723 engages retention notches 753. The geometry and dimensions of engaging portion 723 and insertion set retention elements 720 (and, more specifically, proximal portions 726 of the insertion set retention elements) can be configured so that engaging portions 723 are normally engaged with retention notches 753 when insertion set 754 is positioned as shown in FIG. 45. Housing 710 can be formed (e.g., molded) so that proximal portions 726 have an inward bias that facilitates this engagement.

Figure 44:
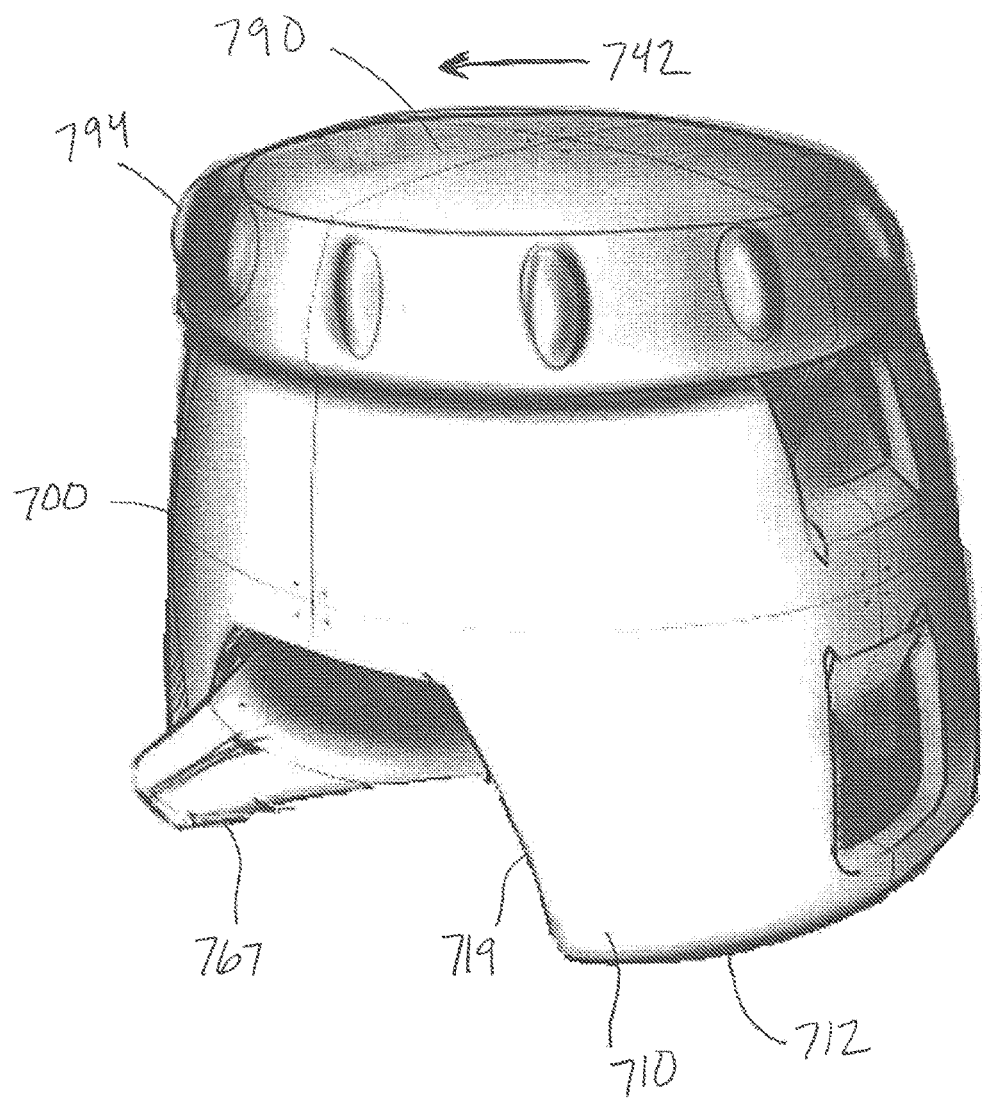
FIG. 44 is a perspective view of one embodiment of the present insertion devices loaded with an insertion set.

A user can release insertion set 754 from the pre-installed position shown in FIG. 45 by rotating top 790 in the direction shown by arrow 742 in FIG. 44. Rotation of top 790 will cause an inner wall 722 that extends proximally from the inner surface of top 790 to rotate and cause release actuators 728 to engage release element 725 of insertion set retention elements 720. In the embodiment shown, this movement will create a cam action that causes proximal portions 726 to flex outward a sufficient amount to result in the in the disengagement of engaging portions 723 with retention notches 753. As a result, driver 730 can then cause insertion set 754 to move from the pre-installed position shown in FIG. 45 to an installed position on a user.

Figure 48:
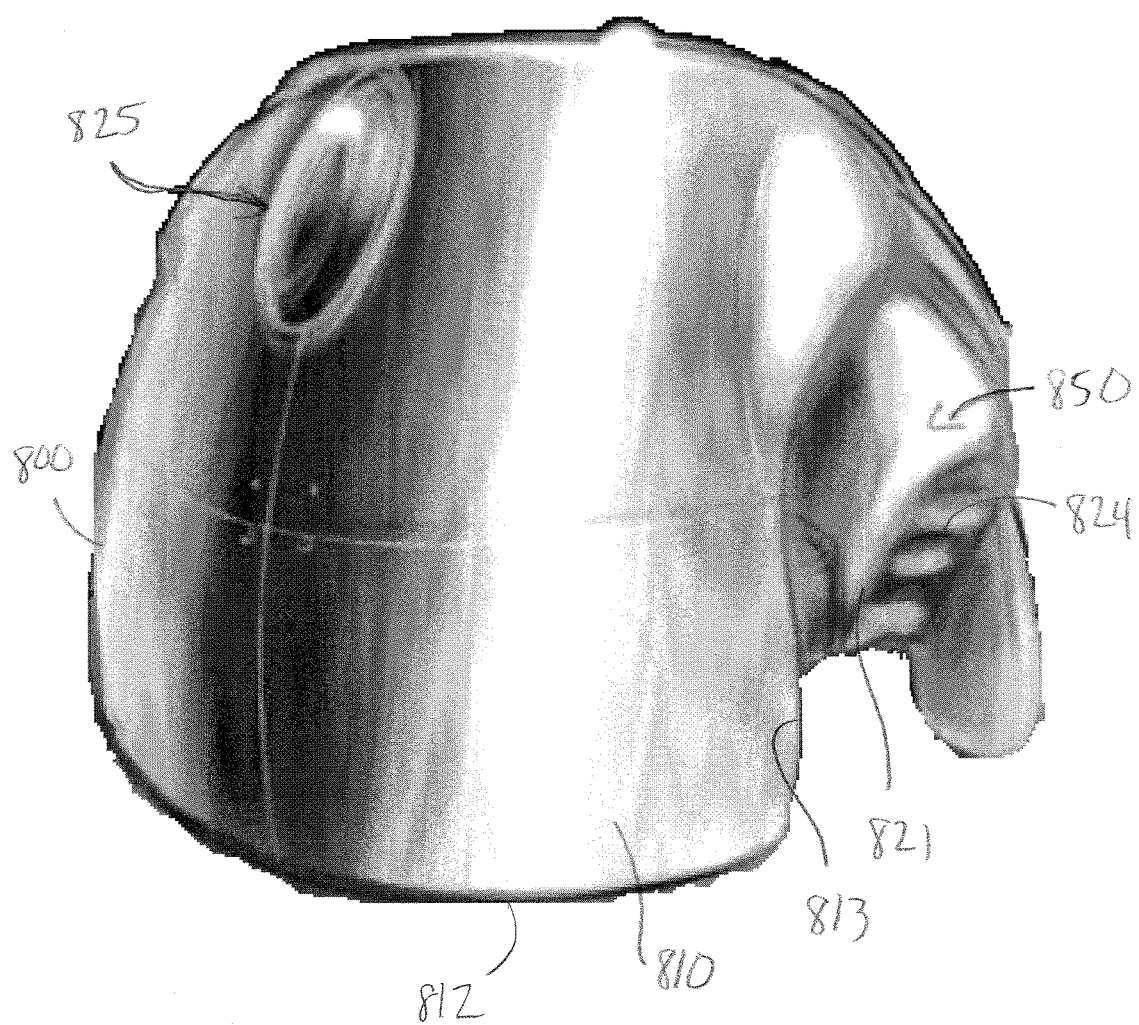
FIG. 48 is a perspective view of one embodiment of the present insertion devices loaded with an insertion set.
Figure 49:
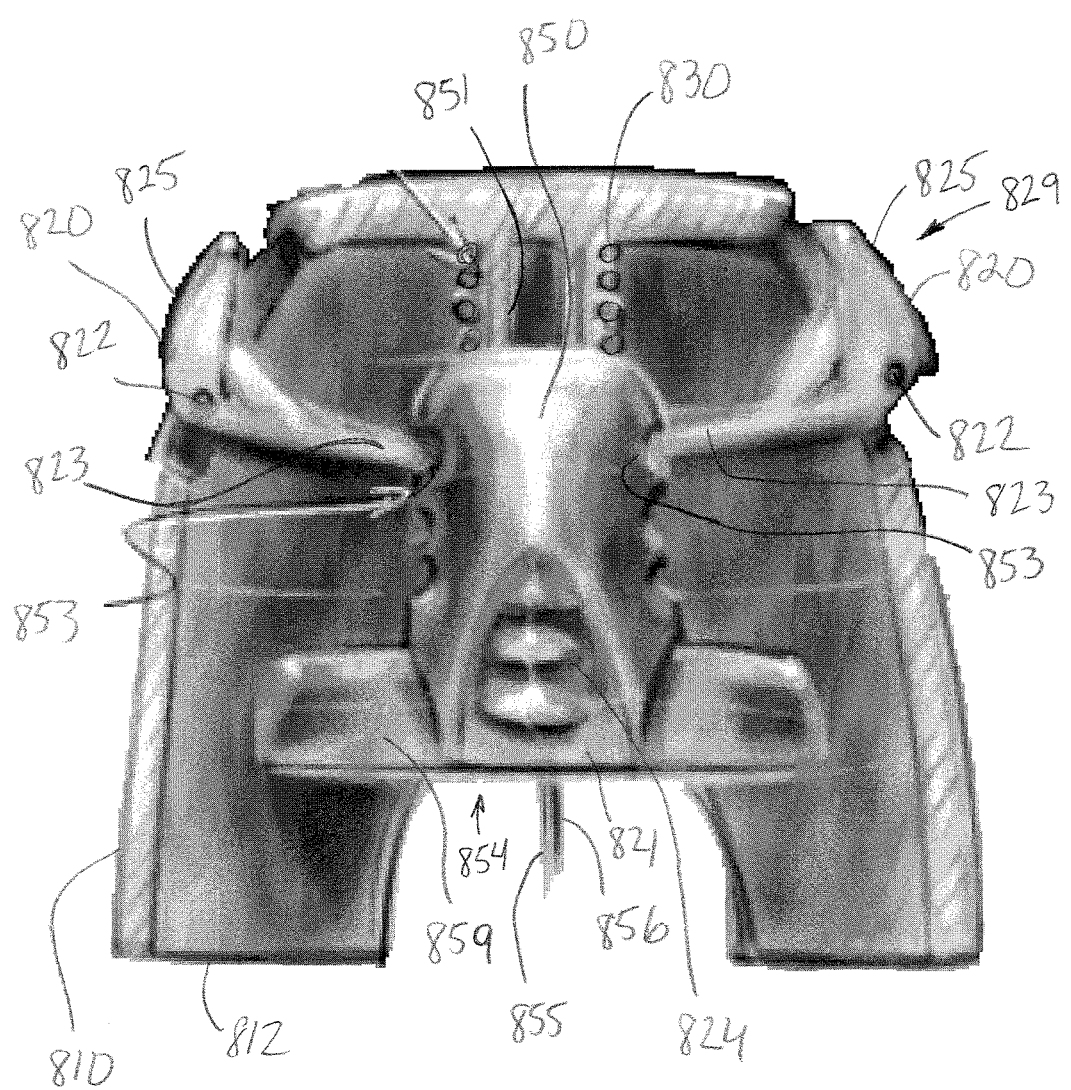
FIG. 49 is a partial cross-sectional view of the loaded insertion device shown in FIG. 48.
Figure 50:
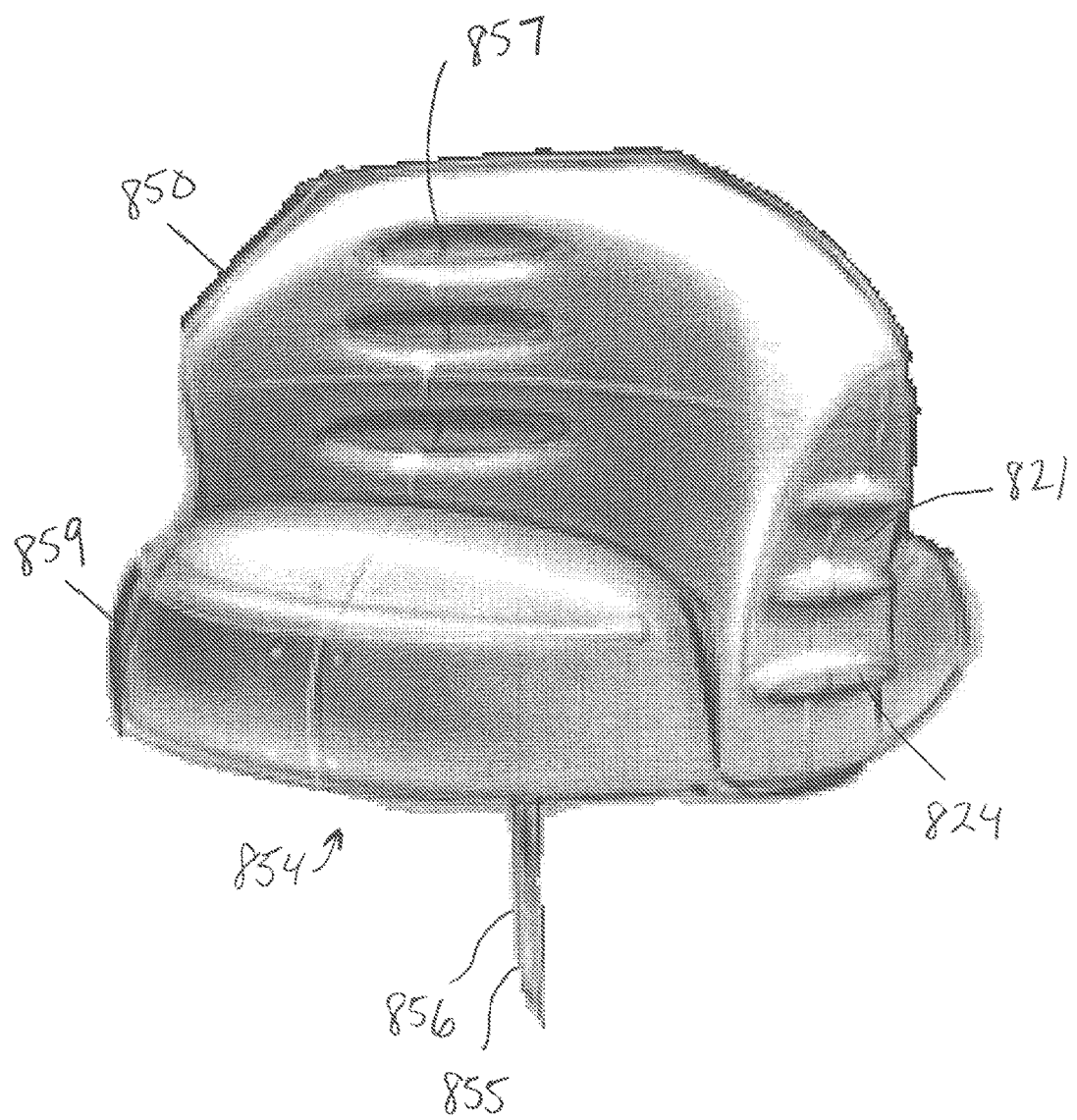
FIG. 50 is a perspective view of the insertion set shown in FIG. 49.
Figure 51:
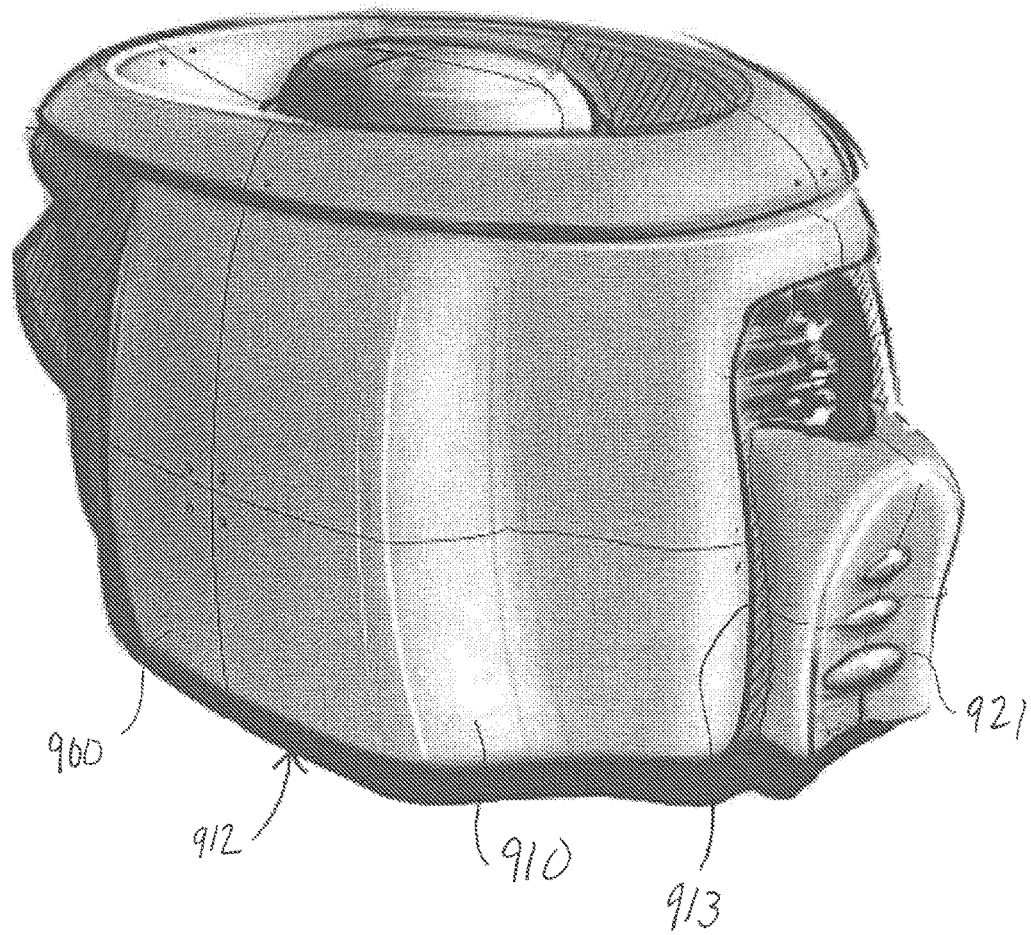
FIG. 51 is a perspective view of one embodiment of the present insertion devices loaded with an insertion set.
Figure 52:
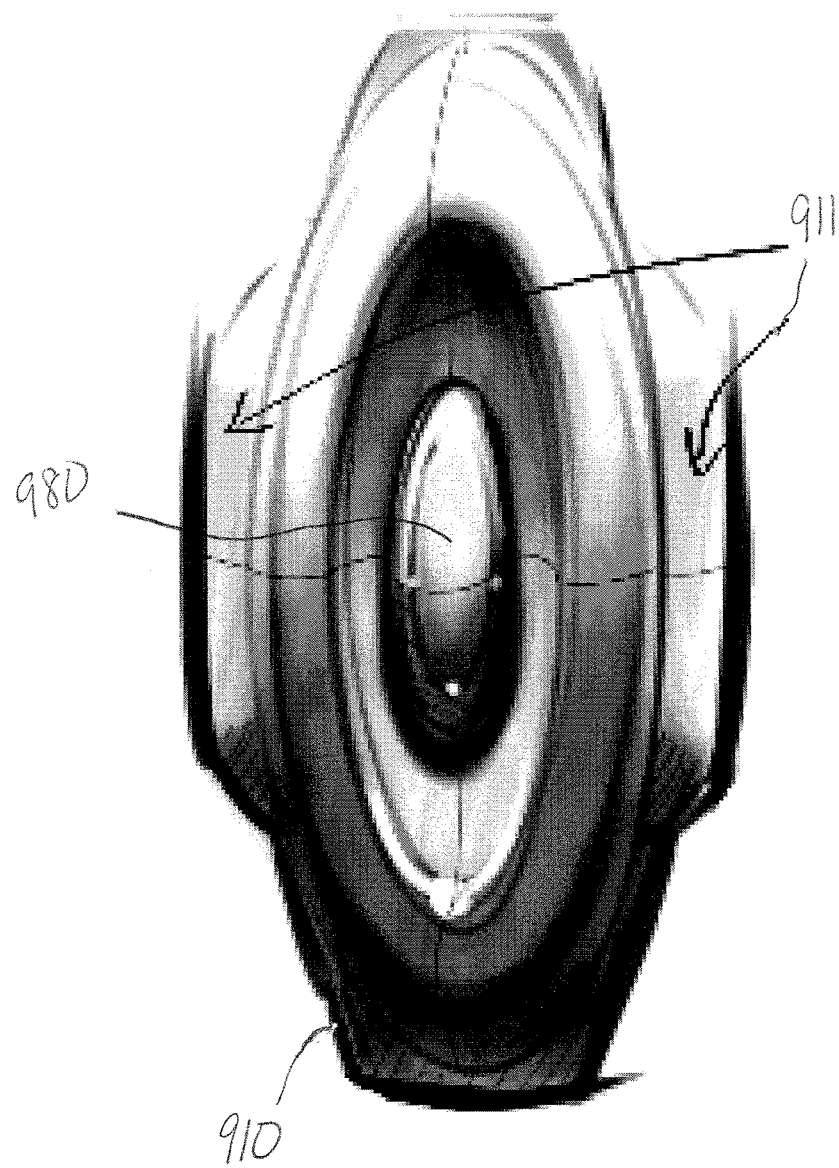
FIG. 52 is a top view of the insertion set shown in FIG. 51.
Figure 53:
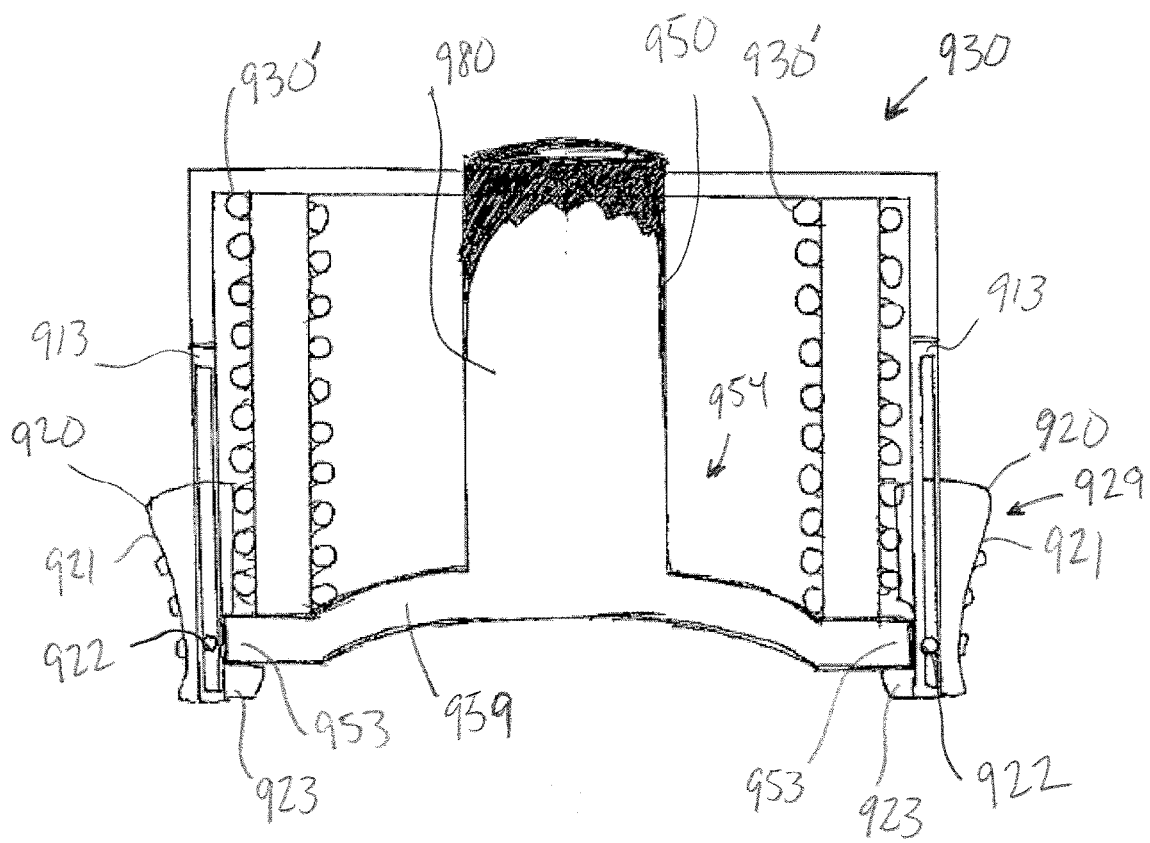
FIG. 53 is a partial cross-sectional view of the loaded insertion device shown in FIG. 51.
Figure 54:
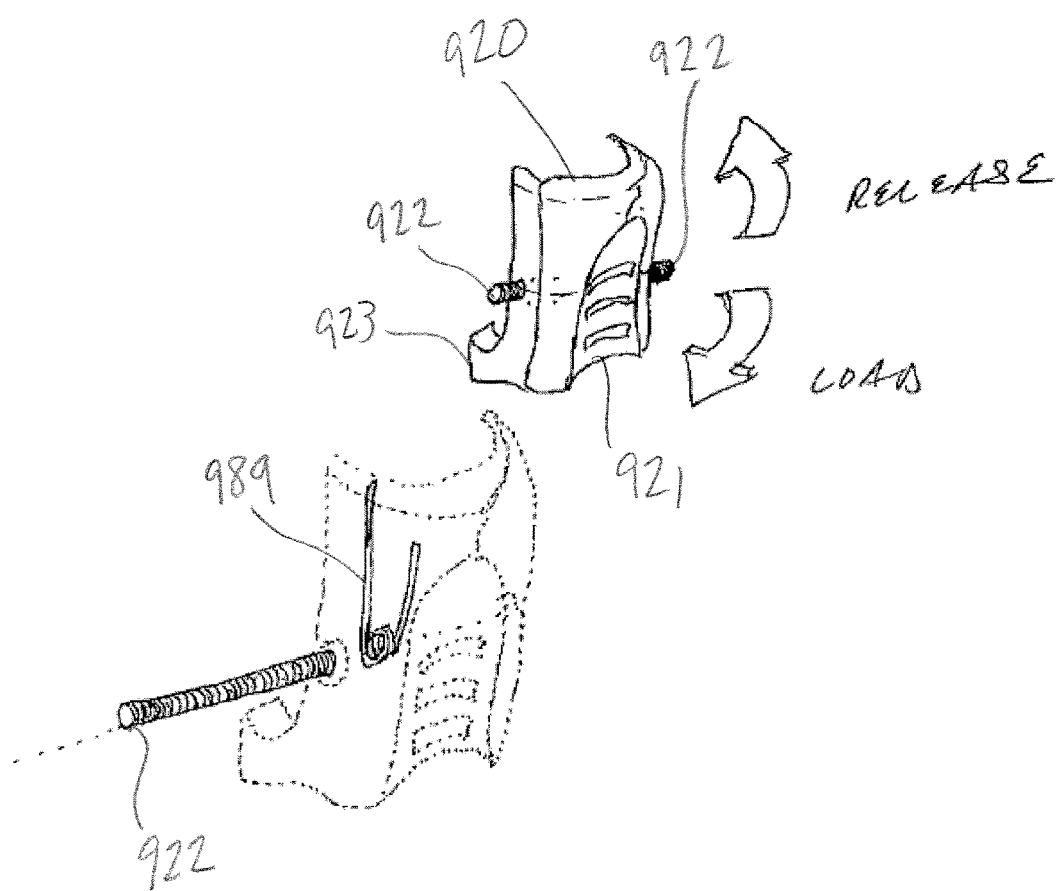
FIG. 54 is a detailed view of a portion of the retention mechanism of the insertion device shown in FIG. 51.

Referring now to FIGS. 48-50, another embodiment of the present insertion devices is shown. Unless otherwise noted, elements of the embodiment in FIGS. 48-50 that are similar to elements of the embodiment in FIGS. 44-47 are given similar reference numbers in the Figures (e.g. "8xx" in FIGS. 48-50 and "7xx" in FIGS. 44-47). For the sake of brevity, a description of similar operating principles and elements will not be repeated.

Insertion device 800 comprises a housing 810 with a proximal or lower aperture 812, and a pair of insertion set retention elements 820 that include a release element 825 (on the upper portion of insertion set retention element 820) and an engaging portion 823 (on the lower portion of insertion set retention element 820). In the embodiment shown, insertion set retention elements 820 of insertion set retention mechanism 829 rotate about a pair of pivot pins 822 through which they are coupled to housing 810. A user can load insertion device 800 by grasping gripping elements 821 of needle hub 850 and directing needle hub 850 upward into housing 810. As needle hub 850 is directed upward, engaging portions 823 of insertion set retention element 820 are configured to contact (e.g., engage) retention notches 853 of needle hub 850.

In the embodiment shown, insertion device 800 engages insertion set 854 through an interference fit (e.g., a snap fit) between engaging portions 823 and retention notches 853 that is sufficient to resist the force exerted on insertion set 854 by driver 830. The interference fit between engaging portions 823 and retention notches 853 can therefore maintain driver 830 in a loaded, pre-installed position until a user manipulates release elements 825 as described below. In other embodiments, a biasing member (not shown) can bias engaging portions 823 into engagement with retention notches 853.

As shown in FIG. 50, needle hub 850 includes central gripping element 857 positioned between retention notches 853 that can be used to assist a user in installing insertion set 854 without the assistance of insertion device 800.

A user can release needle hub 850 (and therefore insertion set 854) from insertion device 800 by squeezing on the release elements 825. This action can cause insertion set retention elements 820 to pivot about pivot pins 822 and cause engaging portions 823 to become disengaged from retention notches 853. Driver 830 can then cause insertion set 854 to move from the pre-installed position shown in FIG. 49 to an installed position on a user.

Referring now to FIGS. 51-54, another embodiment of the present insertion devices is shown. Unless otherwise noted, elements of the embodiment in FIGS. 51-54 that are similar to elements of the embodiment in FIGS. 48-50 are given similar reference numbers in the Figures (e.g. "9xx" in FIGS. 51-54 and "8xx" in FIGS. 48-50). For the sake of brevity, a description of similar operating principles and elements will not be repeated.

Insertion device 900 comprises a housing 910 with a proximal or lower aperture 912 and a pair of lateral slots 913 that extend upward (toward the distal end of the housing) from aperture 912. As shown in the top view of FIG. 52, housing 910 comprises a pair of extensions or flared portions 911 configured to accommodate an insertion set. Insertion device 900 also comprises a pair of insertion set retention elements 920 that include a pair of gripping elements 921 (on the outer portion of insertion set retention element 920) and a pair of engaging portions 923 (on the lower inner portion of insertion set retention elements 920). In the embodiment shown, insertion set retention elements 920 of insertion set retention mechanism 929 rotate about a pair of pivot pins 922 through which they are coupled to housing 910. A user can load insertion device 900 by placing needle hub 950 (and, more generally, insertion set 954) into aperture 912 and grasping the lower portions of gripping elements 921 (e.g., the portion below pivot pins 922) so that engaging portions 923 contact (e.g., engage) retention elements 953 of needle hub 950.

The user can then direct gripping elements 921 to the upper portion of lateral slots 913 to compress the driver 930 of the insertion device, which takes the form of two springs 930'. When the user releases the lower portion of gripping elements 921, biasing members 989 (see FIG. 54) bias insertion set retention elements 920 so that engaging portions 923 engage retention elements 953. In addition, a notch (not shown) or other retention structure in slot 913 can engage pivot pins 922 and retain drivers 930 in the compressed position. When the user wishes to release needle hub 950 and insertion set 954, the user can press inward on the upper surface of gripping elements 921 to release engaging portions 923 from retention elements 953. Driver 930 can then cause insertion set 954 to move from a pre-installed position to an installed position on a user.

In certain embodiments, the distal end or ends of the drivers shown in FIGS. 20-54 can be coupled to the relevant housing by being molded into the housing. In other embodiments, the driver distal end(s) can be coupled to the relevant housing by clips or other retainers. In still other embodiments, the driver distal end(s) can be engaged with apertures or slots in the relevant housing.

In certain embodiments, the ends of the pivot pins shown in the Figures can be inserted into apertures that extend partially or completely through the relevant housing. The pivot pins may be configured (for example, with an internal spring) so that their overall length can be compressed during insertion device assembly to allow insertion into the housing apertures. In embodiments that allow for both sliding and pivoting of the insertion set retention elements, the ends of the pivot pins may be positioned in slots rather than apertures in the housing.

Insertion Devices that do not have a Driver and Insertion Needles Having a Driver Some embodiments of the present insertion devices do not have a driver. Instead, some embodiments of the present insertion needles have a driver. One such embodiment of the present insertion needles is the insertion needle shown in cross section in FIG. 55. That insertion needle is shown coupled to a base of an insertion set that can be any suitable 90-degree entry insertion, such as base 20 of the insertion set that is shown in, for example, FIG. 1 of U.S. Ser. No. 11/592,719, which is incorporated by reference. Together, one of the present insertion needles that has a driver and any suitably shaped base comprise one of the present insertion sets.

Figure 7:
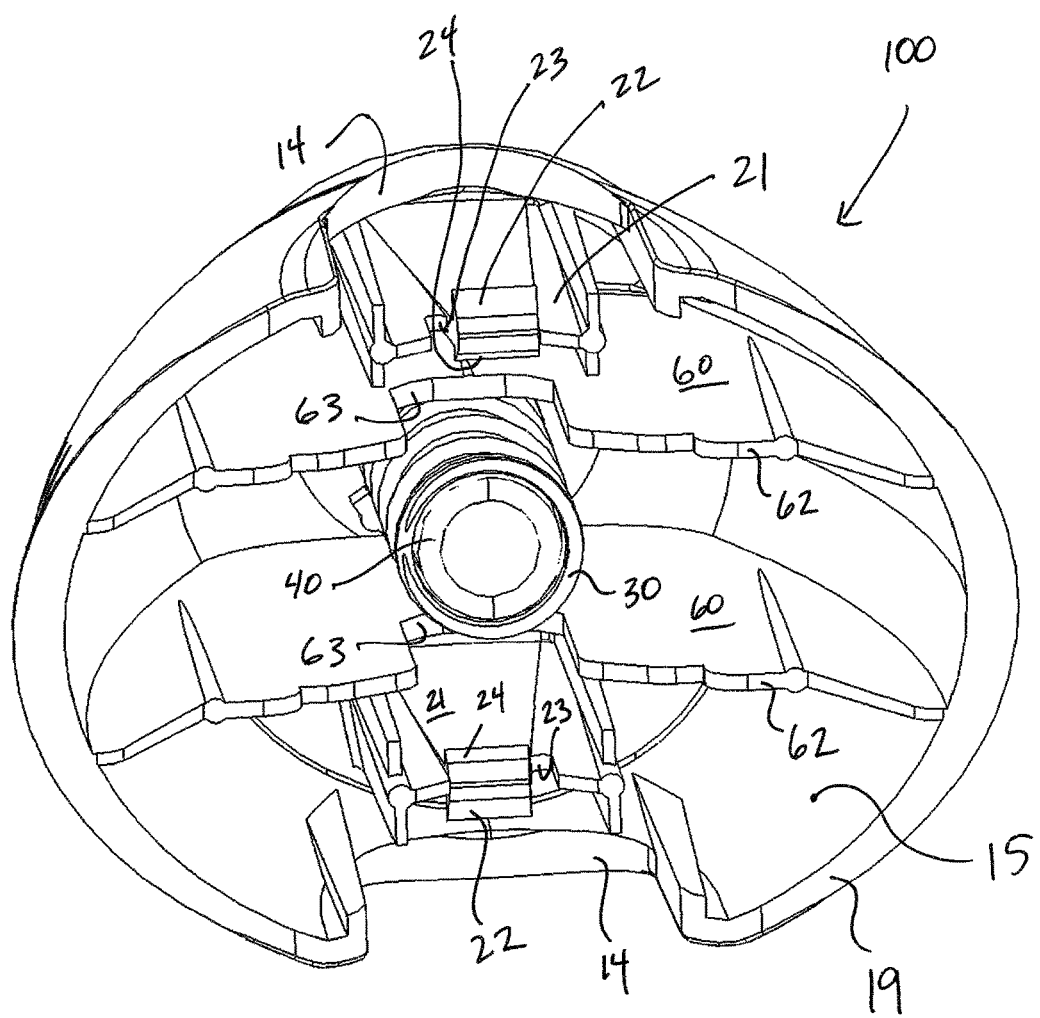
Figure 8:
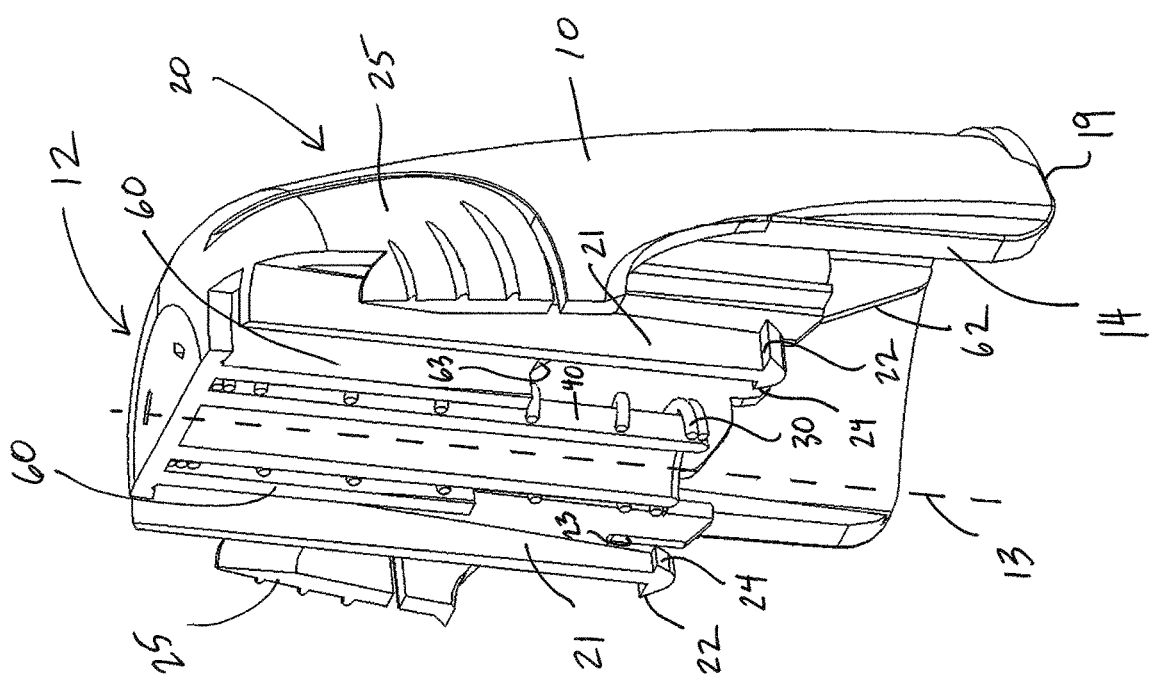
Figure 9:
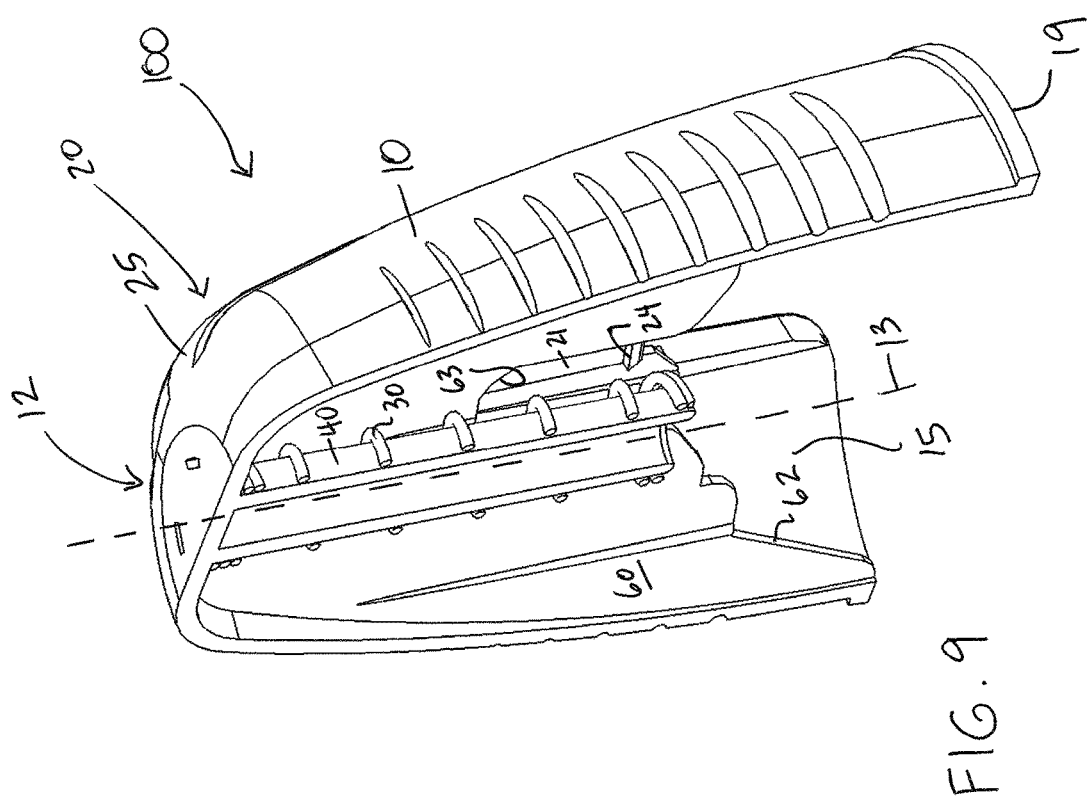
Figure 13:
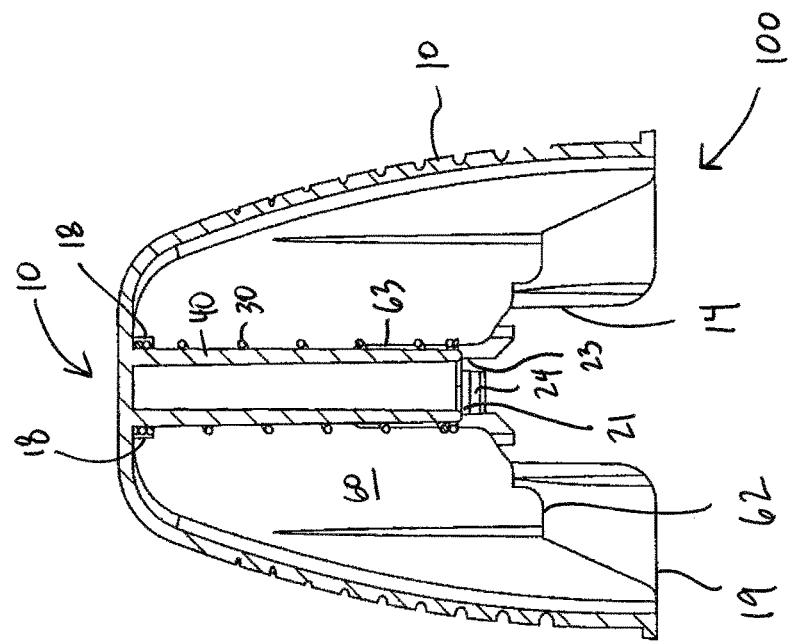
Figure 12:
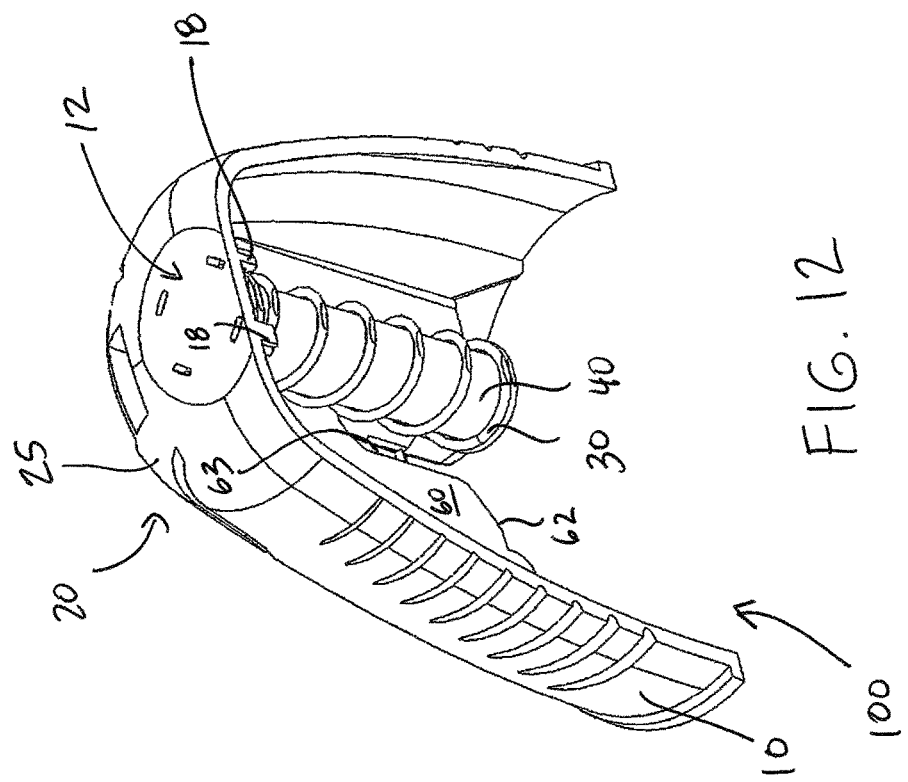
Figure 55:
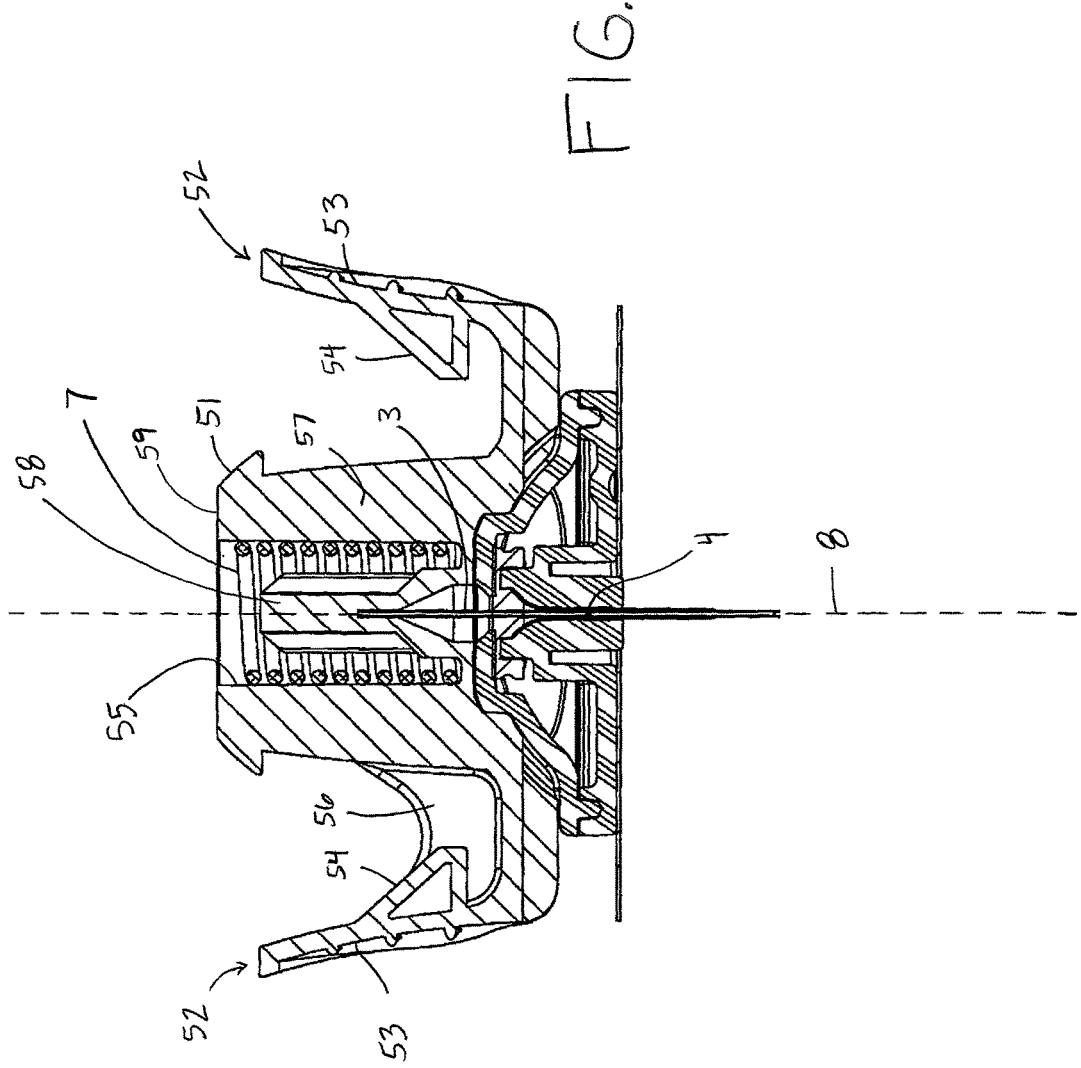

Central portion 57 of the insertion needle hub 50 shown in FIG. 55 has a top surface 59, and recess 55 extends into central portion 57 from top surface 59. Insertion needle hub stem 58 may also be referred to as post 58. The needle 3 that is attached to insertion needle hub 50 has an exposed end 4; the other end of the needle is embedded in post 84 in the depicted embodiment. End 4 is "exposed" when the insertion needle is separated from the base of the insertion set, as in FIG. 16; in FIG. 55, end 4 is bounded by the cannula of the base of the insertion set. Needle 3 is substantially aligned with axis 8, which is substantially centered in post 58 and in recess 55. The insertion needle also includes a driver 7 (which is in the form of a spring in the depicted embodiment) that is attached in any suitable fashion to insertion needle hub 50 but not to any structure other than the insertion needle (e.g., it is not attached to an insertion device, such as insertion device 100). In contrast, spring unit 13 that is attached to needle hub 2 of the insertion set shown in FIG. 7 of U.S. Ser. No. 11/298,259 (which is incorporated by reference) is also attached to set housing 1 of the depicted insertion device.

In some embodiments, driver 7 (e.g., as a spring) may be attached to insertion needle hub 50 with driver retention clips similar to clips 18 of insertion device 100; any suitable number of clips may be used (e.g., 2, 3, 4 or more). In other embodiments, the proximal end of driver 7 (e.g., as a spring) may be molded into insertion needle hub 50. Either way, driver 7 as a spring may be capable of movement between a constrained position (corresponding to the state in which the insertion set of which it is a part is loaded in a pre-installed position to a suitable insertion device) and an unconstrained position (which exists, for example, when installation is complete and the insertion set is not coupled to the insertion device).

The present insertion needle hubs may be characterized as being configured such that, after installation, they may be connected only to a needle and to the base of an infusion set and not connected (or unconnected) to any other structure. In contrast, needle hub 2 is described as unreleasably connected to carrier body 4 in U.S. Ser. No. 11/298,259.

As shown in FIG. 55, the depicted embodiment of driver 7 is positioned at least partially (and, in the depicted embodiment, completely) in recess 55 and no portion of driver 7 is farther from exposed end 4 of needle 3 than top surface 59 of central portion 57 of the insertion needle hub. In other words, the top of driver 7 (the portion of driver 7 farthest from end 4 of needle 3) is below the plane (not shown) in which top surface 59 resides. Driver 7 is also positioned at least partially around post 58. More specifically, in the depicted embodiment, all but the top portion of driver 7 is positioned around post 58.

Figure 19:
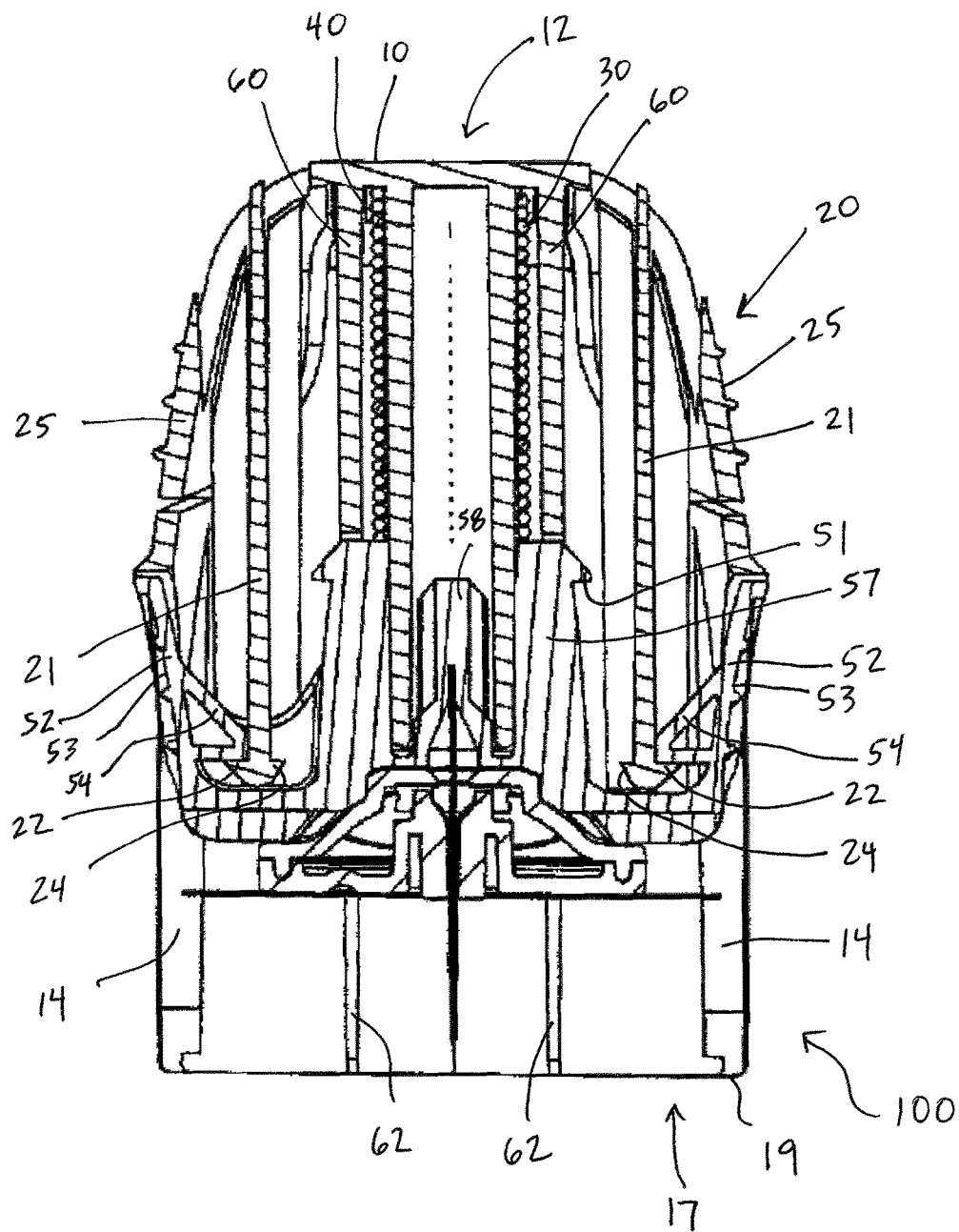
Figure 56:
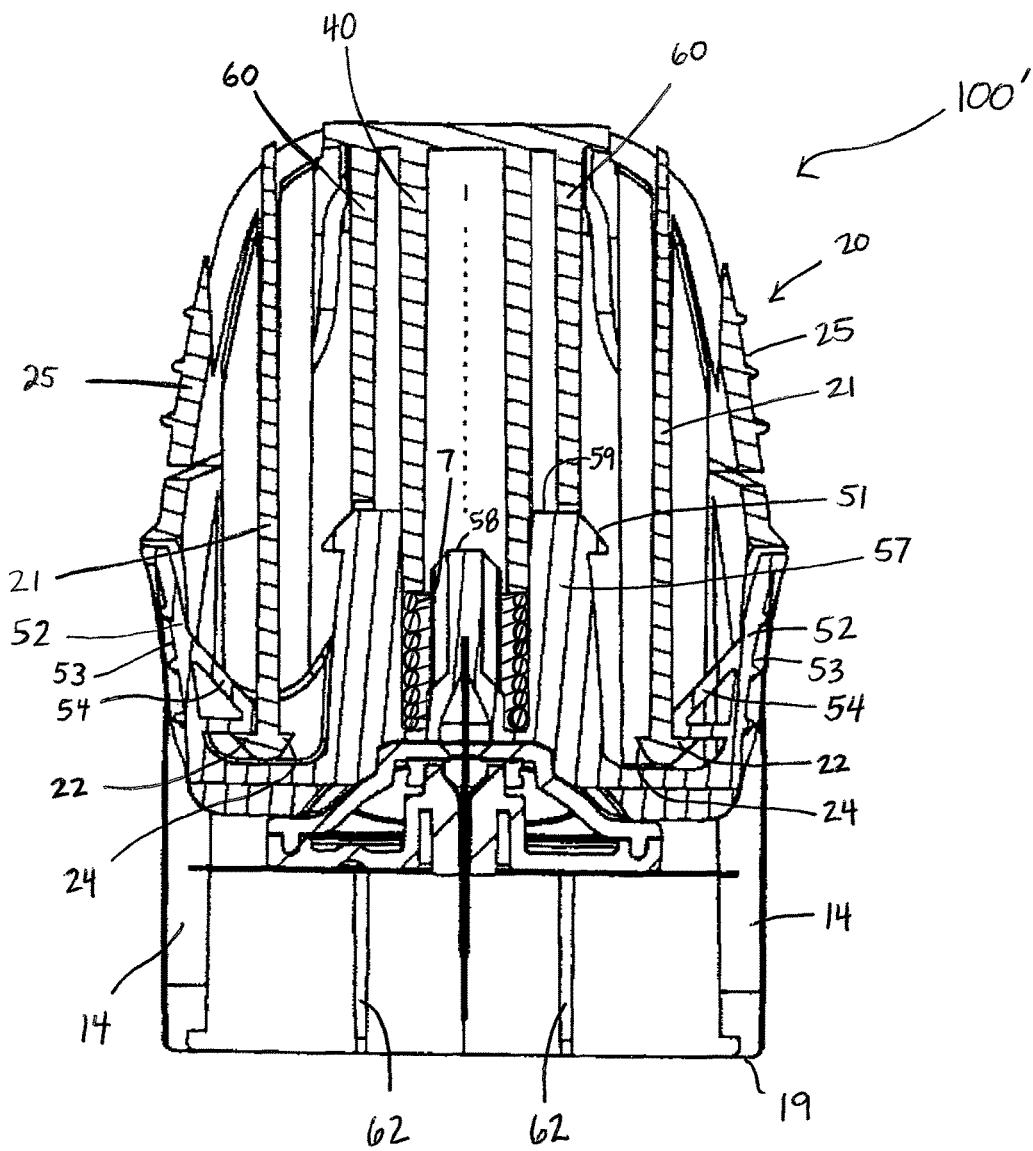
Figure 58:
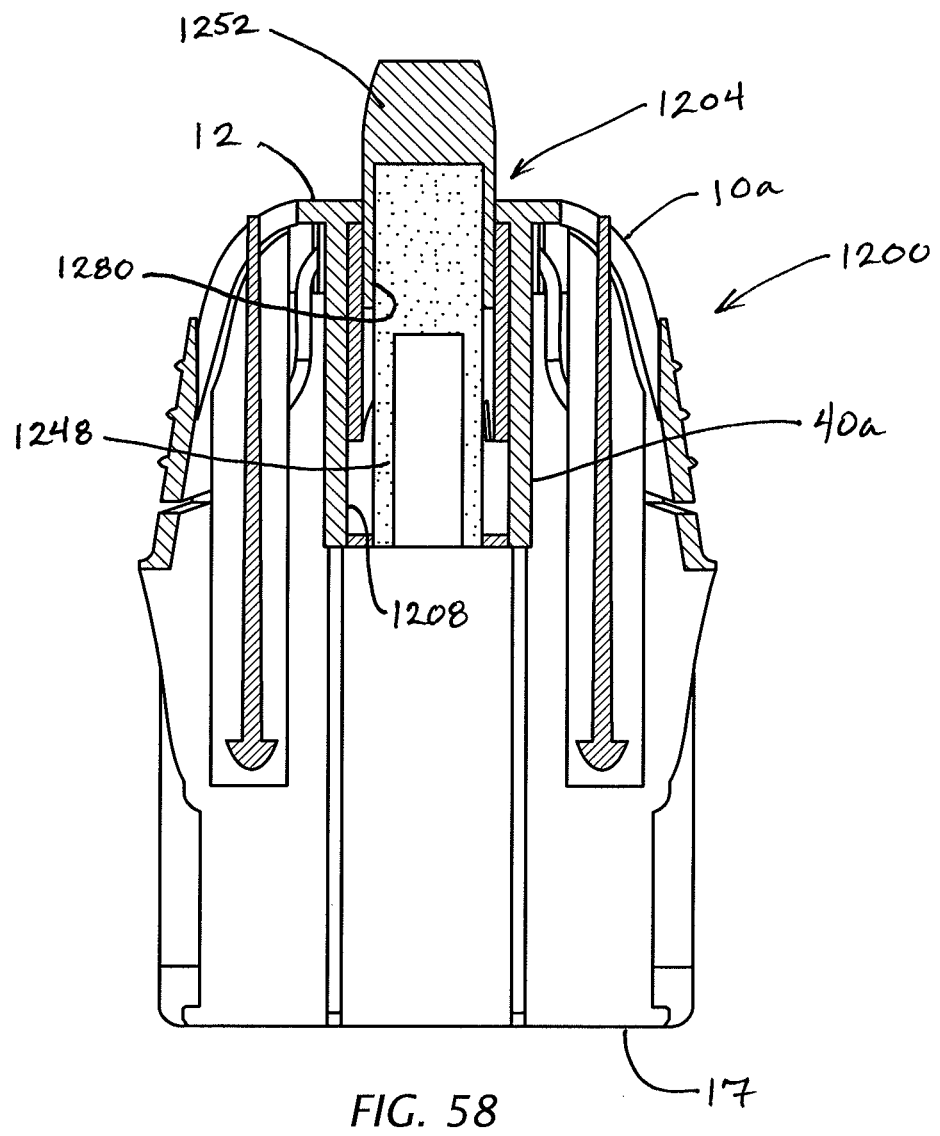
FIG. 58 is a cross-sectional view of the embodiment shown in FIG. 57.
Figure 60:
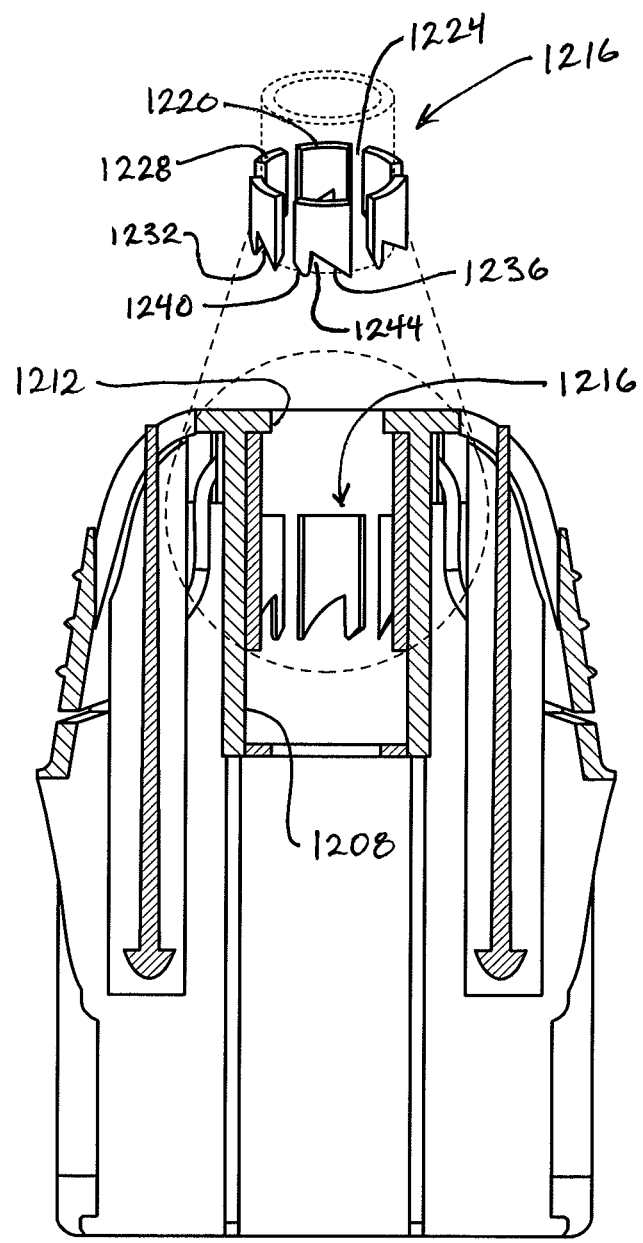
FIG. 60 is a cross-sectional view of the embodiment shown in FIG. 57 with a portion of the charging mechanism omitted and a remaining portion of the charging mechanism shown in an enlarged detail view.

Installation of an insertion set that includes the FIG. 55 embodiment of the present insertion needles may be accomplished using an embodiment of the present insertion devices that does not have driver, and that has an alignment post that is shortened from the version shown, for example, in FIG. 19. Insertion device 100', shown in FIG. 56 loaded with in insertion set that includes the FIG. 55 embodiment of the present insertion needles, is an example of such an insertion device. Insertion device 100' does not have driver 30 and it has a version of alignment post 40 that has been shortened such that the proximal end of the alignment post terminates at the compressed height of driver 7. The height and shape of post 58 of insertion needle hub 50 may be varied together with the dimensions and shapes of driver 7 and alignment post 40 to best suit a given application. For example, the height and width of post 58 may each be increased to enhance the alignment function that post 58 and alignment post 40 serve during insertion set installation. The operation of insertion device 100', including the manner of loading with an insertion set that includes the FIG. 55 embodiment of the present insertion needles and the manner of installing such an insertion set to a user, remains the same as described above for insertion device 100.

One of the present insertion needles may be configured so that the distance the bottom (or proximal, attached) end of the driver (e.g., driver 7) travels between (a) the position it will be in when an insertion set is retained by, e.g., insertion device 100 in a pre-installed position and (b) the position it will have when the particular insertion set of which it is a part is installed is less than the distance between (c) the portion of the insertion needle hub to which the driver is attached that will interfere with insertion set-stopping portion 24 (which is the bottom surface of top rim 51) and (d) the top surface of insertion set-stopping portion 24. The use of such an insertion needle in combination with such an insertion device prevents an insertion set of which such an insertion needle is a part from prematurely stopping before installation is complete.

Insertion Devices that have a Charging Mechanism and that do not have a Driver

Installation of an insertion set that includes the FIG. 55 embodiment of the present insertion needles may also be accomplished using an embodiment of the present insertion devices that does not have driver, and that has a charging mechanism. For example, insertion device 1200, as shown in FIGS. 57-63, can be loaded with an insertion set that includes the FIG. 55 embodiment of the present insertion needles (and is shown loaded with such an insertion set in FIGS. 62 and 63). Insertion device 1200 is similar in some respects to insertion devices 100 and 100' described above; thus, primarily their differences are described here. In the embodiment shown, insertion device 1200 does not have driver 30, but does have a charging mechanism 1204. Insertion device 1200 is configured so that if it retains in a pre-installed position an insertion set having a driver (e.g., the one shown in FIG. 55), the charging mechanism will be operable between an uncharged configuration and a charged configuration, as is described in more detail below and shown in FIGS. 62 and 63.

Housing 10*a* comprises an alignment post 40*a* (which is larger (e.g., wider) than alignment post 40) defining a channel 1208 (open or closed). Top end 12 of housing 10*a* is also provided with an opening 1212 extending through the top end into channel 1208. Housing 10*a* further comprises rifling 1216 within channel 1208. The rifling includes a plurality of lands 1220 and a plurality of grooves 1224 between lands 1220, as shown. Each land 1220 includes a top edge 1228 and a proximal edge 1232. Proximal edge 1232 of each land 1220 includes a relatively wider, angled charging portion 1236 and a relatively narrower, angled de-charging portion 1240. As shown, the charging and de-charging portions of proximal edge 1232 cooperate to define a charge notch 1244. In other embodiments, the charging and de-charging portions of the each land may be the same width, or the de-charging portion may be relatively wider than the charging portion.

Figure 62:
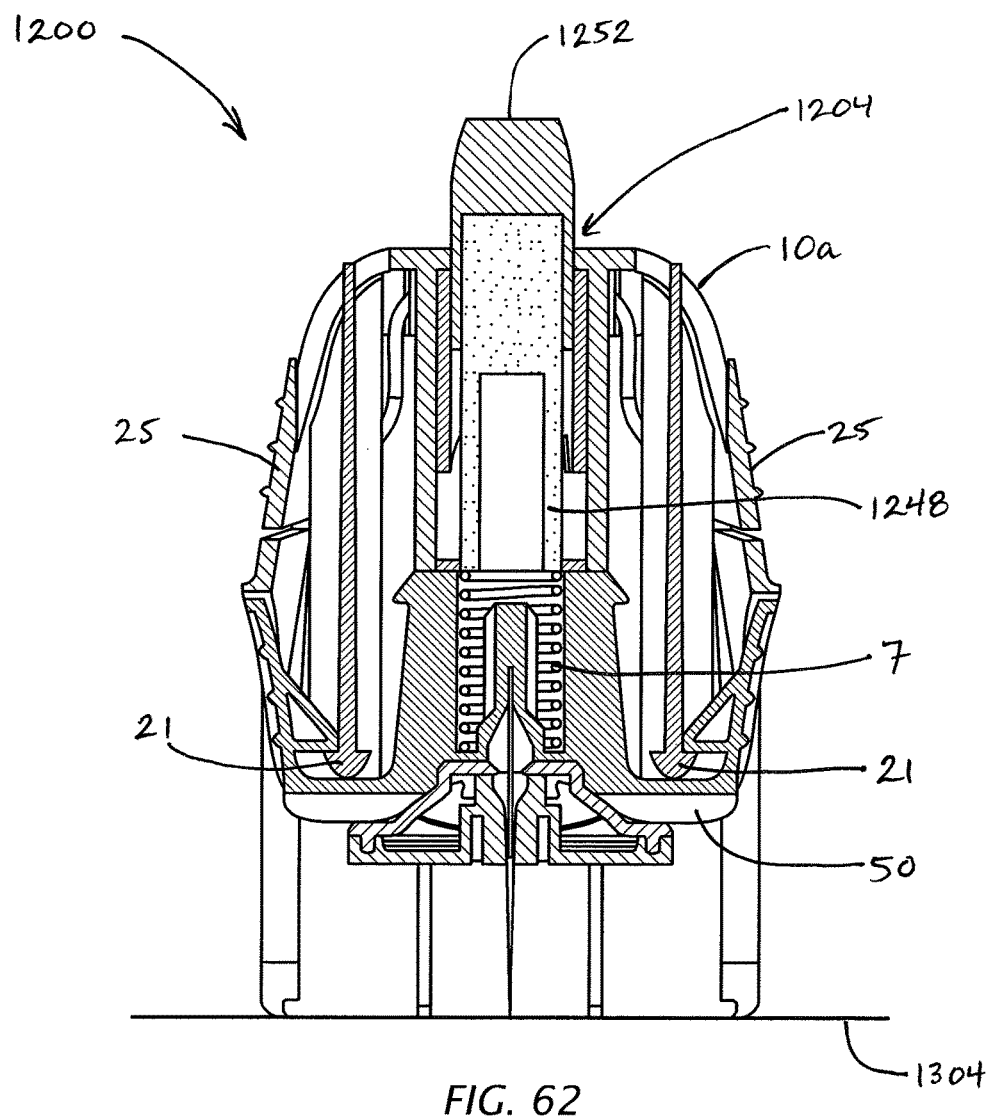
FIG. 62 is a cross-sectional view of the embodiment shown in FIG. 57 retaining an insertion set in a pre-installed position and with the charging mechanism in an uncharged configuration.
Figure 63:
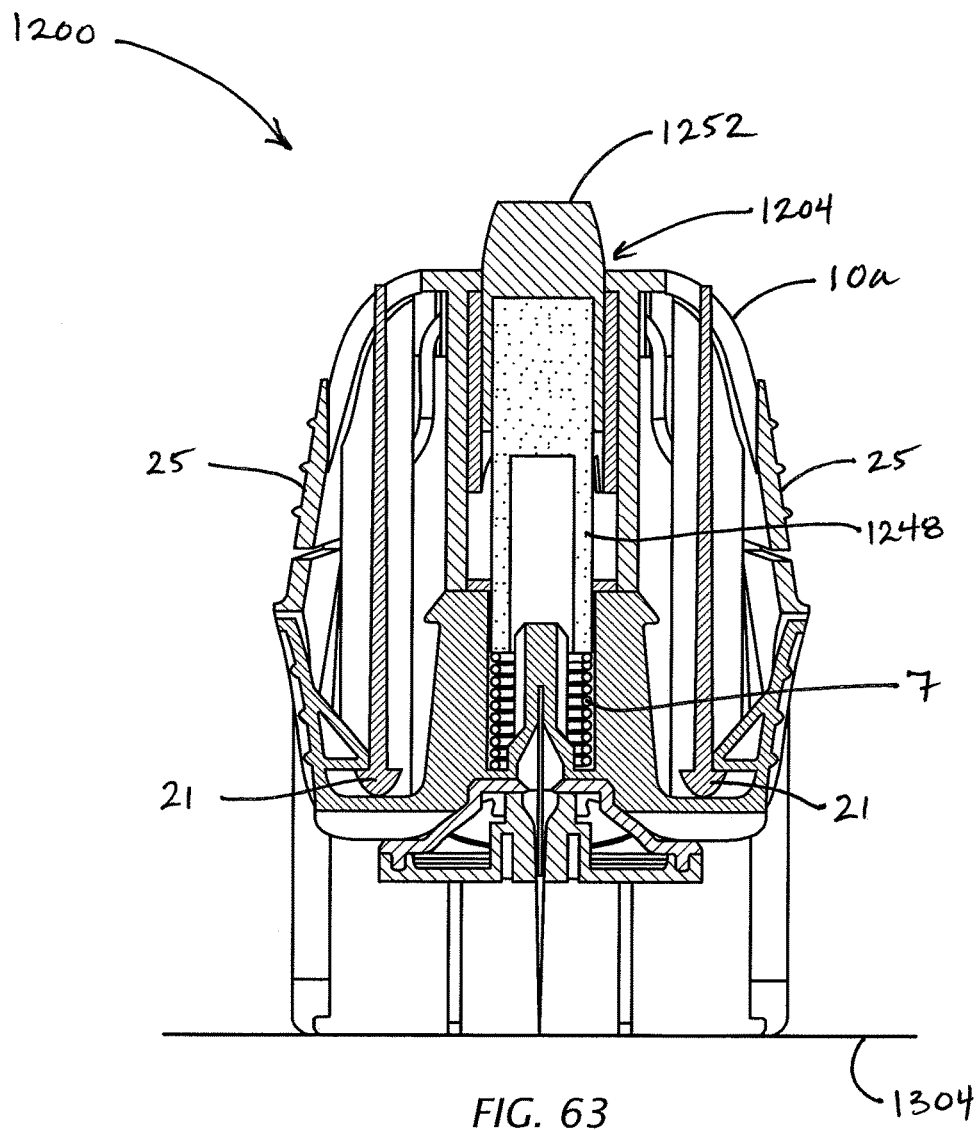
FIG. 63 is a cross-sectional view of the embodiment shown in FIG. 57 retaining an insertion set in a pre-installed position and with the charging mechanism in a charged configuration.

Charging mechanism 1204 comprises a charging post 1248 and a charging cap 1252 coupled to charging post 1248. Charging post 1248 is similar in some respects to alignment post 40 shown in FIG. 56. That is, the charging post corresponds in transverse size (e.g., diameter) to driver 7 of insertion set 50 (FIGS. 55, 62, 63). In the embodiment shown, the charging post has a top end 1256, a proximal end 1260, a plurality of protrusions 1264, and a hub 1268. When insertion device 1200 is assembled, top end 1256 is proximal to the top end 12 of housing 10*a*, and proximal end 1260 extends toward proximal end 17 of housing 10*a*. Protrusions 1264 are provided with a blade-like shape and extend outward relative to the longitudinal axis of the charging post, as shown. In the embodiment shown, the protrusions also have a length parallel to the length of the charging post. Protrusions 1264 each have a top surface 1270 that is angled to correspond with the angle of charging portion 1236 of the proximal edge of each land 1220 in rifling 1216. Hub 1268 extends radially outward from the charging post to support the protrusions. The hub can be attached to the protrusions or can be integrally formed with the charging post and the protrusions.

Charging cap 1252 has a top end 1272, a proximal end 1276, and a recess 1280 defined in proximal end 1276. The charging cap is sized to fit slidably within opening 1212 in the housing. Recess 1280 in the charging cap is sized to receive top end 1256 of the charging post, such that the charging cap can be coupled to the charging post, such as, for example, by way of a press fit, adhesive, or the like. Proximal end 1276 can also have a plurality of notches 1284 configured to engage the top angled surfaces of protrusions 1264 on the charging post.

Insertion device 1200 is configured so that if it retains in a pre-installed position an insertion set 50 having a driver 7 (e.g., FIG. 55), charging mechanism 1204 will be operable between an uncharged configuration (FIG. 62) and a charged configuration, (FIG. 63). Stated another way, insertion device 1200 is configured such that the charging mechanism will be operable between an uncharged configuration and a charged configuration if the insertion device retains in a pre-installed position an insertion set having a driver. Protrusions 1264 of the charging post interact with rifling 1216 to permit the charging mechanism to be operable between the uncharged configuration in which the charging post does not compress or only minimally compresses the driver (FIG. 62), and a charged configuration in which the charging post is closer to the proximal end of the housing such that the charging post compresses the driver (FIG. 63).

Figure 61A:
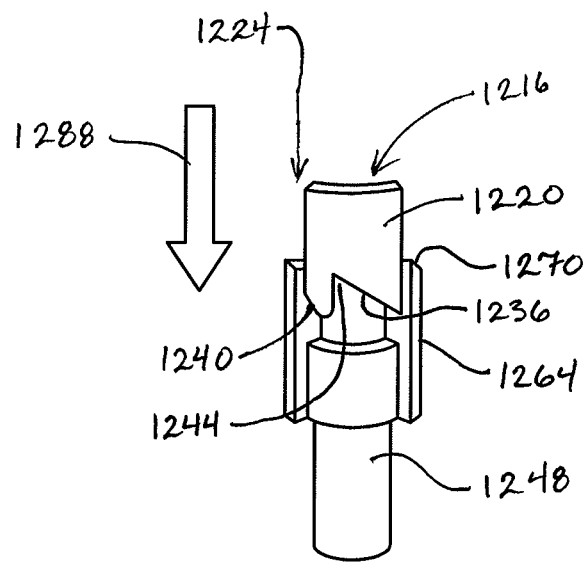
FIGS. 61A and 61B are perspective views illustrating the stepwise function of the charging mechanism of the embodiment shown in FIG. 57.
Figure 61B:
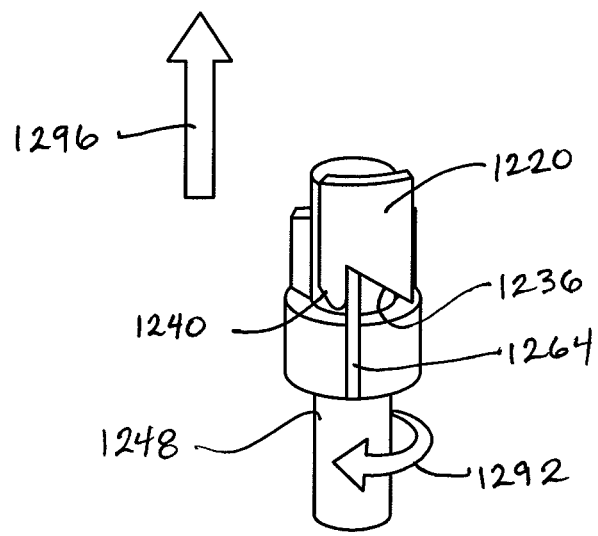

In the embodiment shown, protrusions 1264 interact with rifling 1216 to enable operation of the charging mechanism between the uncharged configuration and the charged configuration. As shown in FIG. 61A, when the depicted embodiment of the charging mechanism is in the uncharged configuration, each protrusion 1264 is aligned with a groove 1224 in rifling 1216 and is disposed between adjacent lands 1220. The charging mechanism is operable from the uncharged configuration to the charged configuration by depressing the charging cap such that charging post 1248 moves linearly in direction 1288, compressing driver 7 and permitting top surface 1270 of the protrusion to "click" and contact charging portion 1236 of the proximal end of land 1220. As illustrated by FIG. 61B, when the charging cap is released, the compressed driver and the corresponding angles of charging portion 1236 and top surface 1270 cooperate to cause the charging post to rotate in direction 1292 and move linearly in direction 1296 such that the charging post moves to a charged position in which top surface 1270 of protrusion 1264 seats in or contacts notch 1244 of the proximal end of land 1220 such that the driver is compressed (as shown in FIG. 63).

Charging mechanism 1204 is also operable from the charged configuration to the uncharged configuration by depressing the charging cap such that charging post 1248 moves linearly in direction 1288, compressing driver 7 and permitting top surface 1270 of the protrusion to "click" and contact de-charging portion 1240 of the proximal end of land 1220. When the charging cap is released, the compressed driver and the corresponding angles of de-charging portion 1240 and top surface 1270 cooperate to cause the charging post to rotate in direction 1292 and move linearly in direction 1296 such that the charging post moves to the uncharged position in which protrusion 1264 is disposed in a groove 1224 between adjacent lands 1220 of the rifling, and such that the driver is not compressed or is only minimally compressed (as shown in FIG. 62).

As shown in FIG. 63, when the depicted embodiment of the charging mechanism is in the charged configuration, driver 7 is compressed and exerts a charging force on the insertion set in the direction of the proximal end of the housing. In some embodiments, this charging force is greater than any force the driver will apply to the insertion set in the direction of the proximal end of the housing when the charging mechanism is in the uncharged configuration. In some embodiments, when the charging mechanism is in the uncharged configuration, the driver will not apply any force to the insertion set in the direction of the proximal end of the housing, such as, for example, where the driver is uncompressed in the uncharged configuration. In other embodiments, the driver is compressed, less than it is when the charging mechanism is in the charged configuration, such that when the charging mechanism is in the charged configuration the spring is more compressed than when the charging mechanism is in the uncharged configuration.

In the embodiment shown, insertion device 1200 is configured so that if it retains in a pre-installed position an insertion set, insertion set retention elements 21 will retain the insertion set in the pre-installed position, and the two insertion set retention elements are actuatable by a user to release the insertion set from the pre-installed position. More specifically, insertion set release elements 25 are each coupled to a different one of the two insertion set retention elements such that the insertion set retention elements are actuatable to release the insertion set by actuating the insertion set release elements. When insertion device 1200 retains the insertion set in a pre-installed position and the charging mechanism is in a charged configuration, the driver is compressed and exerts a charging force on the insertion set such that the insertion set release elements can be actuated to release the insertion set and the charging force will drive or propel the insertion set in the direction of the proximal end of the housing. In some embodiments, the driver is configured such that the charging force is great enough to drive or propel the full exposed length of the insertion needle into human tissue other than bone.

In some embodiments the insertion device and/or insertion set are configured such that when the insertion set is retained by the insertion device in a pre-installed position the piercing member (insertion needle) will not contact a flat surface 1304 if the proximal end of the housing is placed against the flat surface.

Figure 14:
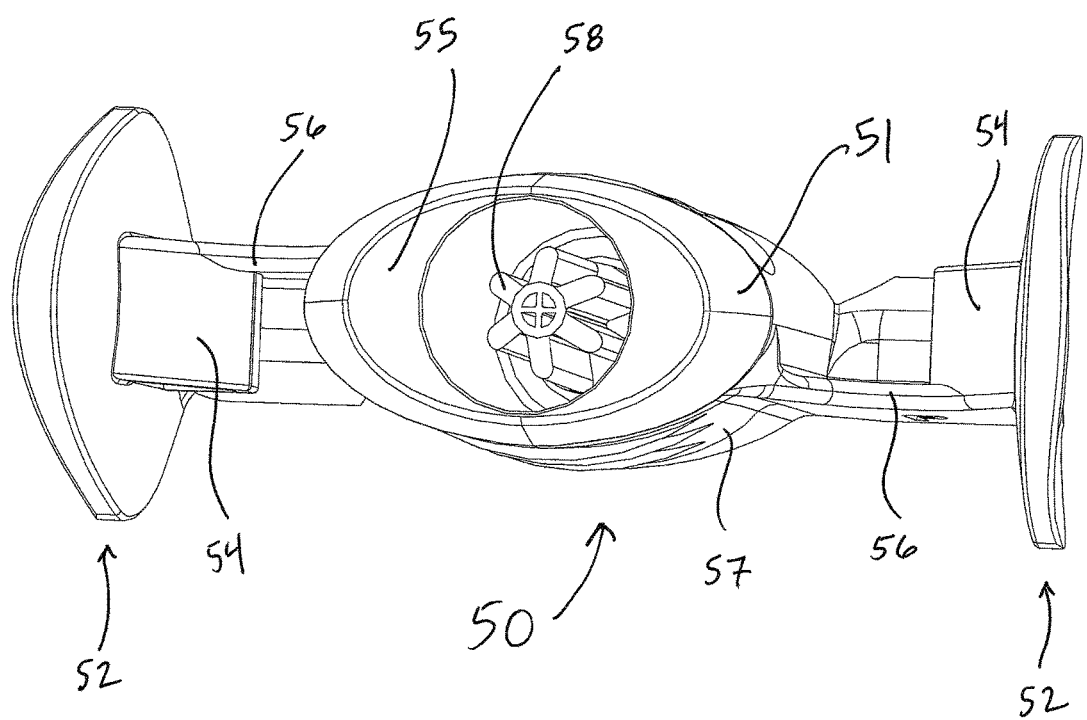
Figure 15:
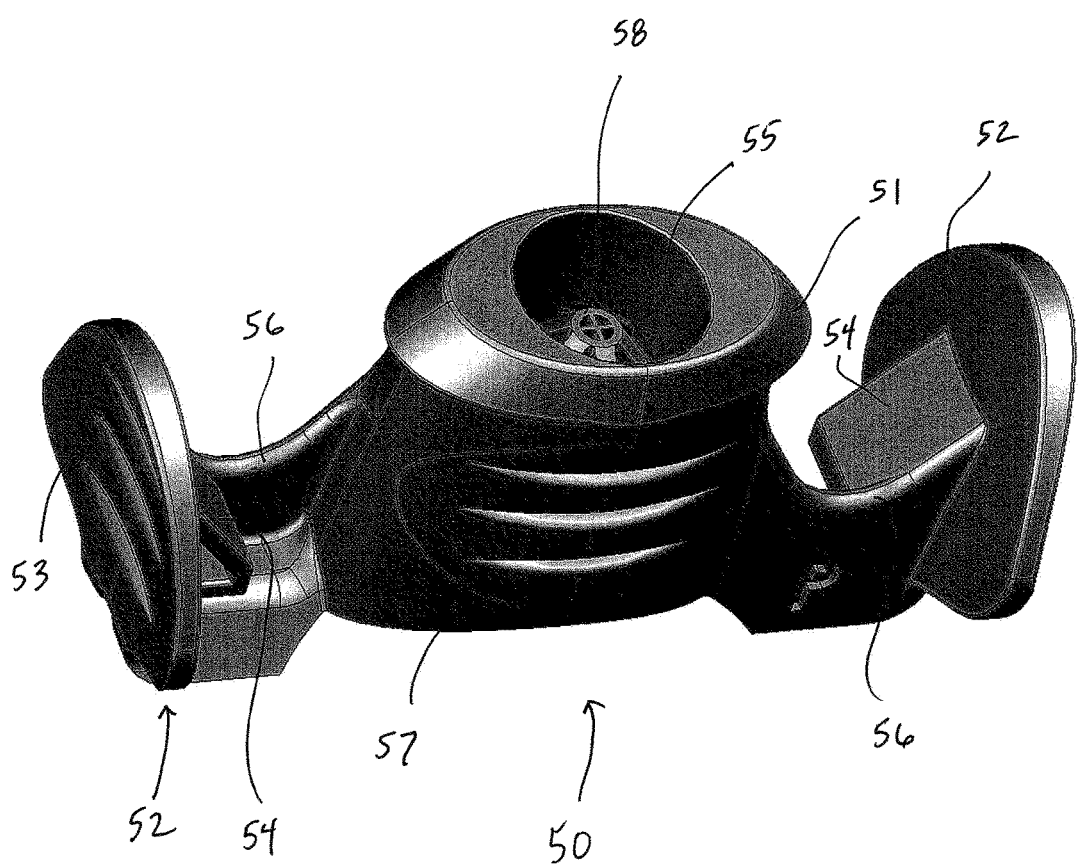
Figure 16:
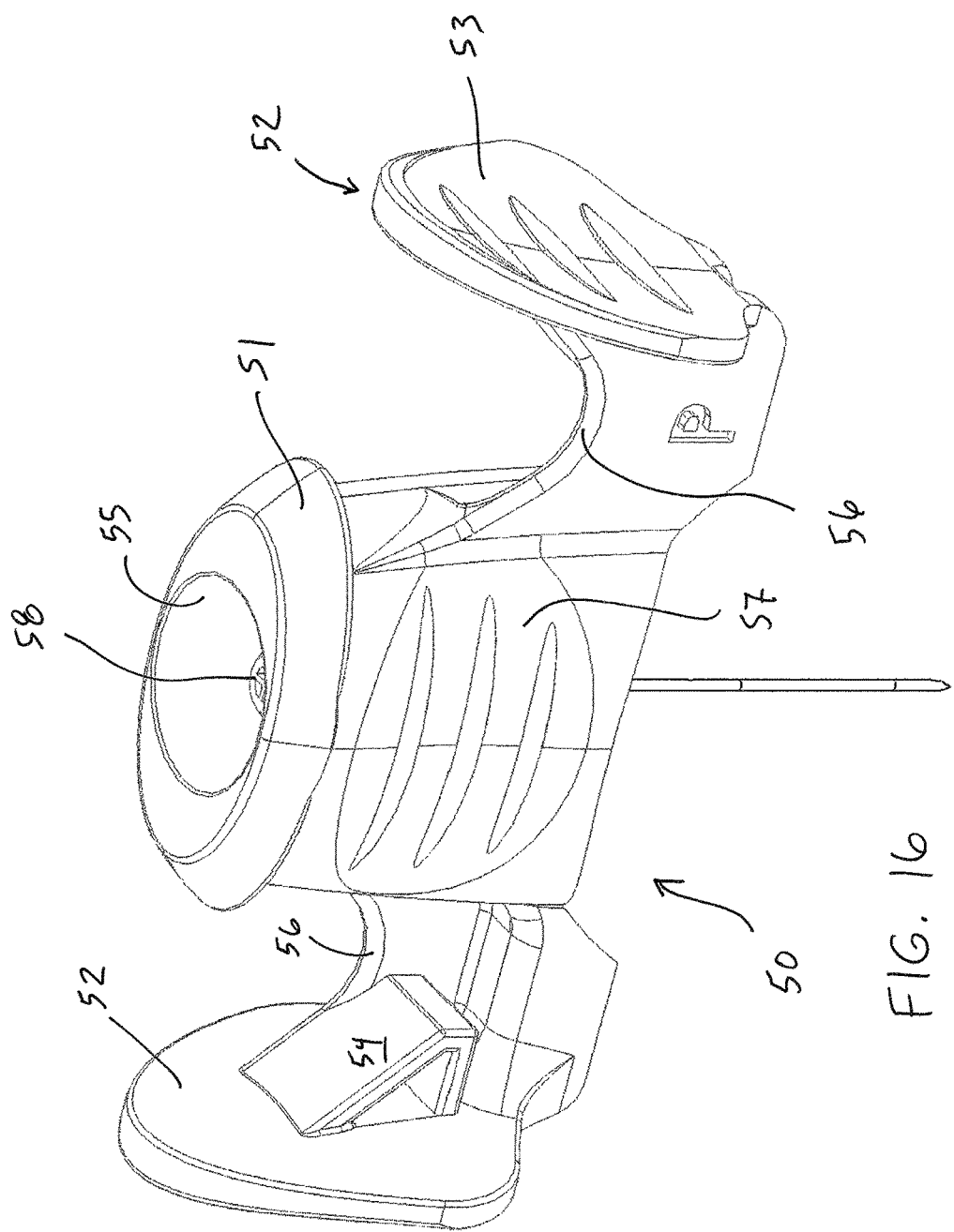

Other embodiments of insertion device 1200 may have a driver so as to be capable of functioning with insertion sets that do not have a driver (e.g., FIGS. 14-16). In some of these embodiments, the driver is coupled to the charging post.

Figure 64:
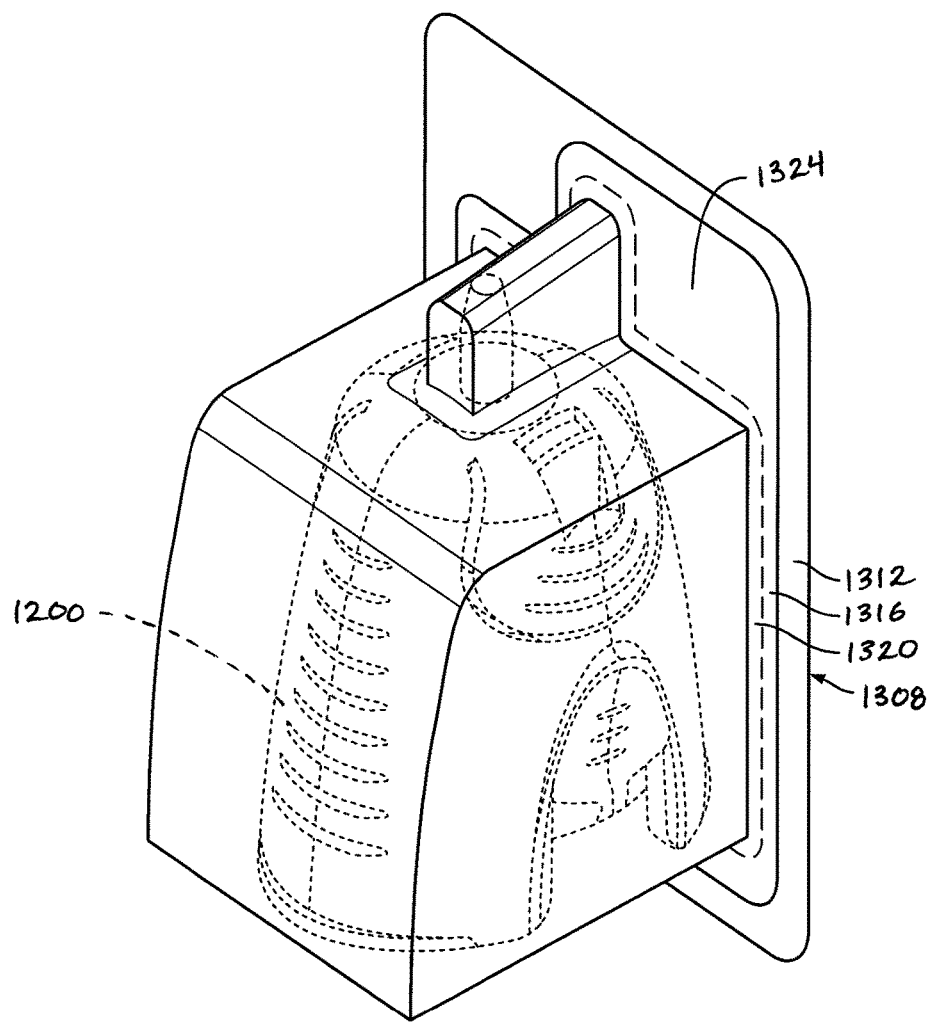
FIG. 64 is a perspective view of one of the present kits comprising an insertion device retaining an insertion set in a pre-installed position and a package enclosing the insertion device and insertion set.

Some embodiments include a kit comprising insertion set 1200 and an insertion set having a driver and a piercing member. In some of these embodiments, the charging mechanism can be in an uncharged configuration (FIG. 62). Some embodiments of the present kits may include one or more of the present insertion devices that are sterilized (e.g., with ethylene oxide or gamma radiation) and sealed in a package that has also been sterilized (or has been manufactured in from sterile materials in a sterile environment). For example, as in the embodiment shown in FIG. 64, a package 1308 encloses both of the insertion device and the insertion set retained by the insertion device. Package 1308 shown is a blister pack having a back portion 1312, a front portion 1316, and a seam 1320 attaching the front portion to the back portion. In some embodiments, the package is hermetically sealed. For example, in the embodiment shown, seam 1320 is hermetically sealed. For ease of use, front portion 1316 can also be provided with a flap 1324 that is not attached (or only weakly or partially attached) to the back portion 1316 so as to facilitate separation of the front and back portions such as, for example, to remove the insertion device from the package for use. The package may include instructions for use on the outside of the package or on material (e.g., a folded piece of paper) placed in the package. Some embodiments of the present kits include a package containing multiple trays for resale; in such embodiments, one set of instructions for use may be placed in the package.

Some embodiments include a method of installing an insertion set to a user, comprising: positioning insertion device 1200 over an installation site on the user's skin, the insertion device retaining an insertion set in a pre-installed position and the insertion set having a driver; and releasing the insertion set by actuating the insertion set retention mechanism, thus allowing the driver to advance a piercing member and a cannula of the insertion set into the user's skin.

The present insertion devices can be individually packaged for sale and, in some embodiments, may be re-used. The package may contain one insertion device (or more) and a set of instructions for use. Thus, some embodiments of the present invention include, consist of, or consist essentially of one of the present insertion devices, a set of instructions for use, and a package (which may take the form of a pouch, tray, box (such as a box containing multiple trays), tube, or the like). The package may include the instructions for use on the outside of the package or on material (e.g., a folded piece of paper) placed in the package. The insertion device may be placed in the package with a suitable insertion set already coupled to it.

The present insertion devices may help a user to install an insertion set (such as an I-Port® infusion port, manufactured and sold by Patton Medical Devices of Austin, Tex., that has been fitted with an appropriately configured insertion needle hub) by automating, at least to some extent, an otherwise manual installation process. Insertion set installation using one of the present insertion devices is anticipated to be more repeatable and precise than normal manual installation, and may help to reduce the incidence of mis-installation and may lessen the overall discomfort of installation.

The present instruction methods, which may be used by manufacturers or their representatives to explain how embodiments of the present devices may be used to persons who will ultimately demonstrate their use to end-users, may be accomplished in some embodiments by a live demonstration in the presence of the person and in other embodiments by a recorded or simulated demonstration that is played for the person. An example of a recorded demonstration is one that was carried out by a person and captured on camera. An example of a simulated demonstration is one that did not actually occur, and that instead was generated using a computer system and a graphics program. In the case of a recorded or simulated demonstration, the demonstration may exist in any suitable form—such as a on DVD or in any suitable video file (such as an .mpg, .mov., .qt, .rm, .swf, or .wmv file)—and the instructing may be accomplished by playing the demonstration for the viewer using any suitable computer system. The viewer or viewers may cause the demonstration to play. For example, the viewer may access the recorded or simulated demonstration file using the internet, or any suitable computer system that provides the viewer with access to the file.

The present insertion devices and the insertion needle hubs of the present insertion needles may be made from any of a variety of suitable materials that are well-known to those of ordinary skill in the art, including medical grade plastics. The material chosen may be translucent, transparent, semi-transparent, or opaque in different embodiments.

The present insertion devices are not intended to be limited to the particular forms disclosed. Rather, they include all modifications, equivalents, and alternatives falling within the scope of the claims. For example, while the elements of the embodiment of insertion device 100 shown in the figures (other than the driver) are formed from a single piece of material (such as may be achieved using injection molding), certain of the depicted elements may be separate pieces that are coupled together. For example, the retention mechanism may be a separate element (or elements) from the housing, rather than integral with it as is the depicted embodiment of insertion device 100. This is also true of insertion device 100'. Furthermore, which the manner in which retention elements 21 are coupled to housing 10 of either insertion devices 100, 100' or 1200 is in a hinged manner, in other embodiments the retention elements may be coupled to the housing such that lateral movement of the release elements along a straight line accomplishes contact with the retention elements sufficient to release a retained insertion set.

As another example, while two retention elements are included in the depicted retention mechanism, other embodiments of that version of the present insertion devices may have only one retention element or more than two (e.g., 3 or 4) retention elements.

As another example, while a spring is depicted for driver 30 of insertion device 100, other drivers may be used in other embodiments, including those that operate under forces that are pneumatic, hydraulic, a combination of both. The forces may also be computer-controlled. This is true of driver 7 of the FIG. 55 insertion needle.

The claims are not to be interpreted as including means-plus- or step-plus-function limitations, unless such a limitation is explicitly recited in a given claim using the phrase(s) "means for" or "step for," respectively.

The invention claimed is:

1. An insertion system comprising:
   an insertion device comprising:
      a housing having a proximal end; and
      an insertion set retention mechanism coupled to the housing, the insertion set retention mechanism including two insertion set retention elements actuatable by a user;
   an insertion set that can be coupled to the insertion device, the insertion set including an insertion needle hub and a needle extending from the insertion needle hub, and an insertion set base coupled to the needle, where the insertion set retention mechanism directly contacts the insertion needle hub when the insertion set is in a loaded, pre-installed position; and
   a driver coupled to the housing or to the insertion needle hub;
   where the driver directly contacts and applies a force to the insertion set in the direction of the proximal end of the housing when the insertion set is in a loaded, pre-installed position, and the insertion device is configured such that after the insertion set is installed to a user, removal of the insertion device from the installed insertion set without manipulation of the two insertion set retention elements results in separation of the insertion device from the insertion needle hub.

2. The insertion system of claim 1, where the housing has an interior surface that defines an inner cavity, and the insertion device also includes an alignment post coupled to the housing and extending from a top portion of the inner cavity of the housing and toward the proximal end of the housing, and an insertion axis centered in the alignment post.

3. The insertion system of claim 2, where the driver comprises a spring coupled to the housing near the top portion of the interior surface of the housing, the spring being positioned around the alignment post.

4. The insertion system of claim 2, where the housing includes an interior rib structure.

5. The insertion system of claim 1, where the insertion set retention mechanism also includes two release elements coupled to the two insertion set retention elements so that actuation of the release elements causes the insertion set retention elements to move.

6. The insertion system of claim 1, where the housing includes a top end and a proximal end edge that includes two slots that are positioned on opposite sides of the housing and that each begins at the proximal end of the housing, extends toward the top end of the housing, and terminates below the top end of the housing.

7. An insertion system comprising:
   an insertion device comprising:
      a housing having a proximal end; and
      an insertion set retention mechanism coupled to the housing, the insertion set retention mechanism including two insertion set retention elements actuatable by a user, the insertion set retention mechanism also including two release elements coupled to the two insertion set retention elements so that actuation of the release elements causes the insertion set retention elements to move, where each insertion set retention element includes an insertion set-engaging portion, and the two insertion set-engaging portions extend away from each other in opposite directions;
   an insertion set that can be coupled to the insertion device, the insertion set including an insertion needle hub and a needle extending from the insertion needle hub, and an insertion set base coupled to the needle, where the insertion set retention mechanism directly contacts the insertion needle hub when the insertion set is in a loaded, pre-installed position; and
   a driver coupled to the housing or to the insertion needle hub;
   where the driver directly contacts and applies a force to the insertion set in the direction of the proximal end of the housing when the insertion set is in a loaded, pre-installed position, and the insertion device is configured such that after the insertion set is installed to a user, removal of the insertion device from the installed insertion set results in separation of the insertion device from the insertion needle hub.

8. The insertion system of claim 7, where each insertion set retention element also includes an insertion set-stopping portion, and the insertion set-stopping portion of a given insertion set retention element extends away from the insertion set-engaging portion of that insertion set retention element.

9. An insertion system comprising:
   an insertion device comprising:
      a housing having a proximal end;
      a driver coupled to the housing; and an insertion set retention mechanism coupled to the housing, the insertion set retention mechanism including two insertion set retention elements actuatable by a user, the insertion set retention mechanism being configured to retain in a pre-installed position an insertion set that includes an insertion needle;

an insertion set that can be coupled to the insertion device, the insertion set including an insertion needle hub and a needle extending from the insertion needle hub, and an insertion set base coupled to the needle, where the insertion set retention mechanism direct contacts the insertion needle hub when the insertion set is in a loaded, pre-installed position; and where the driver directly contacts and applies a force to the insertion set in the direction of the proximal end of the housing when the insertion set is in the loaded, pre-installed position, and the insertion device is configured such that after the insertion set is installed to a user, removal of the insertion device from the installed insertion set without manipulation of the two insertion set retention elements results in separation of the insertion device from the insertion needle hub.

10. The insertion system of claim 9, where the insertion set retention mechanism also includes two release elements coupled to the two insertion set retention elements so that actuation of the release elements causes the insertion set retention elements to move.

11. An insertion system comprising:
an insertion device comprising:
a housing having a proximal end;
a driver coupled to the housing; and
an insertion set retention mechanism coupled to the housing, the insertion set retention mechanism including two insertion set retention elements actuatable by a user, the insertion set retention mechanism also including two release elements coupled to the two insertion set retention elements so that actuation of the release elements causes the insertion set retention elements to move, where each insertion set retention element includes an insertion set-engaging portion, and the two insertion set-engaging portions extend away from each other in opposite directions, the insertion set retention mechanism being configured to retain in a pre-installed position an insertion set that includes an insertion needle;

an insertion set that can be coupled to the insertion device, the insertion set including an insertion needle hub and a needle extending from the insertion needle hub, and an insertion set base coupled to the needle, where the insertion set retention mechanism direct contacts the insertion needle hub when the insertion set is in a loaded, pre-installed position; and where the driver directly contacts and applies a force to the insertion set in the direction of the proximal end of the housing when the insertion set is in the loaded, pre-installed position, and the insertion device is configured such that after the insertion set is installed to a user, removal of the insertion device from the installed insertion set results in separation of the insertion device from the insertion needle hub.

12. The insertion system of claim 11, where each insertion set retention element also includes an insertion set-stopping portion, and the insertion set-stopping portion of a given insertion set retention element extends away from the insertion set-engaging portion of that insertion set retention element.

13. An insertion system comprising:
an insertion device comprising:
a housing having a proximal end, a top end, and a proximal end edge that includes two slots that are positioned on opposite sides of the housing and that each begins at the proximal end of the housing, extends toward the top end of the housing, and terminates below the top end of the housing; and
an insertion set retention mechanism coupled to the housing, the insertion set retention mechanism including two insertion set retention elements actuatable by a user, the insertion set retention mechanism also including two release elements coupled to the two insertion set retention elements so that actuation of the release elements causes the insertion set retention elements to move, where each release element has an exterior user-actuatable surface, and at least a substantial portion of the exterior user-actuatable surface of one of the release elements is located between one of the slots and the top end of the housing, and at least a substantial portion of the exterior user-actuatable surface of the other release element is located between the other slot and the top end of the housing;

an insertion set that can be coupled to the insertion device, the insertion set including an insertion needle hub and a needle extending from the insertion needle hub, and an insertion set base coupled to the needle, where the insertion set retention mechanism directly contacts the insertion needle hub when the insertion set is in a loaded, pre-installed position; and a driver coupled to the housing or to the insertion needle hub;

where the driver directly contacts and applies a force to the insertion set in the direction of the proximal end of the housing when the insertion set is in a loaded, pre-installed position, and the insertion device is configured such that after the insertion set is installed to a user, removal of the insertion device from the installed insertion set results in separation of the insertion device from the insertion needle hub.

14. An insertion system comprising:
an insertion device comprising:
a housing having a proximal end and has an interior surface that defines an inner cavity, the housing also having an interior rib structure;
an alignment post coupled to the housing and extending from a top portion of the inner cavity of the housing and toward the proximal end of the housing, and an insertion axis centered in the alignment post; and
an insertion set retention mechanism coupled to the housing, the insertion set retention mechanism including two insertion set retention elements actuatable by a user;

an insertion set that can be coupled to the insertion device, the insertion set including an insertion needle hub and a needle extending from the insertion needle hub, and an insertion set base coupled to the needle, where the insertion set retention mechanism directly contacts the insertion needle hub when the insertion set is in a loaded, pre-installed position; and a driver coupled to the housing or to the insertion needle hub;

where the driver directly contacts and applies a force to the insertion set in the direction of the proximal end of the housing when the insertion set is in a loaded, pre-installed position, and the insertion device is configured such that after the insertion set is installed to a user, removal of the insertion device from the installed insertion set results in separation of the insertion device from the insertion needle hub; and where the interior rib structure includes two ribs positioned parallel to the alignment post, and each rib includes a rib slot positioned beside the driver.

* * * * *